United States Patent
Tang et al.

(10) Patent No.: US 12,400,736 B2
(45) Date of Patent: Aug. 26, 2025

(54) METHODS AND PROCESSES FOR NON-INVASIVE ESTIMATION OF FETAL FRACTION

(71) Applicant: SEQUENOM, INC., San Diego, CA (US)

(72) Inventors: Lin Tang, San Diego, CA (US); Cosmin Deciu, San Diego, CA (US)

(73) Assignee: SEQUENOM, INC., San Diego, CA (US)

(*) Notice: Subject to any disclaimer, the term of this patent is extended or adjusted under 35 U.S.C. 154(b) by 1175 days.

(21) Appl. No.: 17/226,580

(22) Filed: Apr. 9, 2021

(65) Prior Publication Data
US 2021/0233609 A1    Jul. 29, 2021

Related U.S. Application Data

(63) Continuation of application No. 15/647,171, filed on Jul. 11, 2017, now Pat. No. 11,004,537, which is a continuation of application No. 14/127,912, filed as application No. PCT/US2012/043388 on Jun. 20, 2012, now abandoned.

(60) Provisional application No. 61/500,842, filed on Jun. 24, 2011.

(51) Int. Cl.
| | | |
|---|---|---|
| *G16B 20/20* | (2019.01) | |
| *C12Q 1/6869* | (2018.01) | |
| *C12Q 1/6874* | (2018.01) | |
| *G16B 20/00* | (2019.01) | |
| *G16B 20/10* | (2019.01) | |
| *G16B 30/00* | (2019.01) | |
| *G16B 30/10* | (2019.01) | |
| *G16B 40/00* | (2019.01) | |
| *G16B 40/20* | (2019.01) | |
| *G16B 40/30* | (2019.01) | |

(52) U.S. Cl.
CPC ........... *G16B 20/20* (2019.02); *C12Q 1/6869* (2013.01); *C12Q 1/6874* (2013.01); *G16B 20/00* (2019.02); *G16B 30/10* (2019.02); *G16B 40/20* (2019.02); *G16B 40/30* (2019.02); *G16B 20/10* (2019.02); *G16B 30/00* (2019.02); *G16B 40/00* (2019.02)

(58) Field of Classification Search
CPC ........ G16B 20/20; G16B 20/00; G16B 30/10; G16B 40/20; G16B 40/30; G16B 20/10; G16B 30/00; G16B 40/00; C12Q 1/6869; C12Q 1/6874
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,075,212 A | 12/1991 | Rotbart |
| 5,091,652 A | 2/1992 | Mathies et al. |
| 5,432,054 A | 7/1995 | Saunders et al. |
| 5,445,934 A | 8/1995 | Fodor et al. |
| 5,670,325 A | 9/1997 | Lapidus et al. |
| 5,720,928 A | 2/1998 | Schwartz |
| 5,786,146 A | 7/1998 | Herman et al. |
| 5,928,870 A | 7/1999 | Lapidus et al. |
| 5,939,598 A | 8/1999 | Kucherlapati et al. |
| 6,015,714 A | 1/2000 | Baldarelli et al. |
| 6,090,550 A | 7/2000 | Collinge et al. |
| 6,100,029 A | 8/2000 | Lapidus et al. |
| 6,214,558 B1 | 4/2001 | Shuber et al. |
| 6,214,560 B1 | 4/2001 | Yguerabide et al. |
| 6,235,475 B1 | 5/2001 | Brenner et al. |
| 6,258,540 B1 | 7/2001 | Wainscoat et al. |
| 6,263,286 B1 | 7/2001 | Gilmanshin et al. |
| 6,403,311 B1 | 6/2002 | Chan |
| 6,566,101 B1 | 5/2003 | Shuber et al. |
| 6,617,133 B1 | 9/2003 | Noda et al. |
| 6,772,070 B2 | 8/2004 | Gilmanshin et al. |
| 6,818,395 B1 | 11/2004 | Quake et al. |
| 6,927,028 B2 | 8/2005 | Dennis et al. |
| 6,936,422 B2 | 8/2005 | El et al. |
| 7,005,264 B2 | 2/2006 | Su et al. |
| 7,169,560 B2 | 1/2007 | Lapidus et al. |

(Continued)

FOREIGN PATENT DOCUMENTS

| | | |
|---|---|---|
| WO | 00/06770 A1 | 2/2000 |
| WO | 01/32887 A1 | 5/2001 |

(Continued)

OTHER PUBLICATIONS

Larrabee PB. Microarray analysis of cell-free fetal DNA in amniotic fluid: a prenatal molecular karyotype. American Journal of Human Genetics 75: 485-491. (Year: 2004).*
Straver R. Wisecondor: detection of fetal aberrations from shallow sequencing maternal plasma based on a within-sample comparison scheme. Nucleic Acids Research 42(5): 9 pgs. (Year: 2013).*
DNA copy, http://bioconductor.org/packages/2.12/bioc/html/DNAcopy.html, Apr. 24, 2013, 21 pages.

(Continued)

*Primary Examiner* — Olivia M. Wise
*Assistant Examiner* — Robert J. Kallal
(74) *Attorney, Agent, or Firm* — Kilpatrick Townsend & Stockton, LLP

(57) ABSTRACT

Provided in part herein are methods and processes that can be used for non-invasive assessment of a genetic variation which can lead to diagnosis of a particular medical condition or conditions. Such methods and processes can, for example, identify dissimilarities or similarities for one or more features between a subject data set and a reference data set, generate a multidimensional matrix, reduce the matrix into a representation and classify the representation into one or more groups. Methods and processes described herein are applicable to data in biotechnology and other fields.

12 Claims, 15 Drawing Sheets

(56) References Cited

U.S. PATENT DOCUMENTS

| | | |
|---|---|---|
| 7,279,337 B2 | 10/2007 | Zhu |
| 7,282,337 B1 | 10/2007 | Harris |
| 7,947,454 B2 | 5/2011 | Akeson et al. |
| 7,960,105 B2 | 6/2011 | Schwartz et al. |
| 7,972,858 B2 | 7/2011 | Meller et al. |
| 8,688,388 B2 | 4/2014 | Dzakula et al. |
| 11,004,537 B2 | 5/2021 | Tang et al. |
| 2001/0014850 A1 | 8/2001 | Gilmanshin et al. |
| 2001/0049102 A1 | 12/2001 | Huang et al. |
| 2002/0006621 A1 | 1/2002 | Bianchi |
| 2002/0045176 A1 | 4/2002 | Lo et al. |
| 2002/0110818 A1 | 8/2002 | Chan |
| 2002/0119469 A1 | 8/2002 | Shuber et al. |
| 2002/0164629 A1 | 11/2002 | Quake et al. |
| 2003/0013101 A1 | 1/2003 | Balasubramanian |
| 2003/0082600 A1 | 5/2003 | Olek et al. |
| 2003/0164629 A1 | 9/2003 | Bigolin |
| 2003/0180779 A1 | 9/2003 | Lofton-Day et al. |
| 2003/0207326 A1 | 11/2003 | Su et al. |
| 2003/0232346 A1 | 12/2003 | Su |
| 2004/0081993 A1 | 4/2004 | Cantor et al. |
| 2004/0110208 A1 | 6/2004 | Chan et al. |
| 2004/0137470 A1 | 7/2004 | Dhallan |
| 2005/0019784 A1 | 1/2005 | Su et al. |
| 2005/0095599 A1 | 5/2005 | Pittaro et al. |
| 2005/0112590 A1 | 5/2005 | Boom et al. |
| 2005/0147980 A1 | 7/2005 | Berlin et al. |
| 2005/0164241 A1 | 7/2005 | Hahn et al. |
| 2005/0227278 A1 | 10/2005 | Wall |
| 2005/0287592 A1 | 12/2005 | Kless |
| 2006/0046258 A1 | 3/2006 | Lapidus et al. |
| 2006/0063171 A1 | 3/2006 | Akeson et al. |
| 2006/0068440 A1 | 3/2006 | Chan et al. |
| 2006/0252071 A1 | 11/2006 | Lo et al. |
| 2007/0065823 A1 | 3/2007 | Dressman et al. |
| 2007/0202525 A1 | 8/2007 | Quake et al. |
| 2008/0020390 A1 | 1/2008 | Mitchell et al. |
| 2008/0070792 A1 | 3/2008 | Stoughton et al. |
| 2008/0081330 A1 | 4/2008 | Kahvejian |
| 2008/0138809 A1 | 6/2008 | Kapur et al. |
| 2008/0187915 A1 | 8/2008 | Polonsky et al. |
| 2008/0233575 A1 | 9/2008 | Harris et al. |
| 2009/0026082 A1 | 1/2009 | Rothberg et al. |
| 2009/0029377 A1 | 1/2009 | Lo et al. |
| 2009/0075252 A1 | 3/2009 | Harris et al. |
| 2009/0129647 A1 | 5/2009 | Dimitrova et al. |
| 2009/0191565 A1 | 7/2009 | Lapidus et al. |
| 2009/0197257 A1 | 8/2009 | Harris |
| 2009/0317817 A1 | 12/2009 | Oeth et al. |
| 2009/0317818 A1 | 12/2009 | Ehrich et al. |
| 2010/0105049 A1 | 4/2010 | Ehrich et al. |
| 2010/0109197 A1 | 5/2010 | Hansen et al. |
| 2010/0112575 A1 | 5/2010 | Fan et al. |
| 2010/0112590 A1 | 5/2010 | Lo et al. |
| 2010/0138165 A1 | 6/2010 | Fan et al. |
| 2010/0151471 A1 | 6/2010 | Faham et al. |
| 2010/0216151 A1 | 8/2010 | Lapidus et al. |
| 2010/0216153 A1 | 8/2010 | Lapidus et al. |
| 2010/0261285 A1 | 10/2010 | Goldstein et al. |
| 2010/0310421 A1 | 12/2010 | Oliver et al. |
| 2010/0330557 A1 | 12/2010 | Yakhini et al. |
| 2011/0086769 A1 | 4/2011 | Oliphant et al. |
| 2011/0159601 A1 | 6/2011 | Golovchenko et al. |
| 2011/0171634 A1 | 7/2011 | Xiao et al. |
| 2011/0174625 A1 | 7/2011 | Akeson et al. |
| 2011/0177498 A1 | 7/2011 | Clarke et al. |
| 2011/0177517 A1 | 7/2011 | Rava et al. |
| 2011/0201507 A1 | 8/2011 | Rava et al. |
| 2011/0224087 A1 | 9/2011 | Quake et al. |
| 2011/0230358 A1 | 9/2011 | Rava |
| 2011/0288780 A1 | 11/2011 | Rabinowitz et al. |
| 2011/0294699 A1 | 12/2011 | Lee et al. |
| 2011/0312503 A1 | 12/2011 | Chuu et al. |
| 2011/0319272 A1 | 12/2011 | Fan et al. |
| 2012/0046877 A1 | 2/2012 | Hyland et al. |
| 2012/0122701 A1 | 5/2012 | Ryan et al. |
| 2012/0165203 A1 | 6/2012 | Quake et al. |
| 2012/0184449 A1 | 7/2012 | Hixson et al. |
| 2012/0214678 A1 | 8/2012 | Rava et al. |
| 2012/0264115 A1 | 10/2012 | Rava |
| 2012/0270212 A1 | 10/2012 | Rabinowitz et al. |
| 2012/0270739 A1 | 10/2012 | Rava et al. |
| 2013/0012399 A1 | 1/2013 | Myers et al. |
| 2013/0022977 A1 | 1/2013 | Lapidus et al. |
| 2013/0034546 A1 | 2/2013 | Rava et al. |
| 2013/0085681 A1 | 4/2013 | Deciu et al. |
| 2013/0096011 A1 | 4/2013 | Rava et al. |
| 2013/0130921 A1 | 5/2013 | Gao et al. |
| 2013/0130923 A1 | 5/2013 | Ehrich et al. |
| 2013/0150253 A1 | 6/2013 | Deciu et al. |
| 2013/0196317 A1 | 8/2013 | Lapidus et al. |
| 2013/0237431 A1 | 9/2013 | Lo et al. |
| 2013/0245961 A1 | 9/2013 | Lo et al. |
| 2013/0261983 A1 | 10/2013 | Dzakula et al. |
| 2013/0288244 A1 | 10/2013 | Deciu et al. |
| 2013/0304392 A1 | 11/2013 | Deciu et al. |
| 2013/0309666 A1 | 11/2013 | Deciu et al. |
| 2013/0325360 A1 | 12/2013 | Deciu et al. |
| 2013/0338933 A1 | 12/2013 | Deciu et al. |
| 2014/0100792 A1 | 4/2014 | Deciu et al. |
| 2014/0180594 A1 | 6/2014 | Kim et al. |
| 2014/0235474 A1 | 8/2014 | Tang et al. |
| 2014/0242588 A1 | 8/2014 | Van Den Boom et al. |
| 2014/0322709 A1 | 10/2014 | Lapidus et al. |
| 2015/0005176 A1 | 1/2015 | Kim et al. |
| 2015/0100244 A1 | 4/2015 | Hannum |
| 2015/0347676 A1 | 12/2015 | Zhao et al. |
| 2016/0034640 A1 | 2/2016 | Zhao et al. |
| 2016/0110497 A1 | 4/2016 | Dzakula et al. |
| 2016/0347676 A1 | 12/2016 | Sim et al. |
| 2018/0032665 A1 | 2/2018 | Tang et al. |

FOREIGN PATENT DOCUMENTS

| | | |
|---|---|---|
| WO | 02/42496 A2 | 5/2002 |
| WO | 03/000920 A2 | 1/2003 |
| WO | 03/106620 A2 | 12/2003 |
| WO | 2005/023091 A2 | 3/2005 |
| WO | 2006/056480 A2 | 6/2006 |
| WO | 2007/140417 A2 | 12/2007 |
| WO | 2007/147063 A2 | 12/2007 |
| WO | 2008/121828 A2 | 10/2008 |
| WO | 2009/007743 A1 | 1/2009 |
| WO | 2009/032779 A2 | 3/2009 |
| WO | 2009/032781 A2 | 3/2009 |
| WO | 2009/046445 A1 | 4/2009 |
| WO | 2010/004265 A1 | 1/2010 |
| WO | 2010/033578 A2 | 3/2010 |
| WO | 2010/033639 A2 | 3/2010 |
| WO | 2010/056728 A1 | 5/2010 |
| WO | 2010/059731 A2 | 5/2010 |
| WO | 2010/065470 A2 | 6/2010 |
| WO | 2010/115016 A2 | 10/2010 |
| WO | 2011/034631 A1 | 3/2011 |
| WO | 2011/038327 A1 | 3/2011 |
| WO | 2011/050147 A1 | 4/2011 |
| WO | 2011/057094 A1 | 5/2011 |
| WO | 2011/087760 A2 | 7/2011 |
| WO | 2011/090556 A1 | 7/2011 |
| WO | 2011/090558 A1 | 7/2011 |
| WO | 2011/090559 A1 | 7/2011 |
| WO | 2011/091063 A1 | 7/2011 |
| WO | 2011/102998 A2 | 8/2011 |
| WO | 2011/143659 A2 | 11/2011 |
| WO | 2011/146632 A1 | 11/2011 |
| WO | 2012012703 A2 | 1/2012 |
| WO | 2012/088348 A2 | 6/2012 |
| WO | 2012/088456 A2 | 6/2012 |
| WO | 2012/103031 A2 | 8/2012 |
| WO | 2012/108920 A1 | 8/2012 |
| WO | 2012/118745 A1 | 9/2012 |
| WO | 2012/177792 A2 | 12/2012 |
| WO | 2013/000100 A1 | 1/2013 |
| WO | 2013/052907 A2 | 4/2013 |

(56) References Cited

FOREIGN PATENT DOCUMENTS

| WO | 2013/052913 A2 | 4/2013 |
|---|---|---|
| WO | 2013/055817 A1 | 4/2013 |
| WO | 2013/109981 A1 | 7/2013 |
| WO | 2013/177086 A1 | 11/2013 |
| WO | 2013/192562 A1 | 12/2013 |
| WO | 2014/039556 A1 | 3/2014 |
| WO | 2014/055774 A1 | 4/2014 |
| WO | 2014/055790 A2 | 4/2014 |
| WO | 2014/116598 A2 | 7/2014 |
| WO | 2014/165596 A1 | 10/2014 |
| WO | 2014/190286 A2 | 11/2014 |
| WO | 2015/040591 A1 | 3/2015 |
| WO | 2015/051163 A2 | 4/2015 |
| WO | 2015/054080 A1 | 4/2015 |
| WO | 2015/183872 A1 | 12/2015 |
| WO | 2016/019042 A1 | 2/2016 |

OTHER PUBLICATIONS

International Human Genome Sequencing Consortium Publishes Sequence and Analysis of the Human Genome, Nature, 2001, 406:860-921.
International Preliminary Report on Patentability and Written Opinion mailed on Apr. 24, 2014 in International Application No. PCT/US2012/059592, filed on Oct. 10, 2012, 9 pages.
International Preliminary Report on Patentability and Written Opinion mailed on Jan. 9, 2014 in International Application No. PCT/US2012/043388, filed on Jun. 20, 2012 and published as WO 2012/177792 on Dec. 27, 2012, 8 pages.
International Preliminary Report on Patentability dated Apr. 21, 2016 in PCT/US2014/059156 filed Oct. 3, 2014, 8 pages.
International Preliminary Report on Patentability mailed on Apr. 14, 2016 in International Application No. PCT/US2014/058885, filed on Oct. 2, 2014 and published as WO 2015/051163 on Apr. 9, 2015, 11 pages.
International Preliminary Report on Patentability mailed on Apr. 16, 2015 in International Application No. PCT/US2013/063314, filed on Oct. 3, 2013, 8 pages.
International Preliminary Report on Patentability mailed on Apr. 16, 2015 in International Application No. PCT/US2013/063287, filed Oct. 3, 2013, 9 pages.
International Preliminary Report on Patentability mailed on Aug. 6, 2015 in International Application No. PCT/US2014/012369, filed on Jan. 21, 2014, 8 pages.
International Preliminary Report on Patentability mailed on Dec. 3, 2015 in International Application No. PCT/US2014/039389, filed on May 23, 2014, 12 pages.
International Preliminary Report on Patentability mailed on Dec. 31, 2014 in International Application No. PCT/US2013/047131, filed on Jun. 21, 2013, 9 pages.
International Preliminary Report on Patentability mailed on Feb. 27, 2014 in International Application No. PCT/US2012/059123, filed on Oct. 5, 2012, 3 pages.
International Preliminary Report on Patentability mailed on Jul. 31, 2014 in International Application No. PCT/US2013/022290, filed on Jan. 18, 2013, 9 pages.
International Preliminary Report on Patentability mailed on Jun. 9, 2014 in International Application No. PCT/US2012/059114, filed on Oct. 5, 2012, 5 pages.
International Preliminary Report on Patentability mailed on Oct. 15, 2015 in International Application No. PCT/US2014/032687, filed on Apr. 2, 2014, 10 pages.
International Search Report and Written Opinion dated Jan. 5, 2016 in International Application No. PCT/US2015/042701, filed on Jul. 29, 2015, 20 pages.
International Search Report and Written Opinion dated: Apr. 5, 2013 in International Application No. PCT/US2012/043388 filed: Jun. 20, 2012 and published as: WO 12/177792, filed Dec. 27, 2012, 11 pages.
International Search Report and Written Opinion dated: Mar. 6, 2013 in International Application No. PCT/US2012/059592 filed: Oct. 10, 2012, 14 pages.
International Search Report and Written Opinion dated: Sep. 26, 2012 in International Application No. PCT/US2011/066639 filed: Dec. 21, 2011 and published as: WO 12/088348, filed Jun. 28, 2012, 11 pages.
International Search Report and Written Opinion mailed on Apr. 2, 2014 in International Application No. PCT/US2013/063314, filed on Oct. 3, 2013 and published as WO 2014/055790 on Apr. 10, 2014, 9 pages.
International Search Report and Written Opinion mailed on Dec. 13, 2013 in International Application No. PCT/US2013/063287, filed Oct. 3, 2013, 11 pages.
International Search Report and Written Opinion mailed on Dec. 17, 2014 in International Application No. PCT/US2014/039389, filed on May 23, 2014, 19 pages.
International Search Report and Written Opinion mailed on Feb. 18, 2015 in International Application No. PCT/US2014/058885, filed on Oct. 2, 2014, 11 pages.
International Search Report and Written Opinion mailed on Jul. 14, 2014 in International Application No. PCT/US2014/032687, filed on Apr. 2, 2014, 13 pages.
International Search Report and Written Opinion mailed on Jul. 4, 2013 in International Application No. PCT/US2013/022290 filed: Jan. 18, 2013 and published as: WO/2013/109981 on Jul. 25, 2013, 13 pages.
International Search Report and Written Opinion mailed on May 9, 2014 in International Application No. PCT/US2014/012369, filed Jan. 21, 2014, 10 pages.
International Search Report and Written Opinion mailed on Oct. 2, 2015 in International Patent Application No. PCT/US2015/032550, filed on May 27, 2015, 12 pages.
International Search Report and Written Opinion mailed on Sep. 18, 2013 in International Application No. PCT/US2013/047131, filed on Jun. 21, 2013 and published as WO 2013/192562 on Dec. 27, 2013, 11 pages.
International Search Report and Written Opinion mailed on Sep. 24, 2014 in International Application No. PCT/US2014/043497, filed on Jun. 20, 2014 and published as WO 2014/205401 on Dec. 24, 2014, 9 pages.
International Search Report and Written Opinion mailed on Sep. 9, 2013 in International Application No. PCT/US2012/059114, filed on Oct. 5, 2012 and published as WO/2013/052907 on Apr. 11, 2013, 14 pages.
International Search Report and Written Opinion mailed on Sep. 9, 2013 in International Application No. PCT/US2012/059123, filed on Oct. 5, 2012 and published as WO/2013/052913 on Apr. 11, 2013, 16 pages.
International Search Report and Written Opinion of the international Searching Authority for International Application No. PCT/US11/24132, mailed Aug. 8, 2011, 15 pages.
Invitation to Pay Additional Fees and Partial International Search Report dated Oct. 14, 2015 in International Application No. PCT/US2015/042701, filed on Jul. 29, 2015.
Invitation to Pay Additional Fees and Partial Search Report dated: Jan. 18, 2013 in International Application No. PCT/US2012/059592 filed: Oct. 10, 2012, 10 pages.
Invitation to Pay Additional Fees and Partial Search Report dated: Jul. 3, 2013 in International Application No. PCT/US2012/059123 filed: Oct. 5, 2012 and published as: WO/2013/052913 on Apr. 11, 2013, 7 pages.
Kornberg and Baker, W. H. Freeman, New York, 1991.
National Human Genome Research Institute: Chromosomes Fact Sheet, downloaded from web http://www.genome.gov/26524120, downloaded Sep. 9, 2015, 3 pages.
Office Action dated Apr. 14, 2017 in U.S. Appl. No. 14/127,912, filed Apr. 7, 2014 and published as US 2014-0235474 on Aug. 21, 2014, Apr. 14, 2017, 10 pages.
Office Action dated Apr. 16, 2015 in U.S. Appl. No. 13/669,136, filed Nov. 5, 2012 and published as US 2013-0085681 on Apr. 4, 2013, 8 pages.

(56) References Cited

OTHER PUBLICATIONS

Office Action dated Apr. 16, 2015 in U.S. Appl. No. 13/933,935, filed Jul. 2, 2013 and published as US 2013-0304392 on Nov. 14, 2013, 9 pages.
Office Action dated Apr. 17, 2015 in U.S. Appl. No. 13/829,164, filed Mar. 14, 2013 and published as US 2013-0288244 on Oct. 31, 2014, 9 pages.
Office Action dated Apr. 21, 2015 in U.S. Appl. No. 13/754,817, filed Jan. 30, 2013 and published as US 2013-0150253 on Jun. 13, 2013, 7 pages.
Office Action dated Apr. 26, 2016 in U.S. Appl. No. 13/797,508, filed Mar. 12, 2013 and published as US 2013-0261983 on Oct. 3, 2013, 12 pages.
Office Action dated Apr. 27, 2016 in U.S. Appl. No. 13/829,164, filed Mar. 14, 2013 and published as US 2013-0288244 on Oct. 31, 2014, 9 pages.
Office Action dated Apr. 27, 2016 in U.S. Appl. No. 13/933,935, filed Jul. 2, 2013 and published as US 2013-0304392 on Nov. 14, 2013, 9 pages.
Office Action dated Apr. 7, 2014 in U.S. Appl. No. 13/754,817, filed Jan. 30, 2013 and published as US 2013-0150253 on Jun. 13, 2013, 33 pages.
Office Action dated Aug. 13, 2014 in U.S. Appl. No. 13/669,136, filed Nov. 5, 2012 and published as US 2013-0085681 on Apr. 4, 2013, 7 pages.
Office Action dated Aug. 13, 2014 in U.S. Appl. No. 13/829,164, filed Mar. 14, 2013 and published as US 2013-0288244 on Oct. 31, 2014, 12 pages.
Office Action dated Aug. 14, 2014 in U.S. Appl. No. 13/933,935, filed Jul. 2, 2013 and published as US 2013-0304392 on Nov. 14, 2013, 12 pages.
Office Action dated Aug. 22, 2013 in U.S. Appl. No. 13/797,508, filed Mar. 12, 2013 and published as US 2013-0261983 on Oct. 3, 2013, 17 pages.
Office Action dated Aug. 27, 2015 in U.S. Appl. No. 13/933,935, filed Jul. 2, 2013 and published as US 2013-0304392 on Nov. 14, 2013, 12 pages.
Office Action dated Dec. 24, 2020 in U.S. Appl. No. 15/647,171, filed Jul. 11, 2017 and published as US-2018-0032665-A1 on Feb. 1, 2018, 11 pages.
Office Action dated Dec. 26, 2013 in U.S. Appl. No. 13/797,508, filed Mar. 12, 2013 and published as US 2013-0261983 on Oct. 3, 2013, 9 pages.
Office Action dated Feb. 1, 2016 in U.S. Appl. No. 13/669,136, filed Nov. 5, 2012 and published as US 2013-0085681 on Apr. 4, 2013, 14 pages.
Office Action dated Feb. 12, 2016 in U.S. Appl. No. 13/797,930, filed Mar. 12, 2013 and published as US 2013-0325360 on Dec. 5, 2013, 17 pages.
Office Action dated Feb. 20, 2013 in U.S. Appl. No. 13/656,328, filed Oct. 19, 2012, not yet published, 13 pages.
Office Action dated Feb. 23, 2016 in U.S. Appl. No. 14/812,432, filed Jul. 29, 2015 and published as US 2016-0034640 on Feb. 4, 2016, 33 pages.
Office Action dated Jan. 17, 2014 in U.S. Appl. No. 13/333,842, filed Dec. 21, 2011 and published as US 2012/0184449 on Jul. 19, 2012, 19 pages.
Office Action dated Jan. 27, 2014 in U.S. Appl. No. 13/829,164, filed Mar. 14, 2013 and published as US 2013-0288244 on Oct. 31, 2014, 9 pages.
Office Action dated Jan. 30, 2014 in U.S. Appl. No. 13/933,935, filed Jul. 2, 2013 and published as US 2013-0304392 on Nov. 14, 2013, 6 pages.
Office Action dated Jul. 27, 2015 in U.S. Appl. No. 13/782,857, filed Mar. 1, 2013 and published as US 2013-0310260 on Nov. 21, 2013, 14 pages.
Office Action dated Jul. 28, 2014 in U.S. Appl. No. 13/797,508, filed Mar. 12, 2013 and published as US 2013-0261983 on Oct. 3, 2013, 7 pages.
Office Action dated Mar. 11, 2016 in U.S. Appl. No. 13/782,857, filed Mar. 1, 2013 and published as US 2013-0310260 on Nov. 21, 2013, 15 pages.
Office Action dated Mar. 19, 2015 in U.S. Appl. No. 13/797,508, filed Mar. 12, 2013 and published as US 2013-0261983 on Oct. 3, 2013, 10 pages.
Office Action dated Mar. 22, 2016 in U.S. Appl. No. 12/727,824, filed Mar. 19, 2010 and published as US 2010-0216153 on Aug. 26, 2010, 68 pages.
Office Action dated Mar. 3, 2016 in U.S. Appl. No. 13/829,373, filed Mar. 14, 2013 and published as US 2013-0338933 on Dec. 19, 2013, 13 pages.
Office Action dated May 12, 2015 in U.S. Appl. No. 13/669,136, filed Nov. 5, 2012 and published as US 2013-0085681 on Apr. 4, 2013, 9 pages.
Office Action dated May 13, 2015 in U.S. Appl. No. 13/333,842, filed Dec. 21, 2011 and published as US 2012/0184449 on Jul. 19, 2012, 20 pages.
Office Action dated May 25, 2016 in U.S. Appl. No. 14/187,876, filed Feb. 24, 2014 and published as US 2014-0322709 on Oct. 30, 2014, 21 pages.
Office Action dated May 29, 2015 in U.S. Appl. No. 14/187,876, filed Feb. 24, 2014 and published as US 2014-0322709 on Oct. 30, 2014, 43 pages.
Office Action dated May 3, 2013 in U.S. Appl. No. 13/333,842, filed Dec. 21, 2011 and published as 2012/0184449 on: Jul. 19, 2012, 19 pages.
Office Action dated May 7, 2013 in U.S. Appl. No. 13/754,817, filed Jan. 30, 2013 and published as US 2013-0150253 on Jun. 13, 2013, 15 pages.
Office Action dated Nov. 30, 2016 in U.S. Appl. No. 14/127,912, filed Apr. 7, 2014 and published as US 2014-0235474 on Aug. 21, 2014, 10 pages.
Office Action dated Oct. 16, 2013 in U.S. Appl. No. 13/933,935, filed Jul. 2, 2013 and published as US 2013-0304392 on Nov. 14, 2013, 11 pages.
Office Action dated Oct. 17, 2013 in U.S. Appl. No. 13/669,136, filed Nov. 5, 2012 and published as US 2013-0085681 on Apr. 4, 2013, 9 pages.
Office Action dated Oct. 18, 2013 in U.S. Appl. No. 13/656,328, filed Oct. 19, 2012 and published as US 2013-0103320 on Apr. 25, 2013, 11 pages.
Office Action dated Oct. 2, 2015 in U.S. Appl. No. 13/754,817, filed Jan. 30, 2013 and published as US 2013-0150253 on Jun. 13, 2013, 11 pages.
Office Action dated Oct. 2, 2015 in U.S. Appl. No. 13/782,883, filed Mar. 1, 2013 and published as US 2014-0180594 on Jun. 26, 2014, 14 pages.
Office Action dated Oct. 22, 2015 in U.S. Appl. No. 13/781,530, filed Feb. 28, 2013 and published as US 2014-0100792 on Apr. 10, 2014, 14 pages.
Office Action dated Oct. 27, 2015 in U.S. Appl. No. 13/333,842, filed Dec. 21, 2011 and published as US 2012/0184449 on Jul. 19, 2012, 27 pages.
Office Action dated Oct. 6, 2014 in U.S. Appl. No. 13/754,817, filed Jan. 30, 2013 and published as US 2013-0150253 on Jun. 13, 2013, 12 pages.
Office Action dated Sep. 1, 2015 in U.S. Appl. No. 13/829,164, filed Mar. 14, 2013 and published as US 2013-0288244 on Oct. 31, 2014, 10 pages.
Office Action dated Sep. 11, 2013 in U.S. Appl. No. 13/829,164, filed Mar. 14, 2013 and published as US 2013-0288244 on Oct. 31, 2013, 15 pages.
Office Action dated Sep. 12, 2013 in U.S. Appl. No. 13/656,328, filed Oct. 19, 2012 and published as US 2013-0103320 on Apr. 25, 2013, 11 pages.
Office Action dated Sep. 12, 2013 in U.S. Appl. No. 13/669,136, filed Nov. 5, 2012 and published as: US 2013-0085681 on Apr. 4, 2013, 10 pages.
Office Action dated Sep. 14, 2020 in U.S. Appl. No. 15/647,171, filed Jul. 11, 2017 and published as US-2018-0032665-A1 on Feb. 1, 2018, 9 pages.

(56) References Cited

OTHER PUBLICATIONS

Office Action dated Sep. 18, 2015 in U.S. Appl. No. 12/727,824, filed Mar. 19, 2010 and published as US 2010-0216153 on Aug. 26, 2010, 44 pages.
Office Action dated Sep. 22, 2015 in U.S. Appl. No. 13/779,638, filed Feb. 27, 2013 and published as US 2013-0309666 on Nov. 21, 2013, 11 pages.
Office Action dated Sep. 28, 2015 in U.S. Appl. No. 14/187,876, filed Feb. 24, 2014 and published as US 2014-0322709 on Oct. 30, 2014, 55 pages.
Office Action dated Sep. 8, 2015 in U.S. Appl. No. 13/669,136, filed Nov. 5, 2012 and published as US 2013-0085681 on Apr. 4, 2013, 9 pages.
Office Action dated Sep. 8, 2015 in U.S. Appl. No. 13/797,508, filed Mar. 12, 2013 and published as US 2013-0261983 on Oct. 3, 2013, 9 pages.
Office Action dated: Aug. 22, 2013 in U.S. Appl. No. 13/619,039, filed Sep. 14, 2012 and published as: US 2013/0022977 on: Jan. 24, 2013, 13 pages.
Office Action dated: Feb. 15, 2013 in U.S. Appl. No. 13/669,136, filed Nov. 5, 2012 and published as: US 2013-0085681 on Apr. 4, 2013, 13 pages.
Office Action dated: Feb. 25, 2015 in U.S. Appl. No. 12/727,824, filed Sep. 13, 2012 and published as: US 2010/0216153 on: Aug. 26, 2010, 28 pages.
Office Action dated: Jan. 10, 2013 in U.S. Appl. No. 13/619,039, filed Sep. 14, 2012 and published as: US 2013/0022977 on: Jan. 24, 2013, 21 pages.
Office Action dated: Jul. 14, 2014 in U.S. Appl. No. 12/727,824, filed Sep. 13, 2012 and published as: US 2010/0216153 on: Aug. 26, 2010, 25 pages.
Office Action dated: May 16, 2011 in U.S. Appl. No. 12/727,824, filed Sep. 13, 2012 and published as: US 2010/0216153 on: Aug. 26, 2010, 11 pages.
Office Action dated: Oct. 18, 2011 in U.S. Appl. No. 12/727,824, filed Sep. 13, 2012 and published as: US 2010/0216153 on: Aug. 26, 2010, 11 pages.
Adinolfi et al., "Rapid Detection of Aneuploidies by Microsatellite and the Quantitative Fluorescent Polymerase Chain Reaction", Prenatal Diagnosis, 1997, 17(13):1299-1311.
Agarwal et al., "Commercial Landscape of Noninvasive Prenatal Testing in the United States", Prenatal Diagnosis, Jun. 2013, 33(6):521-531.
Akeson et al., "Microsecond Time-Scale Discrimination Among Polycytidylic Acid, Polyadenylic Acid, and Polyuridylic Acid as Homopolymers or as Segments Within Single RNA Molecules", Biophysical Journal, Dec. 1999, 77:3227-3233.
Alkan et al., "Personalized Copy Number and Segmental Duplication Maps Using Next-Generation Sequencing", Nature Genetics, Oct. 30, 2009, 41(10):1061-1067.
Amicucci et al., "Prenatal Diagnosis of Myotonic Dystrophy Using Fetal DNA Obtained from Maternal Plasma", Clinical Chemistry, 2000, 46:301-302.
Anantha et al., "Porphyrin Binding to Quadruplexed T4G4", Biochemistry, 1998, 37(9):2709-2714.
Armour et al., "Measurement of Locus Copy Number by Hybridisation with Amplifiable Probes", Nucleic Acids Research, Jan. 2000, 28(2):605-609.
Armour et al., "The Detection of Large Deletions or Duplications in Genomic DNA", Human Mutation, Nov. 2002, 20(5):325-337.
Ashkenasy et al., "Recognizing a Single Base in an Individual DNA Strand: A Step Toward Nanopore DNA Sequencing", Angewandte Chemie (International ed. in English), Feb. 18, 2005, 44(9):1401-1404.
Ashoor et al., "Chromosome-Selective Sequencing of Maternal Plasma Cell-free DNA for First-Trimester Detection of Trisomy 21 and Trisomy 18", American Journal of Obstetrics and Gynecology, Apr. 2012, 206(4):322.e1-322.e5.
Aston et al., "Optical Mapping and Its Potential for Large-Scale Sequencing Projects", Trends in Biotechnology, Jul. 1999, 17(7):297-302.
Aston et al., "Optical Mapping: An Approach for Fine Mapping", Methods in Enzymology, 1999, 303:55-73.
Avent et al., "Non-Invasive Diagnosis of Fetal Sex; Utilisation of Free Fetal DNA in Maternal Plasma and Ultrasound", Prenatal Diagnosis, Jul. 2006, 26(7):598-603.
Avent "Refining Noninvasive Prenatal Diagnosis with Single-Molecule Next-Generation Sequencing", Clinical Chemistry, Apr. 2012, 58(4):657-658.
Beaucage et al., "Deoxynucleoside Phosphoramidites—A New Class of Key Intermediates for Deoxypolynucleotide Synthesis", Tetrahedron Letters, 1981, 22(20):1859-1862.
Benjamini et al., "Summarizing and Correcting the GC Content Bias in High-Throughput Sequencing", Nucleic Acids Research, XP0551 62924, ISSN: 0305-1048, DOI: 10.1093/nar/gks001, Feb. 9, 2012, 40(10):14 pages.
Berger et al., "Universal Bases for Hybridization, Replication, and Chain Termination", Nucleic Acids Research, 2000, 28(15):2911-2914.
Bergstrom et al., "Synthesis, Structure, and Deoxyribonucleic Acid Sequencing with a Universal Nucleoside: 1-(2'-Deoxy-β-D-Ribofuranosyl)-2-Nitropyrrole", Journal of the American Chemistry Society, 1995, 117:1201-1209.
Bianchi et al., "Isolation of Fetal DNA from Nucleated Erythrocytes in Maternal Blood", PNAS, 1990, 87(9):3279-3283.
Boeva et al., "Control-Free Calling of Copy Number Alterations in Deep-Sequencing Data Using GC-Content Normalization", Bioinformatics, 2011, 27(2):268-269.
Bollen "Bioconductor: Microarray Versus Next-Generation Sequencing Toolsets", Utrecht University, Feb. 11, 2014, 14 pages.
Borsenberger et al., "Chemically Labeled Nucleotides and Oligonucleotides Encode DNA for Sensing with Nanopores", Journal of the American Chemical Society, 2009, 131:7530-7531.
Branton et al., "The Potential and Challenges of Nanopore Sequencing", Nature Biotechnology, 2008, 26:1146-1153.
Braslavsky et al., "Sequence Information Can Be Obtained from Single DNA Molecules", PNAS, Jan. 25, 2003, 100(7):3960-3964.
Brizot et al., "Maternal Serum hCG and Fetal Nuchal Translucency Thickness for the Prediction of Fetal Trisomies in the First Trimester of Pregnancy", British Journal of Obstetrices and Gynaecology, 1995, 102(2):127-132.
Brizot et al., "Maternal Serum Pregnancy-Associated Plasma Protein a and Fetal Nuchal Translucency Thickness for the Prediction of Fetal Trisomies in Early Pregnancy", Obstetrics & Gynecology, Dec. 1994, 84(6):918-922.
Brown et al., "Synthesis and Duplex Stability of Oligonucleotides Containing Adenine-Guanine Analogues", Carbohydrate Research, 1991, 216:129-139.
Brown et al., "Validation of QF-PCR for Prenatal Aneuploidy Screening in the United States", Prenatal Diagnosis, 2006, 26(11):1068-1074.
Brown "A Step-by-Step Guide to Non-Linear Regression Analysis of Experimental Data Using a Microsoft Excel Spreadsheet Computer Methods and Programs in Biomedicine", Computer Methods and Programs in Biomedicine, Jun. 2001, 65(3):191-200.
Bruch et al., "Trophoblast-like Cells Sorted from Peripheral Maternal Blood Using Flow Cytometry: A Multiparametric Study Involving Transmission Electron Microscopy and Fetal DNA Amplification", Prenatal Diagnosis, 1991, 11:787-798.
Brunger "Free R Value: A Novel Statistical Quantity for Assessing the Accuracy of Crystal Structures", Nature, Jan. 30, 1992, 355:472-475.
Bullard et al., "Evaluation of Statistical Methods for Normalization and Differential Expression in mRNA-Seq Experiments", BMC Bioinformatics, 2010, 11(94):1-13.
Burlingame "Mass Spectrometry", Analytical Chemistry, 1998, 70(16):647R-716R.
Campbell et al., "Identification of Somatically Acquired Rearrangements in Cancer Using Genome-Wide Massively Parallel Paired-End Sequencing", Nature Genetics, Jun. 2008, 40(6):722-729.

(56) References Cited

OTHER PUBLICATIONS

Canick et al., "A New Prenatal Blood Test for down Syndrome (RNA)", Women and Infants Hospital of Rhode Island, Apr. 6, 2009, 3 pages.
Canick et al., "DNA Sequencing of Maternal Plasma to Identify down Syndrome and Other Trisomies in Multiple Gestations", Prenatal Diagnosis, May 14, 2012, 14:730-734.
Canick et al., "The Impact of Maternal Plasma DNA Fetal Fraction on next Generation Sequencing Tests for Common Fetal Aneuploidies", Prenatal Diagnosis, 2013, 33:667-674.
Cann et al., "A Heterodimeric DNA Polymerase: Evidence That Members of Euryarchaeota Possess a Distinct DNA Polymerase", PNAS, 1998, 95:14250-14255.
Cariello et al., "Fidelity of Thermococcus Litoralis DNA Polymerase (Vent) in PCR Determined by Denaturing Gradient Gel Electrophoresis", Nucleic Acids Research, Aug. 11, 1991, 19(15):4193-4198.
Carlson et al., "Molecular Definition of 22q11 Deletions in 151 Velo-Cardio-Facial Syndrome Patients", The American Journal of Human Genetics, Sep. 1, 1997, 61(3):620-629.
Chan et al., "Size Distributions of Maternal and Fetal DNA in Maternal Plasma", Clinical Chemistry, 2004, 50(1):88-92.
Chandrananda et al., "Investigating and Correcting Plasma DNA Sequencing Coverage Bias to Enhance Aneuploidy Discovery", PLoS One, Jan. 2014, 9:14 pages.
Chen et al., "A Method for Noninvasive Detection of Fetal Large Deletions/Duplications by Low Coverage Massively Parallel Sequencing", Prenatal Diagnosis, Supp pp. 1-6, 2013, 33(6):584-590.
Chen et al., "Noninvasive Prenatal Diagnosis of Fetal Trisomy 18 and Trisomy 13 by Maternal Plasma DNA Sequencing", PLoS One, Jul. 6, 2011, 6(7):7 pages.
Chiang et al., "High-Resolution Mapping of Copy-Number Alterations with Massively Parallel Sequencing", Nature Methods, Jan. 2009, 6(1):99-103.
Chien et al., "Deoxyribonucleic Acid Polymerase from the Extreme Thermophile *Thermus aquaticus*", Journal of Bacteriology, 1976, 127:1550-1557.
Chim et al., "Systematic Search for Placental DNA-Methylation Markers on Chromosome 21: Toward a Maternal Plasma-Based Epigenetic Test for Fetal Trisomy 21", Clinical Chemistry, 2008, 54(3):500-511.
Chiu et al., "Maternal Plasma DNA Analysis with Massively Parallel Sequencing by Ligation for Noninvasive Prenatal Diagnosis of Trisomy 21", Clinical Chemistry, 2010, 56(3):459-463.
Chiu et al., "Non-Invasive Prenatal Assessment of Trisomy 21 by Multiplexed Maternal Plasma DNA Sequencing: Large Scale Validity Study", British Medical Journal, C7401 Web Appendices, Jan. 11, 2011, 342:17 pages.
Chiu et al., "Noninvasive Prenatal Diagnosis of Fetal Chromosomal Aneuploidy by Massively Parallel Genomic Sequencing of DNA in Maternal Plasma", Proceedings of the National Academy of Sciences USA, Dec. 10, 2008, 105(51):20458-20463.
Chiu et al., "Prenatal Exclusion of β Thalassemia Major by Examination of Maternal Plasma", The Lancet, 2002, 360:998-1000.
Chu et al., "Statistical Model for Whole Genome Sequencing and Its Application to Minimally Invasive Diagnosis of Fetal Genetic Disease", Bioinformatics, Mar. 23, 2009, 25(10):1244-1250.
Chung et al., "Discovering Transcription Factor Binding Sites in Highly Repetitive Regions of Genomes with Multi-Read Analysis of ChIP-Seq Data", PLoS Computational Biology, Jul. 2011, 7(7):17 pages.
Cohen et al., "GC Composition of the Human Genome: In Search of Isochores", Molecular Biological Evolution, 2005, 22(5):1260-1272.
Cooper et al., "Human Genome Mutations", BIOS Publishers, 1993.
Costa et al., "Fetal RHD Genotyping in Maternal Serum During the First Trimester of Pregnancy", British Journal of Haematology, 2002, 119:255-260.
Costa et al., "New Strategy for Prenatal Diagnosis of X-Linked Disorders", The New England journal of medicine, 2002, 346:1502.

Cunningham et al., "Williams Obstetrics", McGraw-Hill, 2002, 1 page.
D'Alton "Prenatal Diagnostic Procedures", Seminars in Perinatology, Jun. 1994, 18(3):140-162.
Dan et al., "Prenatal Detection of Aneuploidy and Imbalanced Chromosomal Arrangements by Massively Parallel Sequencing", PLoS One, 2012, 7(2):7 pages.
Datasheet "Illumina Sequencing: TruSeq RNA and DNA Sample Preparation Kits v2", Publication No. 970-2009-039, Apr. 27, 2011, 4 pages.
Davanos et al., "Relative Quantitation of Cell-Free Fetal DNA in Maternal Plasma Using Autosomal DNA Markers", Clinica Chimica Acta, Aug. 1, 2011, 412(17-18):1539-1543.
Deamer et al., "Nanopores and Nucleic Acids: Prospects for Ultrarapid Sequencing", Trends in Biotechnology, Apr. 2000, 18(4):147-151.
Derrien et al., "Fast Computation and Applications of Genome Mappability", PLoS One, Jan. 19, 2012, 7(1):16 pages.
Dhallan et al., "Methods to Increase the Percentage of Free Fetal DNA Recovered from Maternal Circulation", JAMA: The Journal of the American Medical Association, Mar. 1, 2004, 291(9):1114-1119.
Diaz et al., "Accuracy of Replication in the Polymerase Chain Reaction. Comparison Between Thermotoga Maritima DNA Polymerase and Thermus Aquaticus DNA Polymerase", Brazilian Journal of Medical and Biological Research, 1998, 31:1239-1242.
Ding et al., "A High-Throughput Gene Expression Analysis Technique Using Competitive PCR and Matrix-Assisted Laser Desorption Ionization Time-of-Flight MS", Proceedings of the National Academy of Sciences, Mar. 18, 2003, 100(6):3059-3064.
Dohm et al., "Substantial Biases in Ultra-Short Read Data Sets from High-Throughput DNA Sequencing", Nucleic Acids Research, Aug. 1, 2008, 36(16):10 pages.
Donoho et al., "WaveLab and Reproducible Research", Stanford University, Stanford CA 94305, USA, 1995, 27 pages.
Drmanac et al., "Sequencing by Hybridization: Towards an Automated Sequencing of One Million M13 Clones Arrayed on Membranes", Electrophoresis, 1992, 13(8):566-573.
Edelmann et al., "A Common Molecular Basis for Rearrangement Disorders on Chromosome 22q11", Human Molecular Genetics, Jul. 1999, 8(7):1157-1167.
Egger et al., "Reverse Transcription Multiplex PCR for Differentiation Between Polio- and Enteroviruses from Clinical and Environmental Samples", Journal of Clinical Microbiology, Jun. 1995, 33(6):1442-1447.
Ehrich et al., "Noninvasive Detection of Fetal Trisomy 21 by Sequencing of DNA in Maternal Blood: A Study in a Clinical Setting", American Journal of Obstetrics and Gynecology, Mar. 2011, 204(3):205e1-205e11.
Eiben et al., "First-Trimester Screening: An Overview", Journal of Histochemistry & Cytochemistry, Mar. 2005, 53(3):281-283.
Ensenauer et al., "Microduplication 22q11.2, an Emerging Syndrome: Clinical, Cytogenetic, and Molecular Analysis of Thirteen Patients", American Journal of Human Genetics, 2003, 73(5):1027-1040.
Epicenter "Product Sheet For: Nextera™ DNA Sample Prep Kit (Illumina®-Compatible) Cat. Nos. GA09115, GA091120, GA0911-50, GA0911-96, and GABC0950", Epicentre, an Illumina Company, Literature# 307, Jun. 2011, 12 pages.
Fan et al., "Analysis of the Size Distributions of Fetal and Maternal Cell-Free DNA by Paired-End Sequencing", Clinical Chemistry, 2010, 56(8):1279-1286.
Fan et al., "Noninvasive Diagnosis of Fetal Aneuploidy by Shotgun Sequencing DNA from Maternal Blood", The National Academy of Sciences of the USA, Oct. 21, 2008, 105(42):16266-16271.
Fan et al., "Sensitivity of Noninvasive Prenatal Detection of Fetal Aneuploidy from Maternal Plasma Using Shotgun Sequencing Is Limited Only by Counting Statistics", PLoS One, May 3, 2010, 5(5):7 pages.
Forabosco et al., "Incidence of Non-Age-Dependent Chromosomal Abnormalities: A Population-Based Study on 88965 Amniocenteses", European Journal of Human Genetics, Jan. 2009, 17(7):897-903.

(56) References Cited

OTHER PUBLICATIONS

Gebhard et al., "Genome-Wide Profiling of CpG Methylation Identifies Novel Targets of Aberrant Hypermethylation in Myeloid Leukemia", Cancer Research, Jun. 2006, 66(12):6118-6128.
Goya et al., "SNVMix: Predicting Single Nucleotide Variants From Next-Generation Sequencing of Tumors", Bioinformatics, 2010, 26(6):730-736.
Grati F. R. "Chromosomal Mosaicism in Human Feto-Placental Development: Implications for Prenatal Diagnosis", Journal of Clinical Medicine, Jul. 24, 2014, 3(3):809-837.
Haar "On the Theory of Orthogonal Function Systems", Mathematische Annalen, 1910, 69(3):331-371.
Hahn et al., "Cell-Free Nucleic Acids as Potential Markers for Preeclampsia", Placenta, Feb. 2011, 32(1):S17-S20.
Harris et al., "Single-Molecule DNA Sequencing of a Viral Genome", Science, Apr. 4, 2008, 320:106-109.
Herzenberg et al., "Fetal Cells in the Blood of Pregnant Women: Detection and Enrichment by Fluorescence-Activated Cell Sorting", PNAS, 1979, 76:1453-1455.
Hill "Gen-Probe Transcription-Mediated Amplification: System Principles", http://www.gen-probe.com/pdfs/tma_whiteppr.pdf, Jan. 1996, 4 pages.
Hinds et al., "Whole-Genome Patterns of Common DNA Variation in Three Human Populations", Science, Feb. 18, 2005, 307(5712):1072-1079.
Hinnisdaels et al., "Direct Cloning of PCR Products Amplified with Pwo DNA Polymerase", Biotechniques, 20:186-188.
Hsu et al., "A Model-Based Circular Binary Segmentation Algorithm for the Analysis of Array CGH Data", BMC Research Notes, Oct. 10, 2011, 4(394):12 pages.
Hsu et al., "Denoising Array-Based Comparative Genomic Hybridization Data Using Wavelets", Biostatistics, Apr. 2005, 6(2):211-226.
Huber et al., "High-Resolution Liquid Chromatography of DNA Fragments on Non-Porous Poly(styrene-Divinylbenzene) Particles", Nucleic Acids Research, 1993, 21(5):1061-1066.
Hudecova et al., "Maternal Plasma Fetal DNA Fractions in Pregnancies with Low and High Risks for Fetal Chromosomal Aneuploidies", PLoS One, 2014, 9(2):7 pages.
Hudson et al., "An STS-Based Map of the Human Genome", Science, Dec. 1995, 270(5244):1945-1954.
Hulten et al., "Rapid and Simple Prenatal Diagnosis of Common Chromosome Disorders: Advantages and Disadvantages of the Molecular Methods FISH and QF-PCR.", Reproduction, Sep. 2003, 126(3):279-297.
Hupe et al., "Analysis of Array CGH Data: From Signal Ratio to Gain and Loss of DNA Regions", Bioinformatics, 2004, 20(18):3413-3422.
Huse et al., "Accuracy and Quality of Massively Parallel DNA Pyrosequencing", Genome Biology, 2007, 8(7):R143.
Innis et al., "PCR Protocols: A Guide to Methods and Applications", 1990, 7 pages.
James James, "Mathematics Dictionary", Chapman & Hall, International Thomson Publishing, 5 Edition, 1992, 5 pages.
Jensen et al., "Detection of Microdeletion 22q11.2 in a Fetus by Next-Generation Sequencing of Maternal Plasma", Clinical Chemistry, Jul. 2012, 58(7):1148-1151.
Jensen et al., "High-Throughput Massively Parallel Sequencing for Fetal Aneuploidy Detection from Maternal Plasma", PLoS One, Mar. 6, 2013, 8(3):8 pages.
Jiang et al., "FetalQuant: Deducing Fractional Fetal DNA Concentration from Massively Parallel Sequencing of DNA in Maternal Plasma", Bioinformatics, Nov. 15, 2012, 28(22):2883-2890.
Jing et al., "Automated High Resolution Optical Mapping Using Arrayed, Fluid-Fixed DNA Molecules", Proceedings of the National Academy of Sciences, 1998, 95(14):8046-8051.
Johnston et al., "Autoradiography Using Storage Phosphor Technology", Electrophoresis, May 1990, 11(5):355-360.
Joos et al., "Covalent Attachment of Hybridizable Oligonucleotides to Glass Supports", Analytical Biochemistry, 1997, 247:96-101.
Jorgez et al., "Improving Enrichment of Circulating Fetal DNA for Genetic Testing: Size Fractionation Followed by Whole Gene Amplification", Fetal Diagnosis and Therapy, Karger Basel, CH, Jan. 1, 2009, 25(3):314-319.
Juncosa-Ginesta et al., "Improved Efficiency in Site-Directed Mutagenesis by PCR Using a Pyrococcus Sp. GB-D Polymerase", Biotechniques, 1994, 16(5):820-823.
Jurinke et al., "MALDI-TOF Mass Spectrometry: A Versatile Tool for High-Performance DNA Analysis", Molecular Biotechnology, 2004, 26:147-164.
Kalinina et al., "Nanoliter Scale PCR with TaqMan Detection", Nucleic Acids Research, May 15, 1997, 25(10):1999-2004.
Kato et al., "A New Packing for Separation of DNA Restriction Fragments by High Performance Liquid Chromatography", Journal of Biochemistry, 1984, 95(1):83-86.
Khandjian, "UV Crosslinking of RNA to Nylon Membrane Enhances Hybridization Signals", Molecular Biology Reports, 1986, 11:107-115.
Kim et al., "Determination of Fetal DNA Fractions from the Plasma of Pregnant Women Using Sequence Read Counts", Prenatal Diagnosis, 2015, 35(8):810-815.
Kim et al., "Identification of Significant Regional Genetic Variations Using Continuous CNV Values in aCGH Data", Genomics, Nov. 1, 2009, 94(5):317-323.
Kitzman et al., "Noninvasive Whole-Genome Sequencing of a Human Fetus", Science Translation Medicine, American Association for the Advancement of Science, USA, Jun. 2012, 4(137-140):115-122.
Kornberg et al., "DNA Replication", 2nd edition, 1991, 1 page.
Kulkarni et al., "Global DNA Methylation Patterns in Placenta and Its Association with Maternal Hypertension in Pre-Eclampsia", DNA and Cell Biology, Feb. 2011, 30(2):79-84.
Lai et al., "A Shotgun Optical Map of the Entire Plasmodium Falciparium Genome", Nature Genetics, 1999, 23(3):309-313.
Lai et al., "Comparative Analysis of Algorithms for Identifying Amplifications and Deletions in Array CGH Data", Bioinformatics, Oct. 1, 2005, 21(19):3763-3770.
Langmead et al., "Ultrafast and Memory-Efficient Alignment of Short DNA Sequences to the Human Genome", Genome Biology, Article R25, Mar. 4, 2009, 10(3):10 pages.
Lecomte et al., "Selective Inactivation of the 3' to 5' Exonuclease Activity of Escherichia coli DNA Polymerase I by Heat", Nucleic Acids Research, 1983, 11:7505-7515.
Leek et al., "Tackling the Widespread and Critical Impact of Batch Effects in High-Throughput Data", Nature Reviews Genetics, 2010, 11(10):733-739.
Lefkowitz et al., "Clinical Validation of a Noninvasive Prenatal Test for Genomewide Detection of Fetal Copy Number Variants", American Journal of Obstetrics & Gynecology, Aug. 2016, 215(2): 227.e1-227.e16.
Levin "It's Prime Time for Reverse Transcriptase", Cell, 1997, 88(1):5-8.
Li et al., "Detection of Paternally Inherited Fetal Point Mutations for β-Thalassemia Using Size-Fractionated Cell-Free DNA in Maternal Plasma", Journal of the American Medical Association, Feb. 16, 2005, 293:843-849.
Li et al., "Mapping Short DNA Sequencing Reads and Calling Variants Using Mapping Quality Scores", Genome Research, Aug. 19, 2008, 18(11):1851-1858.
Liao et al., "Noninvasive Prenatal Diagnosis of Fetal Trisomy 21 by Allelic Ratio Analysis Using Targeted Massively Parallel Sequencing of Maternal Plasma DNA", PLoS One, 2012, 7(5):7 pages.
Liao et al., "Targeted Massively Parallel Sequencing of Maternal Plasma DNA Permits Efficient and Unbiased Detection of Fetal Alleles", Clinical Chemistry, 2010, 57(1):92-101.
Lin et al., "Synthesis and Duplex Stability of Oligonucleotides Containing Cytosine-Thymine Analogues", Nucleic Acids Research, 1989, 17(24):10373-10383.
Lin et al., "Synthesis of Oligodeoxyribonucleotides Containing Degenerate Bases and Their Use as Primers in the Polymerase Chain Reaction", Nucleic Acids Research, 1992, 20:5149-5152.

(56) References Cited

OTHER PUBLICATIONS

Liu et al., "CUSHAW: A CUDA Compatible Short Read Aligner to Large Genomes Based on the Burrows-Wheeler Transform", Bioinformatics, Jul. 15, 2012, 28(14):1830-1837.
Lo et al., "Digital PCR for the Molecular Detection of Fetal Chromosomal Aneuploidy", PNAS, 2007, 104(32):13116-13121.
Lo et al., "Fetal DNA in Maternal Plasma: Application to Non-Invasive Blood Group Genotyping of the Fetus", Transfusion Clinique et Biologique, 2001, 8:306-310.
Lo et al., "Increased Fetal DNA Concentrations in the Plasma of Pregnant Women Carrying Fetuses with Trisomy 21", Clinical Chemistry, 1999, 45:1747-1751.
Lo et al., "Maternal Plasma DNA Sequencing Reveals the Genome-Wide Genetic and Mutational Profile of the Fetus", Science Translational Medicine, Dec. 8, 2010, 2(61):71 pages.
Lo et al., "Plasma Placental RNA Allelic Ratio Permits Noninvasive Prenatal Chromosomal Aneuploidy Detection", Nature Medicine, 2007, 13(2):218-223.
Lo et al., "Prenatal Diagnosis of Fetal RhD Status by Molecular Analysis of Maternal Plasma", The New England Journal of Medicine, 1998, 339:1734-1738.
Lo et al., "Presence of Fetal DNA in Maternal Plasma and Serum", The Lancet, 1997, 350(9076):485-487.
Lo et al., "Quantative Abnormalities of Fetal NOA in Maternal Serum in Preeclampsia", Clinical Chemistry, 1999, 45:184-188.
Lo et al., "Quantitative Analysis of Fetal DNA in Maternal Plasma and Serum: Implications for Noninvasive Prenatal Diagnosis", American Journal of Human Genetics, Apr. 1, 1998, 62(4):768-775.
Lo et al., "Recent Advances in Fetal Nucleic Acids in Maternal Plasma", Journal of Histochemistry and Cytochemistry, Mar. 2005, 53(3):293-296.
Loakes et al., "5-Nitroindole as an Universal Base Analogue", Nucleic Acids Research, 1994, 22(20):4039-4043.
Lun et al., "Microfluidics Digital PCR Reveals a Higher than Expected Fraction of Fetal DNA in Maternal Plasma", Clinical Chemistry, Oct. 1, 2208, 54(10):1664-1672.
Lundberg et al., "High-Fidelity Amplification Using a Thermostable DNA Polymerase Isolated from Pyrococcus Furiosus", Gene, Dec. 1, 1991, 108:1-6.
Mann et al., "Development and Implementation of a New Rapid Aneuploidy Diagnostic Service Within the UK National Health Service and Implications for the Future of Prenatal Diagnosis", Lancet, Sep. 29, 2001, 358(9287):1057-1061.
Margulies et al., "Genome Sequencing in Microfabricated High-density Picolitre Reactors", Nature, Sep. 15, 2005, 437(7057):376-380.
Mazloom Amin, "Gender Prediction with Bowtie Alignments Using Male Specific Regions", May 10, 2012, 13 pages.
Metzker "Sequencing Technologies—The Next Generation", Nature Review Genetics, Jan. 2010, 11:31-46.
Miller et al., "Consensus Statement: Chromosomal Microarray Is a First-Tier Clinical Diagnostic Test for Individuals with Developmental Disabilities or Congenital Anomalies", American Journal of Human Genetics, 2010, 86(5):749-764.
Mitchell et al., "Chemical Tags Facilitate the Sensing of Individual DNA Strands with Nanopores", Angewandte Chemie International Edition, 2008, 47:5565-5568.
Moudrianakis et al., "Base Sequence Determination in Nucleic Acids with the Electron Microscope, III. Chemistry and Microscopy of Guanine-Labeled DNA", Proceedings of the National Academy of Sciences, 1965, 53:564-571.
Myers et al., "Reverse Transcription and DNA Amplification by a Thermus Thermophilus DNA Polymerase", Biochemistry, Aug. 6, 1991, 30(31):7661-7666.
Nakano et al., "Single-Molecule PCR Using Water-in-Oil Emulsion", Journal of Biotechnology, Apr. 24, 2003, 102(2):117-124.
Nason et al., "Wavelet Methods in Statistics", Table of contents. R. Springer, New York ISBN: 978-0-387-75960-9 (Print) 978-0-387-75961-6 (Online), 2008, 9 pages.
Needham-Vandevanter et al., "Characterization of an Adduct Between CC-1065 and a Defined Oligodeoxynucleotide Duplex", Nucleic Acids Research, 1984, 12(15):6159-6168.
Nevin "Future Direction of Medical Genetics", The Ulster Medical Journal, 2001, 70(1):1-2.
Ng et al., "mRNA of Placental Origin Is Readily Detectable in Maternal Plasma", PNAS, 2003, 100(8):4748-4753.
Ng et al., "The Concentration of Circulating Corticotropin-Releasing Hormone mRNA in Maternal Plasma Is Increased in Preeclampsia", Clinical Chemistry, 2003, 49:727-731.
Nguyen et al., "Denoising of Array-Based DNA Copy Number Data Using the Dual-Tree Complex Wavelet Transform", 2007 IEEE 7th International Symposium on BioInformatics and BioEngineering, Oct. 14, 2007, 137-144.
Nichols et al., "A Universal Nucleoside for Use at Ambiguous Sites in DNA Primers", Nature, 1994, 369(6480):492-493.
Nicolaides et al., "One-Stop Clinic for Assessment of Risk of Chromosomal Defects at 12 Weeks of Gestation", The Journal of Maternal-Fetal & Neonatal Medicine, Jul. 2002, 12(1):9-18.
Nolte "Branched DNA Signal Amplification for Direct Quantitation of Nucleic Acid Sequences in Clinical Specimens", Advanced Clinical Chemistry, 1998, 33:201-235.
Nordstrom et al., "Characterization of Bacteriophage T7 DNA Polymerase Purified to Homogeneity by Antithioredoxin Immunoadsorbent Chromatography", Journal of Biological Chemistry, 1981, 256:3112-3117.
Nygren et al., "Quantification of Fetal DNA by Use of Methylation-Based DNA Discrimination", Clinical Chemistry, Aug. 20, 2010, 56(10):1627-1635.
Oh et al., "CAM: A Web Tool for Combining Array CGH and Microarray Gene Expression Data from Multiple Samples", Computers in Biology and Medicine, Sep. 1, 2010, 40(9):781-785.
Ohno Susumu, "Sex Chromosomes and Sex-Linked Genes", Monographs on Endocrinology (Book 1), 1967, 201 pages.
Old et al., "Candidate Epigenetic Biomarkers for Non-Invasive Prenatal Diagnosis of down Syndrome", Reproductive Biomedicine Online, 2007, 15(2):227-235.
Olshen et al., "Circular Binary Segmentation for the Analysis of Array-Based DNA Copy Number Data", Biostatistics, Oct. 2004, 5(4):557-572.
Omont et al., "Gene-Based Bin Analysis of Genome-Wide Association Studies", BMC Proceedings, 2008, 2(Suppl. 4):S6:9 pages.
Oroskar et al., "Detection of Immobilized Amplicons by ELISA-like Techniques", Clinical Chemistry, 1996, 42:1547-1555.
Oudejans et al., "Detection of Chromosome 21-Encoded mRNA of Placental Origin in Maternal Plasma", Clinical Chemistry, 2003, 49(9):1445-1449.
Palomaki et al., "DNA Sequencing of Maternal Plasma Reliably Identifies Trisomy 18 and Trisomy 13 as Well as down Syndrome: An International Collaborative Study", Genetics in Medicine, 2012, 14(3):296-305.
Palomaki et al., "DNA Sequencing of Maternal Plasma to Detect Down Syndrome: An International Clinical Validation Study", Genetics in Medicine, Nov. 2011, 13(11):913-920.
Pandya et al., "Screening for Fetal Trisomies by Maternal Age and Fetal Nuchal Translucency Thickness at 10 to 14 Weeks of Gestation", BJOG—Obstetrics and Gynecology, Dec. 1995, 102(12):957-962.
Pearson et al., "High-Performance Anion-Exchange Chromatography of Oligonucleotides", Journal of Chromatography, 1983, 255:137-149.
Pekalska et al., "Classifiers for Dissimilarity-Based Pattern Recognition", 15th International Conference on Pattern Recognition (ICPR'00), Barcelona, Spain, Sep. 3-8, 2000, 2:12-16.
Pertl et al., "Rapid Molecular Method for Prenatal Detection of Down's Syndrome", Lancet, May 14, 1994, 343(8907):1197-1198.
Peters et al., "Noninvasive Prenatal Diagnosis of a Fetal Microdeletion Syndrome", Correspondence to the Editor, New England Journal of Medicine, Nov. 10, 2011, 365(19)1847-1848.
Pollack Andrew, "A Less Risky Down Syndrome Test Is Developed", The New York Times, 2011, 5 pages.

(56) References Cited

OTHER PUBLICATIONS

Poon et al., "Differential DNA Methylation Between Fetus and Mother as a Strategy for Detecting Fetal DNA in Maternal Plasma", Clinical Chemistry, Jan. 2002, 48(1):35-41.

Purnell et al., "Discrimination of Single Base Substitutions in a DNA Strand Immobilized in a Biological Nanopore", ACS Nano, 2009, 3:2533-2538.

Pushkarev et al., "Single-Molecule Sequencing of an Individual Human Genome", Nature Biotechnology, 2009, 27(9):847-850.

Qu et al., "Analysis of Drug-DNA Binding Data", Methods Enzymology, 2000, 321:353-369.

Romero et al., "PCR Detection of the Human Enteroviruses", Diagnostic Molecular Microbiology, Principles and Applications, 1993, 401-406.

Romiguier et al., "Contrasting GC-Content Dynamics Across 33 Mammalian Genomes: Relationship with Life-History Traits and Chromosome Sizes", Genome research, 2010, 20:1001-1009.

Ross et al., "The DNA Sequence of the Human X Chromosome", Nature, Mar. 2005, 434(7031):325-337.

Roth et al., "JointSNVMix: A Probabilistic Model for Accurate Detection of Somatic Mutations in Normal/tumour Paired Next-Generation Sequencing Data", Bioinformatics, 2012, 28:907-913.

Saito et al., "Prenatal DNA Diagnosis of a Single-gene Disorder from Maternal Plasma", Lancet, Sep. 30, 2000, 356:1170.

Sambrook et al., "Molecular Cloning: A Laboratory Manual", Molecular Cloning: A Laboratory Manual, 2001, 3(10):52 pages.

Schouten et al., "Relative Quantification of 40 Nucleic Acid Sequences by Multiplex Ligation-Dependent Probe Amplification", Nucleic Acids Research, Jun. 15, 2002, 30(12):13 pages.

Schwinger et al., "Clinical Utility Gene Card For: DiGeorge Syndrome, Velocardiofacial Syndrome, Shprintzen Syndrome, Chromosome 22q11.2 Deletion Syndrome (22q11.2, TBX1)", European Journal of Human Genetics, Feb. 3, 2010, 18:3 pages.

Sehnert et al., "Optimal Detection of Fetal Chromosome Abnormalities by Massively Parallel DNA Sequencing of Cell-Free Fetal DNA from Maternal Blood Clinical Chemistry", Clinical Chemistry, 2011, 57(7):1042-1049.

Sekizawa Akihiko, "Cell-Free Fetal DNA Is Increased in Plasma of Women with Hyperemisis Gravidarum", Clinical Chemistry, 2001, 47:2164-2165.

Shah et al., "Mutational Evolution in a Lobular Breast Tumour Profiled at Single Nucleotide Resolution", Nature, 2009, 461:809-813.

Shen et al., "A Hidden Markov Model for Copy Number Variant Prediction from Whole Genome Resequencing Data", BMC Bioinformatics, 2011, 12(Suppl 6):1-7.

Shendure et al., "Next-Generation DNA Sequencing", Nature Biotechnology, 2008, 26:1135-1145.

Sherman et al., "Epidemiology of Down Syndrome", Mental Retardation and Developmental Disabilities Research Reviews, 2007, 13(3):221-227.

Shin et al., "Prevalence of Down Syndrome Among Children and Adolescents in 10 Regions of the United States", Pediatrics, 2009, 124(6):1565-1571.

Skaletsy et al., "The Male-Specific Region of the Human Y Chromosome Is a Mosaic of Discrete Sequence Classes", Nature, Jun. 19, 2003, 423(6942):825-837.

Slater H.R., "Rapid, High Throughput Prenatal Detection of Aneuploidy Using a Novel Quantitative Method (MLPA)", Journal of Medical Genetics, 2003, 40(12):907-912.

Smid et al., "Evaluation of Different Approaches for Fetal DNA Analysis from Maternal Plasma and Nucleated Blood Cells", Clinical Chemistry, 1999, 45(8):1570-1572.

Smith et al., "Direct Mechanical Measurements of the Elasticity of Single DNA Molecules by Using Magnetic Beads", Science, Nov. 13, 1992, 258(5085):1122-1126.

Snijders et al., "Assembly of Microarrays for Genome-Wide Measurement of DNA Copy Number", Nature Genetics, Nov. 2001, 29(3):263-264.

Snijders et al., "First-Trimester Ultrasound Screening for Chromosomal Defects", Ultrasound in Obstetrics & Gynecology, Mar. 1996, 7(3):216-226.

Snijders et al., "UK Multicentre Project on Assessment of Risk of Trisomy 21 by Maternal Age and Fetal Nuchal-Translucency Thickness at 10-14 Weeks of Gestation.", The Lancet, Fetal Medicine Foundation First Trimester Screening Group, Aug. 1, 1998, 352(9125):343-346.

Soni et al., "Progress Toward Ultrafast DNA Sequencing Using Solid-State Nanopores", Clinical Chemistry, Nov. 2007, 53(11):1996-2001.

Sparks et al., "Noninvasive Prenatal Detection and Selective Analysis of Cell-Free DNA Obtained from Maternal Blood: Evaluation for Trisomy 21 and Trisomy 18", American Journal of Obstetrics and Gynecology, Apr. 2012, 206(4): 319.e1-319.e9.

Sparks et al., "Selective Analysis of Cell-Free DNA in Maternal Blood for Evaluation of Fetal Trisomy", Prenatal Diagnosis, 2012, 32(1):3-9.

Srinivasan et al., "Noninvasive Detection of Fetal Subchromosome Abnormalities via Deep Sequencing of Maternal Plasma", The American Journal of Human Genetics, Feb. 7, 2013, 92(2):167-176.

Stagi et al., "Bone Density and Metabolism in Subjects with Microdeletion of Chromosome 22q11 (del22q11)", European Journal of Endocrinol, 2010, 163(2):329-337.

Stanghellini et al., "Quantitation of Fetal DNA in Maternal Serum During the First Trimester of Pregnancy by the Use of a DAZ Repetitive Probe", Molecular Human Reproduction, 2006, 12(9):587-591.

Stenesh et al., "DNA Polymerase from Mesophilic and Thermophilic Bacteria. III. Lack of Fidelity in the Replication of Synthetic Polydeoxyribonucleotides by DNA Polymerase from Bacillus Licheniformis and Bacillus Stearothermophilus", Biochimica et Biophysica Acta, 1977, 475:32-41.

Stoddart et al., "Single-Nucleotide Discrimination in Immobilized DNA Oligonucleotides with a Biological Nanopore", Proceedings of the National Academy of Sciences, 2009, 106(19):7702-7707.

Strachan T., "The Human Genome", BIOS Scientific Publishers, 1992, 160 pages.

Strauss "Current Protocols in Molecular Biology", John Wiley & Sons, N.Y., 1993, 6.3.1-6.3.6.

Tabor et al., "Randomised Controlled Trial of Genetic Amniocentesis in 4606 Low-Risk Women", Lancet, 1996, 1(8493):1287-1293.

Takagi et al., "Characterization of DNA Polymerase from *Pyrococcus* Sp. Strain KOD1 and Its Application to PCR", Applied and Environmental Microbiology, 1997, 63(11):4504-4510.

Taylor et al., "Characterization of Chemisorbed Monolayers by Surface Potential Measurements", Journal of Physics D, 1991, 24(8):1443-1450.

The International SNP Map, "A Map of Human Genome Sequence Variation Containing 1.42 Million Single Nucleotide Polymorphisms", Nature, 2001, 409:928-933.

Timp et al., "Nanopore Sequencing: Electrical Measurements of the Code of Life", IEEE Transactions on Nanotechnology, 2010, 9(3):281-294.

Trapnell et al., "How to Map Billions of Short Reads onto Genomes", Nature Biotechnology, May 2009, 27(5):455-457.

Van Den Berghe et al., "A New Characteristic Karyotypic Anomaly in Lymphoproliferative Disorders", Cancer, 1979, 44:188-195.

Veltman et al., "High-Throughput Analysis of Subtelomeric Chromosome Rearrangements by Use of Array-Based Comparative Genomic Hybridization", American Journal of Human Genetics, May 2002, 70(5):1269-1276.

Venkatraman et al., "A Faster Circular Binary Segmentation Algorithm for the Analysis of Array CGH Data", Bioinformatics, 2007, 23(6):657-663.

Verbeck et al., "A Fundamental Introduction to Ion Mobility Mass Spectrometry Applied to the Analysis of Biomolecules", Journal of Biomolecular Techniques, 2002, 13(2):56-61.

Verma et al., "Rapid and Simple Prenatal DNA Diagnosis of Down's Syndrome", Lancet, Jul. 4, 1998, 352(9121):9-12.

Verma "The Reverse Transcriptase", Biochimica et Biophysica Acta, Mar. 21, 1977, 473(1):1-38.

(56) References Cited

OTHER PUBLICATIONS

Vincent et al., "Helicase-Dependent Isothermal DNA Amplification", EMBO Reports, 2004, 5(8):795-800.
Voelkerding et al., "Next-generation Sequencing: from Basic Research to Diagnostics", Clinical Chemistry, 2009, 55(4):641-658.
Vogelstein et al., "Digital PCR", Pnas, Aug. 3, 1999, 96(16):9236-9241.
Wang et al., "A Novel Stationary Wavelet Denoising Algorithm for Array-Based DNA Copy Number Data", International Journal of Bioinformatics Research and Applications, 2007, 3(2):206-222.
Wapner et al., "First-Trimester Screening for Trisomies 21 and 18", The New England Journal of Medicine, Oct. 9, 2003, 349(15):1405-1413.
Wavethresh,"Wavelets Statistics and Transforms and a Detailed Description of WaveThresh", <URL:*>http://cran.r-project.org/web/packages/wavethresh/index.html<> <URL:*>http://cran.r-project.org/web/packages/wavethresh/wavethresh.pdf<>, 2013, 396 pages.
Wei et al., "Detection and Quantification by Homogenous PCR of Cell-Free Fetal DNA in Maternal Plasma", Clinical Chemistry, 2001, 47(2):336-338.
Willenbrock et al., "A Comparison Study: Applying Segmentation to Array CGH Data for Downstream Analyses", Bioinformatics, Nov. 15, 2005, 21(22):4084-4091.
Wright et al., "The Use of Cell-Free Fetal Nucleic Acids in Maternal Blood for Non-Invasive Diagnosis", Human Reproduction Update, Jan. 1, 2009, 15(1):139-151.
Wu et al., "Genetic and Environmental Influences on Blood Pressure and Body Mass Index in Han Chinese: A Twin Study", Hypertension Research, Nov. 4, 2010, 34:173-179.
Wu et al., "Reverse Transcriptase", Critical Reviews in Biochemistry and Molecular Biology, Jan. 1975, 3(3):289-347.
Yershov et al., "DNA Analysis and Diagnostics on Oligonucleotide Microchips", PNAS, May 14, 1996, 93(10):4913-4918.
Yoon et al., "Sensitive and Accurate Detection of Copy Number Variants Using Read Depth of Coverage", Genome Research, 2009, 19:1586-1592.
Yu et al., "Noninvasive Prenatal Molecular Karyotyping from Maternal Plasma", PLoS One, 2013, 8(4):e60968:8 pages.
Yu et al., "Size-Based Molecular Diagnostics Using Plasma DNA for Noninvasive Prenatal Testing", Proceedings of the National Academy of Sciences of the United States of America, 2014, 111(23):8583-8588.
Yuk et al., "Genomic Analysis of Fetal Nucleic Acids in Maternal Blood", Annual Review of Genomics and Human Genetics, May 29, 2012, 13(1):285-306.
Zhang et al., "A Single Cell Level Based Method for Copy Number Variation Analysis by Low Coverage Massively Parallel Sequencing", PLoS One, 2013, 8(1):e54236:9 pages.
Zhao et al., "Detection of Fetal Subchromosomal Abnormalities by Sequencing Circulating Cell-Free DNA from Maternal Plasma", Clinical Chemistry, 2015, 61(4):608-616.
Zhao et al., "Quantification and Application of the Placental Epigenetic Signature of the RASSF1A Gene in Maternal Plasma", Prenatal Diagnosis, Aug. 2010, 30(8):778-782.
Zhong et al., "Cell-Free Fetal DNA in the Maternal Circulation Does Not Stem from the Transplacental Passage of Fetal Erythroblasts", Molecular Human Reproduction, 2002, 8(9):864-870.
Zhong et al., "Elevation of Both Maternal and Fetal Extracellular Circulating Deoxyribonucleic Acid Concentrations in the Plasma of Pregnant Women with Preeclampsia", American Journal of Obstetrics and Gynecology, 2001, 184(3):414-419.
ZHOU et al., "Detection of DNA Copy Number Abnormality by Microarray Expression Analysis", Human Genetics, 2004, 114:464-467.
Zhou et al., "Recent Patents of Nanopore DNA Sequencing Technology: Progress and Challenges", Recent Patents on DNA & Gene Sequences, 2010, 4:192-201.
Zimmermann et al., "Real-Time Quantitative Polymerase Chain Reaction Measurement of Male Fetal DNA in Maternal Plasma", Methods in Molecular Medicine: Single Cell Diagnostics, 2007, 132:43-49.
U.S. Appl. No. 13/782,883, Final Office Action mailed on May 26, 2016, 16 pages.
U.S. Appl. No. 15/647,171, Notice of Allowance mailed on Jan. 14, 2021, 7 pages.
European Application No. 11745050.2, Extended European Search Report mailed on Dec. 2, 2015, 7 pages.
Persing et al., Diagnostic Molecular Biology: Principles and Applications, Mayo Foundation, Rochester, American Society for Microbiology, 1993, 13 pages.
Robin et al., Defining the Clinical Spectrum of Deletion 22q11.2, The Journal of Pediatrics, vol. 147, No. 1, Jul. 2005, pp. 90-96.

* cited by examiner

METHODS AND PROCESSES FOR NON-INVASIVE ESTIMATION OF FETAL FRACTION

RELATED PATENT APPLICATIONS

This patent application is a continuation application of U.S. patent application Ser. No. 15/647,171, filed on Jul. 11, 2017, entitled METHODS AND PROCESSES FOR NON-INVASIVE ASSESSMENT OF A GENETIC VARIATION, naming Lin TANG and Cosmin DECIU as inventors, and designated by U.S. Pat. No. 11,004,537, which is a continuation application of U.S. patent application Ser. No. 14/127,912, filed on Apr. 7, 2014, entitled METHODS AND PROCESSES FOR NON-INVASIVE ASSESSMENT OF A GENETIC VARIATION, naming Lin TANG and Cosmin DECIU as inventors, and designated by a national stage of international patent application number PCT/US2012/043388, filed Jun. 20, 2012, entitled METHODS AND PROCESSES FOR NON-INVASIVE ASSESSMENT OF A GENETIC VARIATION, naming Lin TANG and Cosmin DECIU as inventors, and designated by U.S. Provisional Patent Application No. 61/500,842, filed Jun. 24, 2011, entitled METHODS AND PROCESSES FOR NON-INVASIVE ASSESSMENT OF A GENETIC VARIATION, naming Lin TANG and Cosmin DECIU as inventors. The entire content of the foregoing patent applications is incorporated herein by reference, including all text, tables, and drawings.

FIELD

Technology provided herein relates in part to methods and processes for non-invasive assessment of a genetic variation.

BACKGROUND

Genetic information of all living organisms (e.g., animals, plants and microorganisms) and other forms of replicating genetic information like viruses is encoded in deoxyribonucleic acid (DNA) or ribonucleic acid (RNA). Genetic information is the succession of nucleotides or modifications thereof representing the primary structure of real or hypothetical DNA/RNA molecule or strands with the capacity to carry information. In humans, the complete genome contains about 30,000 genes located on 24 chromosomes (The Human Genome, T. Strachan, BIOS Scientific Publishers, 1992). Each gene codes for a specific protein, which after its expression via transcription and translation, fulfills a specific biochemical function within a living cell.

Identifying genetic variations or variances can lead to diagnosis of particular medical conditions including fetal aneuploidy, fetal gender determination, fetal DNA/RNA/fraction estimation, pathogen infection and other conditions such as cancer and other diseases, for example. Personalized therapy regimens based on a patient's identified genetic variance can result in life saving medical interventions.

Many medical conditions caused by genetic variations are known and include hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Genetic diseases such as these can result from a single addition, substitution, or deletion of a single nucleotide in the deoxynucleic acid (DNA) forming the particular gene. Certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klinefelter's Syndrome (XXY). Medical conditions such as fetal aneuploidy, fetal gender prediction, and fetal DNA/RNA (or fetal fraction) estimation can be determined by analysis of fetal locus-independent markers and fetal specific markers for placental mRNA, DNA, or DNA methylation patterns. Further, some DNA sequences may predispose an individual to any of a number of diseases such as diabetes, arteriosclerosis, obesity, various autoimmune diseases and cancer (e.g., colorectal, breast, ovarian, lung).

SUMMARY

The invention provides in part a method for non-invasive assessment of a genetic variation comprising: (a) identifying one or more dissimilarities for a feature between a subject data set and a reference data set by a statistical analysis wherein the subject data set comprises genomic nucleic acid sequence information of a sample from a subject and the reference data set comprises genomic nucleic acid sequence information of a biological specimen from one or more reference persons; (b) generating a multidimensional matrix from the dissimilarities; (c) reducing the multidimensional matrix into a reduced data set representation of the matrix; (d) classifying into one or more groups the reduced data set representation by one or more linear modeling analysis algorithms thereby providing a classification; and (e) determining the presence or absence of a genetic variation for the sample based on the classification. In some embodiments the method further comprises obtaining genomic nucleic acid sequence information of a sample from a subject and obtaining genomic nucleic acid sequence information of a biological specimen from one or more reference persons. In certain embodiments, the method further comprises receiving the subject data set and the reference data set. In some embodiments, the genetic variation is a fetal aneuploidy. In certain embodiments, the genetic variation is a fetal gender. In other embodiments, the genetic variation is a fetal fraction estimation. In certain embodiments, the subject is a pregnant female and the reference persons are pregnant females. In some embodiments, the reference persons do not include the subject. In other embodiments, the reference data set comprises genomic nucleic acid sequence information of a biological specimen from one or more reference persons and the subject. In certain embodiments, the sample is blood serum or blood plasma from the subject. In some embodiments, the genomic nucleic acid sequence information is from a multiplex sequence analysis. In other embodiments, the method comprises reiterating identification of the one or more dissimilarities in a pairwise analysis between each pair in the subject data set and the reference data set. In certain embodiments, the subject data set and the reference data set comprise a fluorescent signal or sequence tag information. In other embodiments, the method comprises quantifying the signal or tag using a technique selected from the group consisting of flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof. In certain embodiments, the statistical analysis is selected from the group consisting of decision tree, counternull, multiple comparisons, omnibus test, Behrens-Fisher problem, bootstrapping, Fisher's method for combining independent tests of significance, null hypothesis, type I error, type II error, exact test, one-sample Z test, two-sample Z test, paired Z-test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, and combination thereof. In some embodiments, the method for reducing the multidimensional matrix is selected from the group consisting of metric and non-metric multidimensional scaling, Sammon's non-linear mapping, principal component analysis and combinations thereof. In other embodiments, the linear modeling analysis algorithm is selected from the group consisting of analysis of variance, Anscombe's quartet, cross-sectional regression, curve fitting, empirical Bayes methods, M-estimator, nonlinear regression, linear regression, multivariate adaptive regression splines, lack-of-fit sum of squares, truncated regression model, censored regression model, simple linear regression, segmented linear regression, decision tree, k-nearest neighbor, supporter vector machine, neural network, linear discriminant analysis, quadratic discriminant analysis, and combinations thereof. In certain embodiments, the reference data set comprises features from pregnant females who are between 25 years old and 30 years old. In some embodiments, the reference data set comprises features from pregnant females who are between 30 years old and 35 years old. In other embodiments, the reference data set comprises features from pregnant females who are between 35 years old and 40 years old. In certain embodiments, the reference data set comprises features from pregnant females who are in the first trimester of pregnancy. In some embodiments, the reference data set comprises features from pregnant females who are in the second trimester of pregnancy. In other embodiments, the subject data set comprises features from pregnant females who are in the first trimester of pregnancy. In certain embodiments, the reference data set comprises features chosen from one or more of a physiological condition, genetic or proteomic profile, genetic or proteomic characteristic, response to previous treatment, weight, height, medical diagnosis, familial background, results of one or more medical tests, ethnic background, body mass index, age, presence or absence of at least one disease or condition, species, ethnicity, race, allergies, gender, presence or absence of at least one biological, chemical, or therapeutic agent in the subject, pregnancy status, lactation status, medical history, blood condition, and combinations thereof. In some embodiments, a statistical sensitivity and a statistical specificity is determined from the classified reduced data set representation. In other embodiments, the statistical sensitivity and statistical specificity are independently between 90% and 100%.

The invention also in part provides a method for non-invasive assessment of a genetic variation comprising: (a) obtaining a subject data set comprising genomic nucleic acid sequence information of a sample from a subject; (b) obtaining a reference data set comprising genomic nucleic acid sequence information of a biological specimen from one or more reference persons; (c) identifying one or more dissimilarities for a feature between the subject data set and the reference data set by a statistical analysis; (d) generating a multidimensional matrix from the dissimilarities; (e) reducing the multidimensional matrix and transforming the matrix into a reduced data set representation of the matrix; (f) classifying into one or more groups the reduced data set representation by one or more linear modeling analysis algorithms thereby providing a classification; and (g) determining the presence or absence of a genetic variation for the sample based on the classification.

The invention also in part provides a method for non-invasive assessment of fetal gender or fetal fraction estimation comprising: (a) receiving a subject data set comprising genomic nucleic acid sequence information of a biological specimen sample from a subject; (b) receiving a reference data set comprising genomic nucleic acid sequence information of a biological specimen from one or more reference persons; (b) classifying into one or more groups the subject data set for a feature by one or more linear modeling analysis algorithms based on the reference data set thereby providing a classification; and (c) determining fetal aneuploidy or fetal gender for the sample based on the classification. In certain embodiments, the method further comprises performing linear modeling analysis in a pairwise analysis between each pair in the subject data set and the reference data set.

The invention also in part provides an apparatus that identifies the presence or absence of a genetic variation comprising a programmable processor that implements a data set dimensionality reducer wherein the reducer implements a method comprising: (a) identifying one or more dissimilarities for a feature between a subject data set and a reference data set by a statistical analysis wherein the subject data set comprises genomic nucleic acid sequence information of a sample from a subject and the reference data set comprises genomic nucleic acid sequence information of a biological specimen from one or more reference persons; (b) generating a multidimensional matrix from the dissimilarities; (c) reducing the multidimensional matrix into a reduced data set representation of the matrix; (d) classifying into one or more groups the reduced data set representation by one or more linear modeling analysis algorithms thereby providing a classification; and (e) determining the presence or absence of a genetic variation for the sample based on the classification.

The invention also in part provides a computer program product, comprising a computer usable medium having a computer readable program code embodied therein, the computer readable program code adapted to be executed to implement a method for generating a reduced data set representation, the method comprising: (a) identifying one or more dissimilarities for a feature between a subject data set and a reference data set by a statistical analysis wherein the subject data set comprises genomic nucleic acid sequence information of a sample from a subject and the reference data set comprises genomic nucleic acid sequence information of a biological specimen from one or more reference persons; (b) generating a multidimensional matrix from the dissimilarities; (c) reducing the multidimensional matrix into a reduced data set representation of the matrix; (d) classifying into one or more groups the reduced data set representation by one or more linear modeling analysis algorithms thereby providing a classification; and (e) determining the presence or absence of a genetic variation for the sample based on the classification.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIGS. 6a and 6b show detection of trisomy 21 samples with pair-wise t-tests introduces false positives.

DETAILED DESCRIPTION

Figure 1A:
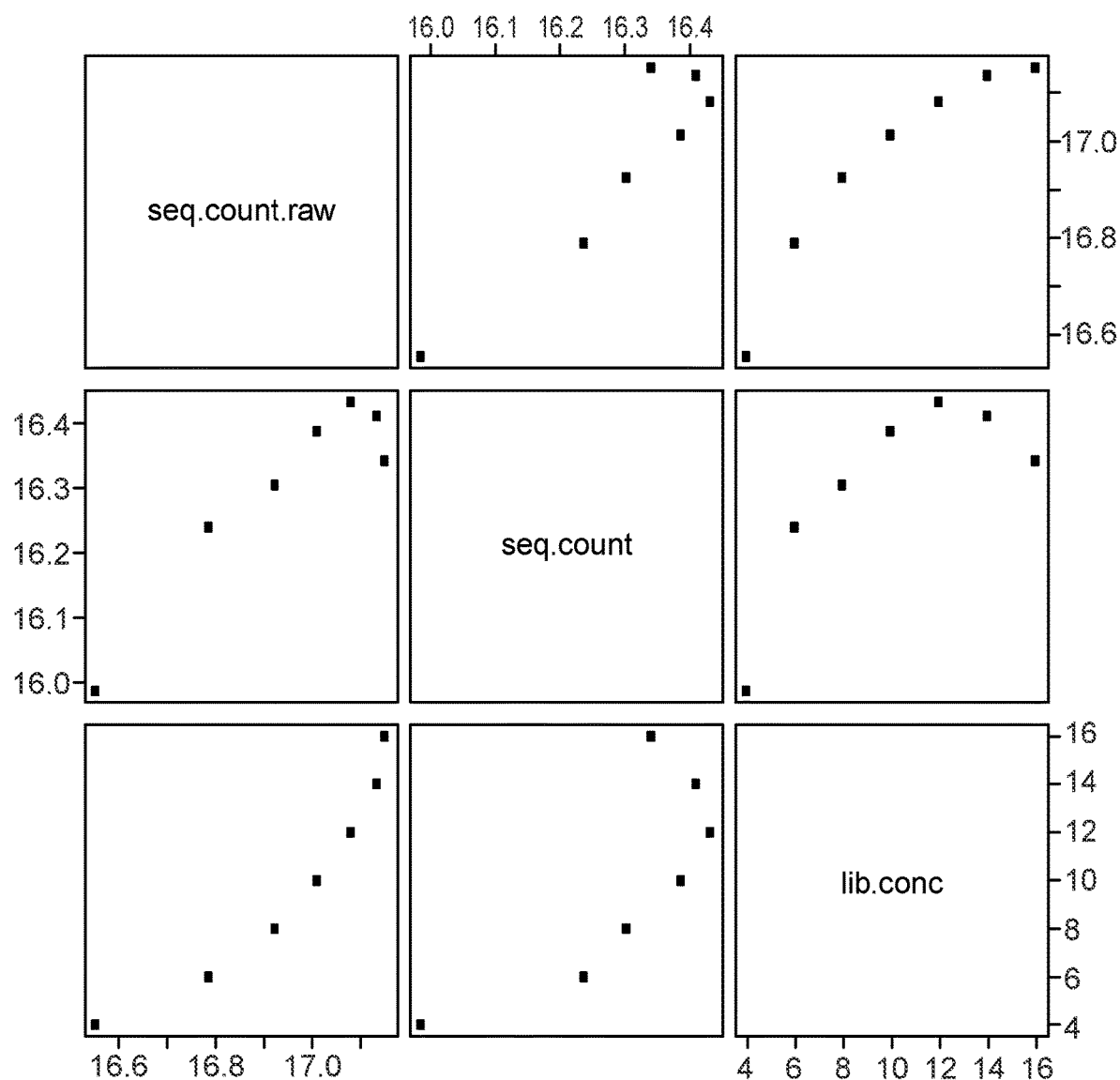
FIG. 1a shows the relationship among raw log sequence count, filtered log sequence count and library concentration.

In the following detailed description, reference is made to the accompanying drawings, which form a part hereof. In the drawings, similar symbols typically identify similar components, unless context dictates otherwise. Illustrative embodiments described in the detailed description, drawings, and claims do not limit the technology. Some embodiments may be utilized, and other changes may be made, without departing from the spirit or scope of the subject matter presented herein. It will be readily understood that aspects of the present disclosure, as generally described herein, and illustrated in the drawings, can be arranged, substituted, combined, separated, and designed in a wide variety of different configurations, all of which are explicitly contemplated herein.

Genetic Variations/Medical Conditions

Technology described herein can be used to identify the presence or absence of a genetic variation which are or are associated with a medical condition(s). Non-limiting examples of medical conditions are provided hereafter.

Fetal Gender

In some embodiments, the prediction of a fetal gender is determined. Gender determination generally is based on sex chromosomes. In humans, there are two sex chromosomes, the X and Y chromosomes. Individuals with XX are female and XY are male. Other variations may include XO, XYY, XXX, and XXY.

Chromosome Abnormalities

In some embodiments, the presence or absence of a fetal chromosome abnormality is determined. Chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations. The terms "aneuploidy" and "aneuploid" as used herein refer to an abnormal number of chromosomes in cells of an organism. As different organisms have widely varying chromosome complements, the term "aneuploidy" does not refer to a particular number of chromosomes, but rather to the situation in which the chromosome content within a given cell or cells of an organism is abnormal.

The term "monosomy" as used herein refers to lack of one chromosome of the normal complement. Partial monosomy can occur in unbalanced translocations or deletions, in which only a portion of the chromosome is present in a single copy (see deletion (genetics)). Monosomy of sex chromosomes (45, X) causes Turner syndrome.

The term "disomy" refers to the presence of two copies of a chromosome. For organisms such as humans that have two copies of each chromosome (those that are diploid or "euploid"), it is the normal condition. For organisms that normally have three or more copies of each chromosome (those that are triploid or above), disomy is an aneuploid chromosome complement. In uniparental disomy, both copies of a chromosome come from the same parent (with no contribution from the other parent).

The term "trisomy" refers to the presence of three copies, instead of the normal two, of a particular chromosome. The presence of an extra chromosome 21, which is found in Down syndrome, is called trisomy 21. Trisomy 18 and Trisomy 13 are the two other autosomal trisomies recognized in live-born humans. Trisomy of sex chromosomes can be seen in females (47, XXX) or males (47, XXY which is found in Klinefelter's syndrome; or 47,XYY).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing nondisjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the portion that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism most likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Following is a non-limiting list of chromosome abnormalities that can be potentially identified by methods described herein.

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobson Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
|  | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy |  |
| 20 | 20p- | trisomy 20p syndrome |
| 20 | 20p11.2-12 deletion | Alagille |

-continued

| Chromosome | Abnormality | Disease Association |
| --- | --- | --- |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

Preeclampsia

In some embodiments of the methods provided herein, the presence or absence of preeclampsia is determined. Preeclampsia is a condition in which hypertension arises in pregnancy (i.e. pregnancy-induced hypertension) and is associated with significant amounts of protein in the urine. In some cases, preeclampsia also is associated with elevated levels of extracellular nucleic acid and/or alterations in methylation patterns (see e.g. Kulkarni et al., (2011) DNA Cell Biol. 30 (2): 79-84; Hahn et al., (2011) Placenta 32 Suppl: S17-20). For example, a positive correlation between extracellular fetal-derived hypermethylated RASSF1A levels and the severity of pre-eclampsia has been observed (Zhao, et al., (2010) Pretat. Diagn. 30 (8): 778-82). In another example, increased DNA methylation was observed for the H19 gene in preeclamptic placentas compared to normal controls (Gao et al., (2011) Hypertens Res. February 17 (epub ahead of print)).

Preeclampsia is one of the leading causes of maternal and fetal/neonatal mortality and morbidity worldwide. Thus, widely applicable and affordable tests are needed to make an early diagnosis before the occurrence of the clinical symptoms. Circulating cell-free nucleic acids in plasma and serum are novel biomarkers with promising clinical applications in different medical fields, including prenatal diagnosis. Quantitative changes of cell-free fetal (cff) DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as the measurement of total cell-free DNA or the use of gender-independent fetal epigenetic markers, such as DNA methylation, offer an alternative. Cell-free RNA of placental origin might be another potentially useful biomarker for screening and diagnosis of preeclampsia in clinical practice. Fetal RNA is associated with subcellular placental particles that protect it from degradation. Its levels are ten-fold higher in pregnant women with preeclampsia compared to controls.

Pathogens

In some embodiments, the presence or absence of a pathogenic condition is determined. A pathogenic condition can be caused by infection of a host by any pathogen including, but not limited to, bacteria, viruses or fungi. Since pathogens typically possess nucleic acid (e.g. genomic DNA, genomic RNA, mRNA) that can be distinguishable from the host nucleic acid, the methods provided herein can be used to diagnose the presence or absence of a pathogen. Often, pathogens possess nucleic acid with characteristics that are unique to a particular pathogen such as, for example, epigenetic state and/or sequence variations, duplications and/or deletions. Thus, methods provided herein may be used to identify a particular pathogen or pathogen variant (e.g. strain).

Cancer

In some embodiments, the presence or absence of a cell proliferation disorder (e.g. cancer) is determined. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that can be positively correlated with elevated levels of circulating DNA include, breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from healthy cells, such as, for example, epigenetic state and/or sequence variations, duplications and/or deletions. Such characteristics can, for example, be specific to a particular type of cancer. Thus, it is further contemplated that the methods provided herein can be used to identify a particular type of cancer.

Samples

A sample can be from a subject or reference and sometimes is an aliquot from a subject or reference. A sample sometimes comprises nucleic acid from a subject or reference. Nucleic acid utilized in methods described herein often is obtained and isolated from a subject or reference. A subject or reference can be any living or non-living source, including but not limited to a human, an animal, a plant, a bacterium, a fungus, a protist. Any human or animal can be selected, including but not limited, non-human, mammal, reptile, cattle, cat, dog, goat, swine, pig, monkey, ape, gorilla, bull, cow, bear, horse, sheep, poultry, mouse, rat, fish, dolphin, whale, and shark.

Nucleic acid may be isolated from any type of suitable biological specimen. Example of specimens can be fluid or tissue from a subject, including, without limitation, umbilical cord blood, chorionic villi, amniotic fluid, cerebrospinal fluid, spinal fluid, lavage fluid (e.g., bronchoalveolar, gastric, peritoneal, ductal, ear, athroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample may be blood, and sometimes plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to further preparation in such embodiments. A fluid or tissue sample from which nucleic acid is extracted may be acellular. In some embodiments, a fluid or tissue sample may contain cellular elements or cellular remnants. In some embodiments fetal cells or cancer cells may comprise the sample.

The sample may be heterogeneous, by which is meant that more than one type of nucleic acid species is present in the sample. For example, heterogeneous nucleic acid can include, but is not limited to, (i) fetally derived and maternally derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant woman at 1-4, 4-8, 8-12, 12-16, 16-20, 20-24, 24-28, 28-32, 32-36, 36-40, or 40-44 weeks of fetal gestation, and sometimes between 5-28 weeks of fetal gestation.

Nucleic Acid Isolation and Processing

Nucleic acid may be derived from one or more sources (e.g., cells, soil, etc.) by methods known in the art. Cell lysis procedures and reagents are known in the art and may generally be performed by chemical, physical, or electrolytic lysis methods. For example, chemical methods generally employ lysing agents to disrupt the cells and extract the nucleic acids from the cells, followed by treatment with chaotropic salts. Physical methods such as freeze/thaw followed by grinding, the use of cell presses and the like are also useful. High salt lysis procedures are also commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, solution 1 can contain 15 mM Tris, pH 8.0; 10 mM EDTA and 100 µg/ml Rnase A; solution 2 can contain 0.2N NaOH and 1% SDS; and solution 3 can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" may be used interchangeably throughout the disclosure. The terms refer to nucleic acids of any composition from, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form, and unless otherwise limited, can encompass known analogs of natural nucleotides that can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome (e.g., a nucleic acid sample may be from one chromosome of a sample obtained from a diploid organism). The term also may include, as equivalents, derivatives, variants and analogs of RNA or DNA synthesized from nucleotide analogs, single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil. A nucleic acid may be prepared using a nucleic acid obtained from a subject as a template.

Nucleic acid may be isolated at a different time point as compared to another nucleic acid, where each of the samples are from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acid may be provided for conducting methods described herein without processing of the sample(s) containing the nucleic acid in certain embodiments. In some embodiments, nucleic acid is provided for conducting methods described herein after processing of the sample(s) containing the nucleic acid. For example, a nucleic acid may be extracted, isolated, purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. An isolated nucleic acid generally is provided with fewer non-nucleic acid components (e.g., protein, lipid)

than the amount of components present in a source sample. A composition comprising isolated nucleic acid can be substantially isolated (e.g., about 90%, 91%, 92%, 93%, 94%, 95%, 96%, 97%, 98%, 99% or greater than 99% free of non-nucleic acid components). The term "purified" as used herein refers to nucleic acid provided that contains fewer nucleic acid species than in the sample source from which the nucleic acid is derived. A composition comprising nucleic acid may be substantially purified (e.g., about 90%, 91%, 92%, 93%, 94%, 95%, 96%, 97%, 98%, 99% or greater than 99% free of other nucleic acid species). The term "amplified" as used herein refers to subjecting nucleic acid of a sample to a process that linearly or exponentially generates amplicon nucleic acids having the same or substantially the same nucleotide sequence as the nucleotide sequence of the nucleic acid in the sample, or portion thereof.

Nucleic acid can include extracellular nucleic acid in certain embodiments. The term "extracellular nucleic acid" as used herein refers to nucleic acid isolated from a source having substantially no cells (e.g., no detectable cells; may contain cellular elements or cellular remnants). Examples of acellular sources for extracellular nucleic acid are blood plasma, blood serum and urine. Without being limited by theory, extracellular nucleic acid may be a product of cell apoptosis and cell breakdown, which provides basis for extracellular nucleic acid often having a series of lengths across a large spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 40% of the overall nucleic acid (e.g., about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or 39% of the nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less).

Nucleic acid also may be processed by subjecting nucleic acid to a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by any suitable method known in the art, and the average, mean or nominal length of nucleic acid fragments can be controlled by selecting an appropriate fragment-generating procedure by the person of ordinary skill. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of unknown nucleotide sequence information.

Nucleic acid fragments may contain overlapping nucleotide sequences, and such overlapping sequences can facilitate construction of a nucleotide sequence of the previously non-fragmented nucleic acid, or a portion thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

Nucleic acid can be fragmented by various methods known to the person of ordinary skill, which include without limitation, physical, chemical and enzymatic processes. Examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected by the person of ordinary skill to generate non-specifically cleaved fragments or specifically cleaved fragments. Examples of processes that can generate non-specifically cleaved fragment nucleic acid include, without limitation, contacting nucleic acid with apparatus that expose nucleic acid to shearing force (e.g., passing nucleic acid through a syringe needle; use of a French press); exposing nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Nucleic acid may be specifically cleaved by contacting the nucleic acid with one or more specific cleavage agents. The term "specific cleavage agent" as used herein refers to an agent, sometimes a chemical or an enzyme that can cleave a nucleic acid at one or more specific sites. Specific cleavage agents often cleave specifically according to a particular nucleotide sequence at a particular site.

Examples of enzymatic specific cleavage agents include without limitation endonucleases (e.g., DNase (e.g., DNase I, II); RNase (e.g., RNase E, F, H, P); Cleavase™ enzyme; Taq DNA polymerase; E. coli DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpn I, Ksp I, Mlu I, MluN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I.); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Nucleic acid may be treated with a chemical agent, and the modified nucleic acid may be cleaved. In non-limiting examples, nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the portion of an amplified product thereof containing the corresponding nucleotide sequence of a nucleic acid template gene molecule. For example, it is within the scope of the present methods, compounds and compositions, that an amplified product can contain one or more nucleotides more than the amplified nucleotide region of the nucleic acid template gene sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). In such an example, the fragments or cleaved products corresponding to the nucleotides not arising from the nucleic acid template molecule will typically not provide any information regarding methylation in the nucleic acid template molecule. One skilled in the art can therefore understand that the fragments of an amplified product used to provide methylation information in the methods provided herein may be fragments containing one or more nucleotides arising from the nucleic acid template molecule, and not fragments containing nucleotides arising solely from a sequence other than that in the nucleic acid target molecule. Accordingly, one skilled in the art will understand the fragments arising from methods, compounds and compositions provided herein to include fragments arising from portions of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

In some embodiments, fragmented nucleic acid can be subjected to a size fractionation procedure and all or part of the fractionated pool may be isolated or analyzed. Size fractionation procedures are known in the art (e.g., separation on an array, separation by a molecular sieve, separation by gel electrophoresis, separation by column chromatography).

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. The term "methylation state" as used herein refers to whether a particular nucleotide in a polynucleotide sequence is methylated or not methylated. Methods for modifying a nucleic acid molecule in a manner that reflects the methylation pattern of the nucleic acid molecule are known in the art, as exemplified in U.S. Pat. No. 5,786,146 and U.S. patent publications 20030180779 and 20030082600. For example, non-methylated cytosine nucleotides in a nucleic acid can be converted to uracil by bisulfite treatment, which does not modify methylated cytosine. Non-limiting examples of agents that can modify a nucleotide sequence of a nucleic acid include methylmethane sulfonate, ethylmethane sulfonate, diethylsulfate, nitrosoguanidine (N-methyl-N'-nitro-N-nitrosoguanidine), nitrous acid, di-(2-chloroethyl) sulfide, di-(2-chloroethyl) methylamine, 2-aminopurine, t-bromouracil, hydroxylamine, sodium bisulfite, hydrazine, formic acid, sodium nitrite, and 5-methylcytosine DNA glycosylase. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts selected by the person of ordinary skill.

Data Sets

A data set is data from one or more samples. A data set may be either a reference data set or a subject data set. Data sets may encompass any type of collection of data grouped together, which include, but are not limited to, fetal chromosomal data, fetal DNA data, fetal RNA data, maternal chromosomal data, maternal DNA data, maternal RNA data, diseased chromosomal data, diseased DNA data, diseased RNA data, chromosomal data, DNA data, RNA data, sequence data, microarray expression data, gene ontology, nominal data, statistical data, protein expression data, cell signaling data, cell cycle data, amino acid sequence data, nucleotide sequence data, protein structure data, genome databases, protein sequence databases, protein structure databases, protein-protein data, signaling pathways databases, metabolic pathway databases, meta-databases, mathematical model databases, real time PCR primer databases, taxonomic database, antibody database, interferon database, cancer gene database, phylogenomic databases, human gene mutation database, mutation databases, electronic databases, wiki style databases, medical database, PDB, DBD, NCBI, MetaBase, Gene bank, Biobank, dbSNP, PubMed, Interactome, Biological data, Entrez, Flybase, CAMERA, NCBI- BLAST, CDD, Ensembl, Flymine, GFP-cDNA, Genome browser, GeneCard, HomoloGene, and the like.

Data may include nucleic acid (e.g. DNA and/or RNA) sequence information. Data may include data from flow cytometry, microarrays, sequence fluorescence labeling of the nuclei of cells and the like. Nucleotide sequence data may be determined by techniques such as cloning, electrophoresis, fluorescence tagging, mass spectrometry and the like.

Certain data sets are larger and require pre-processing in some embodiments, and sometimes data sets require pre-processing for further analysis. Genomic sequencing projects and microarray experiments, for example, can produce electronically-generated data flows that require computer accessible systems to process the information.

Data sets may be received or downloaded onto a computer or processor by any known method such as for example, via the internet, via wireless access, via hardware such as a flash drive, manual input, voice recognition, laser scanned, bar code scan, and the like. Data sets also may be generated while being received or come already packaged together. One data set that may be received may have homologous information, such as genes from the same organism, or heterologous information, such as genes and proteins from different organisms. One or more data sets may also be utilized as well as homologous and heterologous types of data sets. Data sets may also include overlapping data from another data set.

Data sets may also be pre-processed, standardized or normalized to conform to a particular standard. For example, a pre-processing step sometimes aids in normalizing data when using tissue samples since there are variations in experimental conditions from sequence analysis. Normalization can be carried out in a variety of manners. For example, sequence analysis can be normalized across all samples by subtracting the mean or by dividing by the repeated occurrence of particular sequencing motifs by the standard deviation to obtain centered data of standardized variance.

A normalization process can be applied to different types of data. To normalize gene sequencing across multiple tissue samples, for example, each repeated sequenced motif can be assigned a weight value based on its presence and the standard deviation for each motif can be computed. For all the tissue sample values of a particular gene, the mean can be subtracted and the resultant value divided by the standard deviation in some embodiments. In certain embodiments, an additional preprocessing step can be added by passing the data through a squashing function to diminish the importance of the outliers. This latter approach is also referred to as the Z-score of identification.

Another example of normalization is the Z-score mean absolute deviation of log sequence protocol. In this protocol, raw sequence are normalized by the Z-score of the log sequence using the equation (log (identification)-mean logarithm)/standard deviation logarithm. For sequencing data, the Z-score mean absolute deviation of log identification protocol normalizes each identified motif by the mean and mean absolute deviation of the logs of the sequence for all of the motifs in the sequence. The mean log identification and the mean absolute deviation log identification are computed for the log of raw sequence of the sequence data.

Reference Data Set

In some embodiments, data sets may be referred to as a reference set. A reference set is a known set, where one or more variables delineating the set is known. For example, genetic composition of DNA sequences is known for and often provided in a reference set. One or more reference sets may be used and one or more reference sets may be similar or different from each other based on the variables they have been grouped into and collected from. A reference set may include data from any suitable number of samples, and in some embodiments, a set may have about 10, 15, 20, 25, 30, 35, 40, 45, 50, 55, 60, 65, 70, 75, 80, 90, 100, 200, 300, 400, 500, 600, 700, 800, 900 or 1000 samples, or more than 1000 samples. The reference set may be considered or compared to samples tested in a particular period of time, and/or at a particular location and/or a particular organism or combination thereof. The reference set may be partly defined by other criteria, for example, age of an organism. The reference set may be included with samples which are subdivided into subsamples or replicates, all or some of which may be tested. The reference set may include a sample from the same individual, for example, as an aliquot from the same sample from the individual or at two different time points from the same individual. The reference set may exclude samples from the same individuals.

Data may also be included from a reference person or persons (e.g. reference data is also described hereafter). A reference person or persons or a group of reference persons may be any collection of people whose information is known. Any known information may include genetic background, blood type, chromosomal anomies, gender, cancer state, inheritable predispositions, age, carrier or possession of certain diseases, disease free, cancer free, or any other type of information that is known.

Subject Data Set

In some embodiments, certain data sets may be referred to as a subject data set. A subject data set often contains data from one or more subjects. A subject data set generally includes one or more variables that are unknown and/or tested for. For example, a genetic composition of DNA sequences sometimes is unknown for a subject set. One or more subject sets may be used and one or more subject sets may be similar or different from others based on the variables they have been grouped into and collected from. A subject set may include data from any suitable number of samples, and in some embodiments, a set may have about 10, 15, 20, 25, 30, 35, 40, 45, 50, 55, 60, 65, 70, 75, 80, 90, 100, 200, 300, 400, 500, 600, 700, 800, 900 or 1000 samples, or more than 1000 samples. The subject set may be considered or compared to data from samples tested in a particular period of time, and/or at a particular location and/or a particular organism or combination thereof. The subject set may be partly defined by criteria, for example, age of an organism, gestation period and other variables. The subject set may be included with samples which are subdivided into subsamples or replicates, all or some of which may be tested. A subject set may include one or more samples from the same individual, for example, as an aliquot from the same sample from the individual or at one or more time points from the same individual. A subject set may exclude one or more samples from the same individuals.

A subject data set may be from a collection of samples from one or more subjects. A subject may be a human male, a human female, a pregnant human female, an adolescent human male, an adolescent human female, a juvenile human, a human fetus, a human embryo, a living animal, a non-living animal, persons possibly having or diagnosed with a condition and the like. A sample may be any fluid or tissue from a subject. For example, a sample may be blood, blood serum, blood plasma, DNA, RNA, skin, cells, and the like.

Specific Subject Data Set-Maternal Nucleic Acid and Maternal/Fetal Nucleic Acid In some embodiments, a subject data set may come from maternal or fetal nucleic acid. In certain embodiments, the estimation of a fetal DNA or RNA is determined. In utero, fetal nucleated cells pass into the maternal bloodstream making it possible to use these cells for non-invasive prenatal diagnosis. Maternal plasma and serum also are a source of material for non-invasive prenatal diagnosis of certain genetic disorders. In certain embodiments, quantification of fetal DNA in maternal plasma and serum is assessed for a sufficient quantity before molecular diagnosis is conducted. In some embodiments determination of fetal DNA concentration variation in maternal plasma and/or serum, in relation to gestational age, is carried out.

Maternal nucleic acid that includes substantially no fetal nucleic acid can be obtained in any suitable manner known in the art. In some embodiments, such nucleic acid is obtained from a buccal swab or skin sample. Maternal nucleic acid that includes substantially no fetal nucleic acid often contains no detectable fetal nucleic acid, and can in some embodiments contain at most one to ten copies of fetal nucleic acid (e.g., 1, 2, 3, 4, 5, 6, 7, 8, 9, 10 copies of fetal nucleic acid), in total or per one milliliter of the sample containing the maternal nucleic acid.

The amount of fetal nucleic acid (e.g., concentration) in nucleic acid is determined in some embodiments. In certain embodiments, the amount of fetal nucleic acid is determined according to markers specific to a male fetus (e.g., Y-chromosome STR markers (e.g., DYS 19, DYS 385, DYS 392 markers); RhD marker in RhD-negative females), or according to one or more markers specific to fetal nucleic acid and not maternal nucleic acid (e.g., differential methylation between mother and fetus, or fetal RNA markers in maternal blood plasma; Lo, 2005, Journal of Histochemistry and Cytochemistry 53 (3): 293-296). Methylation-based fetal quantifier compositions and processes are described in U.S. application Ser. No. 12/561,241, filed Sep. 16, 2009, which is hereby incorporated by reference. The amount of fetal nucleic acid in extracellular nucleic acid can be quantified and used in conjunction with the aneuploidy detection methods provided herein. Thus, in certain embodiments, methods of the technology comprise the additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. The determination step can be performed before, during or after aneuploidy detection methods described herein. For example, to achieve an aneuploidy detection method with a given sensitivity or specificity, a fetal nucleic acid quantification method may be implemented prior to, during or after aneuploidy detection to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid) are further analyzed for the presence or absence of aneuploidy. In certain embodiments, determinations of the presence or absence of aneuploidy are selected (e.g., selected and communicated to a patient) only for samples having a certain threshold amount of fetal nucleic acid (e.g., about 15% or more fetal nucleic acid).

In some embodiments, extracellular nucleic acid is enriched or relatively enriched for fetal nucleic acid. Methods for enriching a sample for a particular species of nucleic acid are described in U.S. Pat. No. 6,927,028, filed Aug. 31, 2001, PCT Patent Application Number PCT/US07/69991, filed May 30, 2007, PCT Patent Application Number PCT/US2007/071232, filed Jun. 15, 2007, U.S. Provisional Application Nos. 60/968,876 and 60/968,878, and PCT Patent Application Number PCT/EP05/012707, filed Nov. 28, 2005. In certain embodiments, maternal nucleic acid is selectively removed (partially, substantially, almost completely or completely) from the sample. In certain embodiments, fetal nucleic acid is differentiated and separated from maternal nucleic acid based on methylation differences. Enriching for a particular low copy number species nucleic acid may also improve quantitative sensitivity.

Sequencing and Mapping

A data set can include nucleic acid sequence information, in some embodiments as addressed above. Sequencing, mapping and related analytical methods are known in the art (e.g., US2009/0029377, incorporated by reference). Certain aspects of such processes are described hereafter.

In certain embodiments, "obtaining" genomic nucleic acid sequence information of a sample from a subject and/or "obtaining" genomic nucleic acid sequence information of a biological specimen from one or more reference persons can involve directly sequencing nucleic acid to obtain the sequence information. In some embodiments, "obtaining" can involve receiving sequence information obtained directly from a nucleic acid by another.

Sequencing

Any sequencing method suitable for conducting methods described herein can be utilized, and in some embodiments, a massively parallel sequencing method is used. Systems utilized for massively parallel sequencing methods are commercially available from Roche 454 platform, the Applied Biosystems SOLID platform, the Helicos True Single Molecule DNA sequencing technology, the single molecule, real-time (SMRT.TM.) technology of Pacific Biosciences, for example. Nanopore sequencing also can be used in massively parallel sequencing approaches.

In some embodiments, one nucleic acid sample from one individual is sequenced. In certain embodiments, nucleic acid samples from two or more samples, where each sample is from one individual or two or more individuals, are pooled and the pool is sequenced. In the latter embodiments, a nucleic acid sample from each sample is identified by one or more unique identification tags.

A massively parallel sequencing process often produces many short nucleotide sequences that sometimes are referred to as "reads." Reads can be generated from one end of nucleic acid fragments ("single-end reads"), and sometimes are generated from both ends of nucleic acids ("double-end reads").

In some embodiments a fraction of the genome is sequenced, which sometimes is expressed in the amount of the genome covered by the determined nucleotide sequences (e.g., "fold" coverage less than 1). A genome also can be sequenced with redundancy, where a given region of the genome can be covered by two or more reads or overlapping reads (e.g., "fold" coverage greater than 1). In some embodiments, a genome is sequenced with about 0.1-fold to about 100-fold coverage, about 0.2-fold to 20-fold coverage, or about 0.2-fold to about 1-fold coverage (e.g., about 0.2-, 0.3-, 0.4-, 0.5-, 0.6-, 0.7-, 0.8-, 0.9-, 1-, 2-, 3—, 4-, 5-, 6-, 7-, 8-, 9-, 10-, 15-, 20-, 30-, 40-, 50-, 60-, 70-, 80-, 90-fold coverage). When a genome is sequenced with about 1-fold coverage, roughly 100% of the nucleotide sequence of the genome is represented by reads.

In some embodiments, single-end sequencing is performed. Such sequencing can be performed using an Illumina Genome Analyzer or Illumina Hy-Seq Analyzer, for example. The Illumina Genome Analyzer sequences clonally-expands single DNA molecules captured on a solid surface termed a flow cell. Each flow cell has eight lanes for the sequencing of eight individual specimens or pools of specimens. Each lane is capable of generating about 200 Mb of sequence which is only a fraction of the 3 billion base pairs of sequences in the human genome. Each genomic DNA or plasma DNA sample is sequenced using one lane of a flow cell. The short sequence tags generated are aligned to a reference genome sequence and the chromosomal origin is noted. The total number of individual sequenced tags aligned to each chromosome are tabulated and compared with the relative size of each chromosome as expected from the reference genome. Chromosome gains or losses then are identified.

In some embodiments, paired end sequencing is utilized. Instead of comparing the length of the sequenced fragments from that expected in the reference genome as described by Campbell et al (Nat Genet 2008; 40:722-729), the number of aligned sequenced tags are counted and sorted according to chromosomal location. Gains or losses of chromosomal regions or whole chromosomes were determined by comparing the tag counts with the expected chromosome size in the reference genome. As paired end sequencing allows one to deduce the size of the original nucleic acid fragment, one can focus on the counting of the number of paired sequenced tags corresponding to nucleic acid fragments of a specified size, such as <300 bp, <200 bp or <100 bp.

In certain embodiments, a fraction of a nucleic acid pool that is sequenced in a run is further sub-selected prior to sequencing. In certain embodiments, hybridization-based techniques (e.g., using oligonucleotide arrays) can be used to first sub-select for nucleic acid sequences from certain chromosomes (e.g. a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected pool of nucleic acids is sequenced randomly.

In some embodiments, nucleic acids may comprise a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Mapping Sequencing Reads

Mapping shotgun sequence information (i.e., sequence information from a fragment whose physical genomic position is unknown) can be done in a number of ways, which involve alignment of the obtained sequence reads with a matching sequence in a reference genome. See, Li et al., "Mapping short DNA sequencing reads and calling variants using mapping quality score," Genome Res., 2008 Aug. 19. Sequence reads are aligned to a reference sequence and those that align are designated as being "mapped" or a "sequence tag."

A "sequence tag" is a DNA sequence assigned specifically to one of chromosomes 1-22, X or Y. A sequence tag may be repetitive or non-repetitive within a single portion of the reference genome (e.g., a chromosome). A certain, small degree of mismatch (0-1) may be allowed to account for minor polymorphisms that may exist between the reference genome and the reads from individual genomes (maternal and fetal) being mapped, in certain embodiments. In some embodiments, no degree of mismatch is allowed for a read to be mapped to a reference sequence.

"Sequence tag density" refers to the normalized value of sequence tags for a defined window of a sequence on a chromosome where the sequence tag density is used for comparing different samples and for subsequent analysis. In some embodiments, the window is about 10 kilobases (kb) to about 100 kb, about 20 kb to about 80 kb, about 30 kb to about 70 kb, about 40 kb to about 60 kb, and sometimes about 50 kb. A sequence window also can be referred to as a "bin."

The value of the sequence tag density often is normalized within a sample. Normalization can be performed by counting the number of tags falling within each window on a chromosome; obtaining a median value of the total sequence tag count for each chromosome; obtaining a median value of all of the autosomal values; and using this value as a normalization constant to account for the differences in total number of sequence tags obtained for different samples. A sequence tag density sometimes is about 1 for a disomic chromosome. Sequence tag densities can vary according to sequencing artifacts, most notably G/C bias, which can be corrected by use of an external standard or internal reference (e.g., derived from substantially all of the sequence tags (genomic sequences), which may be, for example, a single chromosome or a calculated value from all autosomes). Thus, dosage imbalance of a chromosome or chromosomal regions can be inferred from the percentage representation of the locus among other mappable sequenced tags of the specimen. Dosage imbalance of a particular chromosome or chromosomal regions therefore can be quantitatively determined and be normalized.

A reference sequence often is an assembled or partially assembled genomic sequence from an individual or multiple individuals. A reference sequence sometimes is not from the fetus, the mother of the fetus or the father of the fetus, and is referred to herein as an "external reference." When a reference from the pregnant female is prepared ("maternal reference sequence") based on an external reference, reads from DNA of the pregnant female that contains substantially no fetal DNA are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

In some embodiments, a proportion of all of the sequence reads are from the chromosome involved in an aneuploidy (e.g., chromosome 21), and other sequence reads are from other chromosomes. By taking into account the relative size of the chromosome involved in the aneuploidy (e.g., "target chromosome": chromosome 21) compared to other chromosomes, one could obtain a normalized frequency, within a reference range, of target chromosome-specific sequences. If the fetus has an aneuploidy in the target chromosome, then the normalized frequency of the target chromosome-derived sequences is statistically greater than the normalized frequency of non-target chromosome-derived sequences, thus allowing the detection of the aneuploidy. The degree of change in the normalized frequency will be dependent on the fractional concentration of fetal nucleic acids in the analyzed sample.

Reagents for Sequencing and Other Nucleic Acid Analyses

Primers useful for detection, quantification, amplification, sequencing and analysis of nucleic acid can be utilized. In some embodiments primers are used in sets, where a set contains at least a pair. In some embodiments a set of primers may include a third or a fourth nucleic acid (e.g., two pairs of primers or nested sets of primers, for example). A plurality of primer pairs may constitute a primer set in certain embodiments (e.g., about 2, 3, 4, 5, 6, 7, 8, 9, 10, 15, 20, 25, 30, 35, 40, 45, 50, 55, 60, 65, 70, 75, 80, 85, 90, 95 or 100 pairs). In some embodiments a plurality of primer sets, each set comprising pair(s) of primers, may be used. The term "primer" as used herein refers to a nucleic acid that comprises a nucleotide sequence capable of hybridizing or annealing to a target nucleic acid, at or near (e.g., adjacent to) a specific region of interest. Primers can allow for specific determination of a target nucleic acid nucleotide sequence or detection of the target nucleic acid (e.g., presence or absence of a sequence or copy number of a sequence), or feature thereof, for example. A primer may be naturally occurring or synthetic. The term "specific" or "specificity", as used herein, refers to the binding or hybridization of one molecule to another molecule, such as a primer for a target polynucleotide. That is, "specific" or "specificity" refers to the recognition, contact, and formation of a stable complex between two molecules, as compared to substantially less recognition, contact, or complex formation of either of those two molecules with other molecules. As used herein, the term "anneal" refers to the formation of a stable complex between two molecules. The terms "primer", "oligo", or "oligonucleotide" may be used interchangeably throughout the document, when referring to primers.

A primer nucleic acid can be designed and synthesized using suitable processes, and may be of any length suitable for hybridizing to a nucleotide sequence of interest (e.g., where the nucleic acid is in liquid phase or bound to a solid support) and performing analysis processes described herein. Primers may be designed based upon a target nucleotide sequence. A primer in some embodiments may be about 10 to about 100 nucleotides, about 10 to about 70 nucleotides, about 10 to about 50 nucleotides, about 15 to about 30 nucleotides, or about 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nucleotides in length. A primer may be composed of naturally occurring and/or non-naturally occurring nucleotides (e.g., labeled nucleotides), or a mixture thereof. Primers suitable for use with embodiments described herein, may be synthesized and labeled using known techniques. Oligonucleotides (e.g., primers) may be chemically synthesized according to the solid phase phosphoramidite triester method first described by Beaucage and Caruthers, Tetrahedron Letts., 22:1859-1862, 1981, using an automated synthesizer, as described in Needham-VanDevanter et al., Nucleic Acids Res. 12:6159-6168, 1984. Purification of oligonucleotides can be effected by native acrylamide gel electrophoresis or by anion-exchange high-performance liquid chromatography (HPLC), for example, as described in Pearson and Regnier, J. Chrom., 255:137-149, 1983.

All or a portion of a primer nucleic acid sequence (naturally occurring or synthetic) may be substantially complementary to a target nucleic acid, in some embodiments. As referred to herein, "substantially complementary" with respect to sequences refers to nucleotide sequences that will hybridize with each other. The stringency of the hybridization conditions can be altered to tolerate varying amounts of sequence mismatch. Included are regions of counterpart, target and capture nucleotide sequences 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. Primers that are substantially complimentary to a target nucleic acid sequence are also substantially identical to the compliment of the target nucleic acid sequence. That is, primers are substantially identical to the anti-sense strand of the nucleic acid. As referred to herein, "substantially identical" with respect to sequences refers to nucleotide sequences that are 55% or more, 56% or more, 57% or more, 58% or more, 59% or more, 60% or more, 61% or more, 62% or more, 63% or more, 64% or more, 65% or more, 66% or more, 67% or more, 68% or more, 69% or more, 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more identical to each other. One test for determining whether two nucleotide sequences are substantially identical is to determine the percent of identical nucleotide sequences shared.

Primer sequences and length may affect hybridization to target nucleic acid sequences. Depending on the degree of mismatch between the primer and target nucleic acid, low, medium or high stringency conditions may be used to effect primer/target annealing. As used herein, the term "stringent conditions" refers to conditions for hybridization and washing. Methods for hybridization reaction temperature condition optimization are known to those of skill in the art, and may be found in Current Protocols in Molecular Biology, John Wiley & Sons, N.Y., 6.3.1-6.3.6 (1989). Aqueous and non-aqueous methods are described in that reference and either can be used. Non-limiting examples of stringent hybridization conditions are hybridization in 6X sodium chloride/sodium citrate (SSC) at about 45° C., followed by one or more washes in 0.2×SSC, 0.1% SDS at 50° C. Another example of stringent hybridization conditions are hybridization in 6X sodium chloride/sodium citrate (SSC) at about 45° C., followed by one or more washes in 0.2×SSC, 0.1% SDS at 55° C. A further example of stringent hybridization conditions is hybridization in 6X sodium chloride/sodium citrate (SSC) at about 45° C., followed by one or more washes in 0.2×SSC, 0.1% SDS at 60° C. Often, stringent hybridization conditions are hybridization in 6X sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C. Stringent hybridization temperatures can also be altered (i.e. lowered) with the addition of certain organic solvents, formamide for example. Organic solvents, like formamide, reduce the thermal stability of double-stranded polynucleotides, so that hybridization can be performed at lower temperatures, while still maintaining stringent conditions and extending the useful life of nucleic acids that may be heat labile.

As used herein, the phrase "hybridizing" or grammatical variations thereof, refers to binding of a first nucleic acid molecule to a second nucleic acid molecule under low, medium or high stringency conditions, or under nucleic acid synthesis conditions. Hybridizing can include instances where a first nucleic acid molecule binds to a second nucleic acid molecule, where the first and second nucleic acid molecules are complementary. As used herein, "specifically hybridizes" refers to preferential hybridization under nucleic acid synthesis conditions of a primer, to a nucleic acid molecule having a sequence complementary to the primer compared to hybridization to a nucleic acid molecule not having a complementary sequence. For example, specific hybridization includes the hybridization of a primer to a target nucleic acid sequence that is complementary to the primer.

In some embodiments primers can include a nucleotide subsequence that may be complementary to a solid phase nucleic acid primer hybridization sequence or substantially complementary to a solid phase nucleic acid primer hybridization sequence (e.g., about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater than 99% identical to the primer hybridization sequence complement when aligned). A primer may contain a nucleotide subsequence not complementary to or not substantially complementary to a solid phase nucleic acid primer hybridization sequence (e.g., at the 3' or 5' end of the nucleotide subsequence in the primer complementary to or substantially complementary to the solid phase primer hybridization sequence).

A primer, in certain embodiments, may contain a modification such as inosines, abasic sites, locked nucleic acids, minor groove binders, duplex stabilizers (e.g., acridine, spermidine), Tm modifiers or any modifier that changes the binding properties of the primers or probes. A primer, in certain embodiments, may contain a detectable molecule or entity (e.g., a fluorophore, radioisotope, colorimetric agent, particle, enzyme and the like). When desired, the nucleic acid can be modified to include a detectable label using any method known to one of skill in the art. The label may be incorporated as part of the synthesis, or added on prior to using the primer in any of the processes described herein. Incorporation of label may be performed either in liquid phase or on solid phase. In some embodiments the detectable label may be useful for detection of targets. In some embodiments the detectable label may be useful for the quantification target nucleic acids (e.g., determining copy number of a particular sequence or species of nucleic acid). Any detectable label suitable for detection of an interaction or biological activity in a system can be appropriately selected and utilized by the artisan. Examples of detectable labels are fluorescent labels such as fluorescein, rhodamine, and others (e.g., Anantha, et al., Biochemistry (1998) 37:2709 2714; and Qu & Chaires, Methods Enzymol. (2000) 321:353 369); radioactive isotopes (e.g., 1251, 1311, 35S, 31P, 32P, 33P, 14C, 3H, 7Be, 28 Mg, 57Co, 65Zn, 67Cu, 68Ge, 82Sr, 83Rb, 95Tc, 96Tc, 103Pd, 109Cd, and 127Xe); light scattering labels (e.g., U.S. Pat. No. 6,214,560, and commercially available from Genicon Sciences Corporation, CA); chemiluminescent labels and enzyme substrates (e.g., dioxetanes and acridinium esters), enzymic or protein labels (e.g., green fluorescence protein (GFP) or color variant thereof, luciferase, peroxidase); other chromogenic labels or dyes (e.g., cyanine), and other cofactors or biomolecules such as digoxigenin, strepdavidin, biotin (e.g., members of a binding pair such as biotin and avidin for example), affinity capture moieties and the like. In some embodiments a primer may be labeled with an affinity capture moiety. Also included in detectable labels are those labels useful for mass modification for detection with mass spectrometry (e.g., matrix-assisted laser desorption ionization (MALDI) mass spectrometry and electrospray(ES) mass spectrometry).

A primer also may refer to a polynucleotide sequence that hybridizes to a subsequence of a target nucleic acid or another primer and facilitates the detection of a primer, a target nucleic acid or both, as with molecular beacons, for example. The term "molecular beacon" as used herein refers to detectable molecule, where the detectable property of the molecule is detectable only under certain specific conditions, thereby enabling it to function as a specific and informative signal. Non-limiting examples of detectable properties are, optical properties, electrical properties, magnetic properties, chemical properties and time or speed through an opening of known size.

In some embodiments a molecular beacon can be a single-stranded oligonucleotide capable of forming a stem-loop structure, where the loop sequence may be complementary to a target nucleic acid sequence of interest and is flanked by short complementary arms that can form a stem. The oligonucleotide may be labeled at one end with a fluorophore and at the other end with a quencher molecule. In the stem-loop conformation, energy from the excited fluorophore is transferred to the quencher, through long-range dipole-dipole coupling similar to that seen in fluorescence resonance energy transfer, or FRET, and released as heat instead of light. When the loop sequence is hybridized to a specific target sequence, the two ends of the molecule are separated and the energy from the excited fluorophore is emitted as light, generating a detectable signal. Molecular beacons offer the added advantage that removal of excess probe is unnecessary due to the self-quenching nature of the unhybridized probe. In some embodiments molecular beacon probes can be designed to either discriminate or tolerate mismatches between the loop and target sequences by modulating the relative strengths of the loop-target hybridization and stem formation. As referred to herein, the term "mismatched nucleotide" or a "mismatch" refers to a nucleotide that is not complementary to the target sequence at that position or positions. A probe may have at least one mismatch, but can also have 2, 3, 4, 5, 6 or 7 or more mismatched nucleotides.

Statistical Analysis and Determining Dissimilarities Between Features

A variety of statistical methods can be applied to processes described herein. One or more of statistics, probability theory, data mining, pattern recognition, artificial intelligence, adaptive control, and theoretical computer science can be employed for recognizing complex patterns and making intelligent decisions or connections. For example, machine learning algorithms (e.g., trained machine learning algorithms) and/or other suitable algorithms may be applied to classify data according to learned patterns, for example. Machine learning algorithms can include supervised learning, unsupervised learning, semi-supervised learning, reinforcement learning, transduction, learning to learn and pareto-based multi-objective learning.

In certain embodiments, two types of algorithms that can be used in biological applications are supervised learning and unsupervised learning, for example. Supervised learning aids in discovering patterns in the data that relate data attributes with a target (class) attribute. These patterns then can be utilized to predict the values of the target attribute in future data instances. Unsupervised learning is often used when the data has no target attribute. Unsupervised learning is useful when a user wishes to explore data to identify intrinsic structure within (e.g., to determine how the data is organized).

In some embodiments, non-limiting examples of supervised learning are analytical learning, artificial neural networks, back propagation, boosting, Bayesian statistics, case-based reasoning, decision tree learning, inductive logic programming, Gaussian process regression, learning automata, minimum message length with decision trees or graphs, naïve Bayes classifiers, nearest neighbor algorithm, probably approximately correct learning (PAC), ripple down rules, symbolic machine learning algorithms, subsymbolic machine learning algorithms, support vector machines, random forests, ensembles of classifiers, ordinal classification, data pre-processing and handling imbalanced datasets.

In certain embodiments, examples of unsupervised learning include, but are not limited to, multivariate analysis, artificial neural networks, data clustering, expectation-maximization algorithm, self-organizing map, radial basis function network, generative topographic map, and blind source separation.

In some embodiments, clustering is a statistical technique for identifying similarity groups in data invoked clusters. For example, clustering groups (i) data instances similar to (near) each other in one cluster, and (ii) data instances different from (far away) each other into different clusters. Clustering often is referred to as an unsupervised learning task as no class values denoting an a priori grouping of the data instances normally are provided, where class values often are provided in supervised learning.

In certain embodiments, data clustering algorithms can be hierarchical. Hierarchical algorithms often find successive clusters using previously established clusters. These algorithms can be agglomerative ("bottom-up") or divisive ("top-down"), for example. Agglomerative algorithms often begin with each element as a separate cluster and often merge them into successively larger clusters. Divisive algorithms often begin with the whole set and often proceed to divide it into successively smaller clusters. Partitional algorithms typically determine all clusters at once or in iterations, but also can be used as divisive algorithms in the hierarchical clustering. Density-based clustering algorithms can be devised to discover arbitrary-shaped clusters. In this approach, a cluster often is regarded as a region in which the density of data objects exceeds a threshold. DBSCAN and OPTICS are two typical algorithms of this kind, for example. Two-way clustering, co-clustering or biclustering are clustering methods where not only the objects are clustered but also the features of the objects, i.e., if the data is represented in a data matrix, the rows and columns are clustered simultaneously, for example. Spectral clustering techniques often make use of the spectrum of the data similarity matrix to perform dimensionality reduction for clustering in fewer dimensions. Some clustering algorithms require specification of the number of clusters in the input data set, prior to execution of the algorithm. Barring knowledge of the proper value beforehand, the appropriate value must be determined, a problem for which a number of techniques have been developed.

In other clustering embodiments, one step is to select a distance measure, which will determine how the similarity of two elements is calculated. This selection generally will influence the shape of the clusters, as some elements may be close to one another according to one distance and farther away according to another. For example, in a 2-dimensional space, the distance between the point (x=1, y=0) and the origin (x=0, y=0) is 1 according to usual norms, but the distance between the point (x=1, y=1) and the origin can be 2, square root of 2 or 1 based on the 1-norm, 2-norm or infinity-norm distance, respectively.

In certain embodiments, several types of algorithms can be used in partitional clustering, including, but not limited to, k-means clustering, fuzzy c-means clustering, and QT clustering. A k-means algorithm often assigns each point to a cluster for which the center (also referred to as a centroid) is nearest. The center often is the average of all the points in the cluster, that is, its coordinates often are the arithmetic mean for each dimension separately over all the points in the cluster. Examples of clustering algorithms include, but are not limited to, CLARANS, PAM, CLATIN, CLARA, DBSCAN, BIRCH, WaveCluster, CURE, CLIQUE, OPTICS, K-means algorithm, and hierarchical algorithm.

In other embodiments, other statistical methods that may be used, for example, include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, and combinations thereof.

In certain embodiments ROC analysis may be used. ROC (Receiver Operating Characteristic) analysis provides tools to select possibly optimal models and to discard suboptimal ones independently from (and prior to specifying) the cost context or the class distribution. ROC analysis is related in a direct and natural way to cost/benefit analysis of diagnostic decision making. The AUC (Area Under Curve) is equal to the probability that a classifier will rank a randomly chosen positive instance higher than a randomly chosen negative one. It can be shown that the area under the ROC curve is closely related to the Mann-Whitney U, which tests whether positives are ranked higher than negatives. It is also equivalent to the Wilcoxon test of ranks. ROC and AUC statistics can be used for model comparison, however, other statistical methods may also be used.

In some embodiments, signal detection theory may be used. Signal detection theory is a receiver operating characteristic (ROC), or simply ROC curve, is a graphical plot of the sensitivity, or true positive rate, vs. false positive rate (1-specificity or 1-true negative rate), for a binary classifier system as its discrimination threshold is varied. The ROC can also be represented equivalently by plotting the fraction of true positives out of the positives (TPR=true positive rate) vs. the fraction of false positives out of the negatives (FPR=false positive rate). Also known as a Relative Operating Characteristic curve, because it is a comparison of two operating characteristics (TPR & FPR) as the criterion changes.

In other embodiments, linear modeling analysis algorithm may also be used. Such algorithms include, for example analysis of variance, Anscombe's quartet, cross-sectional regression, curve fitting, empirical Bayes methods, M-estimator, nonlinear regression, linear regression, multivariate adaptive regression splines, lack-of-fit sum of squares, truncated regression model, censored regression model, simple linear regression, segmented linear regression, decision tree, k-nearest neighbor, supporter vector machine, neural network, linear discriminant analysis, quadratic discriminant analysis, and the like.

Dissimilarities

Dissimilarity is also known as the distance between two or more samples under some criterion. In a general sense, dissimilarity measures how different samples are. Within the Cartesian Plane, a Euclidean distance between two points is the measure of their dissimilarity, for example. A dissimilarity index can be defined as the percentage of a group that would have to move to another group so the samples achieve an even distribution.

A dissimilarity matrix is a matrix that illustrates the similarity or dissimilarity pair to pair (or pair-wise) between two sets. It can describe pairwise distinctions between M objects. The matrix is square and symmetric. The M×M matrix has the (ij)th element equal to the value of a chosen measure of distinction between the (i)th and the (j)th object. The diagonal members are defined as zero, meaning that zero is the measure of dissimilarity between an element and itself. Thus, the information the matrix holds can be seen as a triangular matrix. Any reasonable measure of dissimilarity may be used, including subjective scores of dissimilarity. The greater distinction between two objects, the greater the value the measure of dissimilarity.

Features

Feature selection, also known as variable selection, feature reduction, attribute selection or variable subset selection, often is used for selecting a subset of relevant features for building robust learning models. When applied to biological situations with regard to polynucleotides, the technique also can be referred to as discriminative polynucleotide selection, which for example detects influential polynucleotides based on DNA sequencing analysis. Feature selection also helps acquire a better understanding of data by identifying more important features and their relationship with each other. For example, in the case of yeast cell cycle data, expression values of the polynucleotides correspond to several different time points. The feature selections in the foregoing example can be polynucleotides and time, among others.

Features can be selected in many different ways. Features can be selected manually by a user or an algorithm can be chosen or programmed to aid in selection. One or more feature selections also can be chosen. In certain embodiments, one or more features that correlate to a classification variable are selected.

In certain embodiments, a user may select features that correlate strongest to a classification variable, also known as a maximum-relevance selection. A heuristic algorithm can be used, such as the sequential forward, backward, or floating selections, for example.

In some embodiments, features mutually far away from each other can be selected, while they still have "high" correlation to a classification variable. This approach also is known as minimum-Redundancy-Maximum-Relevance selection (mRMR), which may be more robust than the maximum relevance selection in certain situations.

A correlation approach can be replaced by, or used in conjunction with, a statistical dependency between variables. Mutual information can be used to quantify the dependency. For example, mRMR may be an approximation to maximizing the dependency between joint distribution of the selected features and the classification variable.

Any suitable feature selection of a data set may be chosen. A data set may include one or more features. For example, a feature selection may include fetal gender prediction, identification of chromosomal aneuploidy, identification of particular genes or proteins (e.g., all genes or proteins), identification of cancer, diseases, inherited genes/traits, chromosomal abnormalities, and the like, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. A feature may also be selected or identified by techniques such as gene expression levels, florescence intensity, time of expression, and the like, and combinations of the foregoing. Gene expression levels may be in the form of identification of sequence information, for example. Co-regulated gene and/or protein data may be in the form of a cell signaling pathway where expression gene vectors can display expression of certain gene promoters with regards to time of expression as well as location of expression, for example. Genes that are regulated with regards to amount of expression and location within specific cell cycles may be investigated, for example.

A feature may be constructed from the statistical manipulation of two or more features. For example, a linear model-based algorithm may be used to derive a feature based on the ratio of read counts (e.g., log sequence counts) or reads and the GC content of genome sections (e.g., test chromosomes).

A feature may be, for example, one or more of a physiological condition, genetic or proteomic profile, genetic or proteomic characteristic, response to previous treatment, weight, height, medical diagnosis, familial background, results of one or more medical tests, ethnic background, body mass index, age, presence or absence of at least one disease or condition, species, ethnicity, race, allergies, gender, presence or absence of at least one biological, chemical, or therapeutic agent in the subject, pregnancy status, lactation status, medical history, blood condition, and combinations thereof.

A feature may be, for example: (i) a number of sequence reads of genomic nucleic acid mapped to a portion of a reference genome; (ii) a total number of sequence reads of genomic nucleic acid mapped to a portion of a reference genome; (iii) the guanine and cytosine content of a portion of a reference genome (e.g., a chromosome or portion thereof); (iv) a ratio of the number of sequence reads mapped to a portion of a reference genome and the guanine and cytosine content of a portion of a reference genome and (v) a linear relation of the number of sequence reads mapped to a portion of a reference genome and the guanine and cytosine content of a portion of a reference genome for multiple portions of a reference genome, which can be different chromosomes.

Search often is a component of feature selection, which can involve search starting point, search direction, and search strategy in some embodiments. A user can measure the goodness of the generated feature subset. Feature selection can be supervised as well as unsupervised learning, depending on the class information availability in data. The algorithms can be categorized under filter and wrapper models, with different emphasis on dimensionality reduction or accuracy enhancement, in some embodiments.

Feature selection has been used in supervised learning to improve generalization of uncharacterized data. Many applicable algorithms involve a combinatorial search through the space of all feature subsets. Due to the large size of this search space, that can be exponential in the number of features, heuristics often are employed. Use of heuristics may result in a loss of guarantee regarding optimality of the selected feature subset in certain circumstances. In biological sciences, genetic search and boosting have been used for efficient feature selection. In some embodiments, relevance of a subset of features can be assessed, with or without employing class labels, and sometimes varying the number of clusters.

Multidimensional Matrices

Multidimensional scaling (MDS) can be employed to detect meaningful underlying dimensions that thereby allowing one to explain observed similarities or dissimilarities (distances) between the investigated objects. Using MDS, one can analyze any kind of similarity or dissimilarity matrix, in addition to correlation matrices.

MDS may be performed in a variety of ways. In some embodiments, the scaling procedure is not as important as the way MDS rearranges objects in an efficient manner, so as to arrive at a configuration that best approximates the observed distances. MDS moves objects around in the space defined by the requested number of dimensions, and checks how well the distances between objects can be reproduced by the new configuration. MDS uses a function minimization algorithm that evaluates different configurations with the goal of maximizing the goodness-of-fit (or minimizing "lack of fit"). MDS pictures the structure of a set of objects from data that approximate the distances between pairs of the objects. The data may be similarities, dissimilarities, distances, proximities or correlations.

Each object or event is represented by a point in a multidimensional space. The points are arranged in this space so that the distances between pairs of points have the strongest possible relation to the dissimilarities or similarities among the pairs of objects. For example, two similar objects are represented by two points that are close together, and two dissimilar objects are represented by two points that are far apart. The space may be a two- or three-dimensional Euclidean space, may be non-Euclidean, or may have more dimensions (multi-dimensional).

The scaled representation in multidimensional space may also be referred to as a matrix, or arrangement of the objects. For example, after dissimilarities between pair wised objects are found through any statistical analysis, these dissimilarities may be can be used to generate a multidimensional matrix to produce a multidimensional relationship between the objects.

Any type of MDS may be used. MDS may be qualitative (non-metric MDS) or quantitative (metric MDS), classical MDS (one matrix, unweighted model), replicated MDS (several matrices, unweighted model), weighted MDS (several matrices, weighted model), Sammon's non-linear mapping, principal component analysis and the like.

Representation of a Reduced Set

Certain data gathering efforts can result in a large amount of complex data that are disorganized and not amenable for analysis. For example, certain biotechnology data gathering platforms, such as sequencing analyzing platforms for example, often give rise to large amounts of complex data that are not conducive to analysis. With new scientific discoveries and the advent of new, efficient experimental techniques, such as DNA sequencing, an exponential growth of vast quantities of information are being collected, such as genome sequences, protein structures, and gene expression levels. While database technology enables efficient collection and storage of large data sets, technology provided herein facilitates human comprehension and diagnosis basis of the information in this data. Enormous amounts of data from various organisms are being generated by current advances in biotechnology. Using this information to ultimately provide treatments and therapies for individuals requires an in-depth understanding of the gathered information.

Data generated by these and other platforms in biotechnology and other industries often include redundant, irrelevant and noisy data. The data also often includes a high degree of dimensionality. It has been determined that analyzing two or more data sets along with statistical analysis and feature selections can efficiently and effectively eliminate redundant data, irrelevant data and noisy data. Such approaches can reduce a large amount of information into meaningful data, thereby reducing the dimensionality of a data set and rendering the data more amenable to analysis.

Technology provided herein can be utilized to identify patterns and relationships, and makes useful sense of some or all the information in a computational approach. When dealing with large amounts of data, where the volume is expansive in terms of relationships, connections, dependence and the like, such data may be multi-dimensional or high-dimensional data. Technology provided herein can reduce the dimensionality and can accomplish regression, pattern classification, and/or data mining which may be used in analyzing the data to obtain meaningful information from it. For example, reducing dimensionality often selects features that best represent the data. Data mining often applies methods to the data and can uncover hidden patterns. Choice of data analysis may depend upon the type of information a user is seeking from data at hand. For example, a reason for using data mining is to assist in the analysis of collections of observations of behavior. Choice of data analysis also may depend on how a user interprets data, predict its nature, or recognize a pattern.

As described above with regard to reducing dimensionality of a data set, where features of a data set that represent the data are identified, such representative features generally are part of a reduced set or a representative reduced set. A reduced set may remove redundant data, irrelevant data or noisy data within a data set yet still provide a true embodiment of the original set, in some embodiments. A reduced set also may be a random sampling of the original data set, which provides a true representation of the original data set in terms of content, in some embodiments. A representative reduced set also may be a transformation of any type of information into a user-defined data set, in some embodiments. For example, a reduced set may be a presentation of expressed, functional proteins correlated with the presence of a particular gene sequence. Such representative images may be in the form of a graph, for example. The resulting reduced set, or representation of a reduced set, often is a transformation of original data on which processes described herein operate, reconfigure and sometimes modify.

Any type of representative reduced set media may be used, for example digital representation (e.g. digital data) of, for example, a peptide sequence, a nucleic acid sequence, a gene expression data, gene ontology data, protein expression data, cell signaling data, cell cycle data, protein structure data and the like. A computer or programmable processor may receive a digital or analog (for conversion into digital) representation of an input and/or provide a digitally-encoded representation of a graphical illustration, where the input may be implemented and/or accessed locally or remotely.

A reduced data set representation may include, without limitation, digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing.

A representative reduced set may be generated by any method known in the art. For example, presence of expressed, functional proteins correlated to sequence data may be quantified or transformed into digital data, this digital data may be analyzed by algorithms and a reduced set produced. The reduced set may be presented or illustrated or transformed into a representative graph, such as a scatter plot, for example.

Classifying Reduced Sets Into One or More Groups

A reduced set may be classified in any manner. A reduced set may be classified, ordered, paired, clustered, and the like such that the data is interpreted in a manner based on the reduced representational scaling model. Classification is the forming a class or classes; a distribution into one or more groups, as classes, orders, families, etc., according to some common relations or attributes depending on the data sets used. Classification of a reduced set may be, for example, into two distinct groups: cancerous/non-cancerous, male/female, aneuploidy/non-aneuploidy, having a disease/disease-free, normal/abnormal, having genetic dispositions/not having genetic dispositions, malignant/benign, and the like. Any type of regression analysis may be used to group or classify a reduced set such as, for example, linear, nonlinear, ordinary least squares, Bayesian methods, least absolute deviations, quantile, distance metric learning, parametric, and nonparametric regression. Regression analysis includes any techniques for modeling and analyzing several variables, when the focus is on the relationship between a dependent variable and one or more independent variables.

Other statistical methods for characterizing a reduced set may include, for example, descriptive statistics, statistical inference, correlation, categorical multivariate, time-series or survival analysis or other such applications. The number of groups a reduced set may be classified into may be in any suitable number (e.g., about 1, 2, 3, 4, 5, 6, 7, 8, 9, 10, 11, 12, 13, 14, 15, 16, 17, 18, 19,20, 21. 22. 23. 24. 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101 or more, 125 or more, 150 or more, 175 or more, 200 or more, 225 or more, 250 or more, 275 or more, 300 or more, 325 or more, 350 or more, 375 or more, or 400 or more groups).

Determining the Presence or Absence of a Medical Condition

The term "identifying the presence or absence of a medical condition" as used herein refers to any method for obtaining such information, including, without limitation, obtaining the information from a laboratory file. A laboratory file can be generated by a laboratory that carried out an assay to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

Sensitivity/Specificity

Different methods of predicting medical conditions or abnormality or normality can produce different types of results. For any given prediction, there are four possible types of outcomes: true positive, true negative, false positive, or false negative. The term "true positive" as used herein refers to a subject correctly diagnosed as having an outcome. The term "false positive" as used herein refers to a subject wrongly identified as having an outcome. The term "true negative" as used herein refers to a subject correctly identified as not having an outcome. The term "false negative" as used herein refers to a subject wrongly identified as not having an outcome. Two measures of performance for any given method can be calculated based on the ratios of these occurrences: (i) a sensitivity value, the fraction of predicted positives that are correctly identified as being positives (e.g., the fraction of matched sets correctly identified by level comparison detection/determination as indicative of an outcome, relative to all matched sets identified as such, correctly or incorrectly), thereby reflecting the accuracy of the results in detecting the outcome; and (ii) a specificity value, the fraction of predicted negatives correctly identified as being negative (the fraction of matched sets correctly identified by level comparison detection/determination as indicative of mismatching normality, relative to all matched sets identified as such, correctly or incorrectly), thereby reflecting accuracy of the results in detecting the outcome.

The term "sensitivity" as used herein refers to the number of true positives divided by the number of true positives plus the number of false negatives, where sensitivity (sens) may be within the range of $0 \leq sens \leq 1$. Ideally, certain methods have the number of false negatives equaling zero or close to equaling zero, so that no subject is wrongly identified as not having at least one chromosome abnormality when they indeed have at least one chromosome abnormality. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of $0 \leq spec \leq 1$. Ideally, methods embodiments herein have the number of false positives equaling zero or close to equaling zero, so that no subject wrongly identified as having at least one chromosome abnormality when they do not have the chromosome abnormality being assessed. Hence, a method that has sensitivity and specificity equaling one, or 100%, sometimes is selected.

In certain embodiments, one or more of ratio, sensitivity and/or specificity are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). A probability (e.g., that a particular outcome determined by an algorithm is not due to chance) in certain embodiments is expressed as a p-value, and sometimes the p-value is about 0.05 or less (e.g., about 0.05, 0.04, 0.03, 0.02 or 0.01, or less than 0.01 (e.g., about 0.001 or less, about 0.0001 or less, about 0.00001 or less, about 0.000001 or less)).

User Interface

Provided herein are methods, apparatuses or computer programs where a user may enter, request, query or determine options for using particular information or programs or processes such as data sets, feature selections, statistical analysis algorithms, statistical significance algorithms, statistical algorithms, iterative steps, validation algorithms, and graphical representations, for example. In some embodiments, a data set may be entered by a user as input information or a user may download one or more data sets by any suitable hardware media (i.e. flash drive).

A user also may, for example, place a query to a data set dimensionality reducer which then may acquire a data set via internet access or a programmable processor may be prompted to acquire a suitable data set based on given parameters. A programmable processor also may prompt the user to select one or more data set options selected by the processor based given parameters. A programmable processor also may prompt the user to select one or more data set options selected by the processor based on information found via the internet, other internal or external information, or the like. Similar options may be chosen for selecting the feature selections, statistical analysis algorithms, statistical significance algorithms, statistical algorithms, iterative steps, validation algorithms, and graphical representations of the methods, apparatuses, or computer programs herein.

A processor may be programmed to automatically perform a task described herein that a user" could perform. Accordingly, a processor, or algorithm conducted by such a processor, can require little to no supervision or input from a user (e.g., software may be programmed to implement a function automatically).

By "obtaining" or "receiving" input information is meant receiving the signal information by computer communication means from a local, or remote site, human data entry, or any other method of receiving signal information. The input information may be generated in the same location at which it is received, or it may be generated in a different location and transmitted to the receiving location.

Also provided are computer program products, such as, for example, a computer program products comprising a computer usable medium having a computer readable program code embodied therein, the computer readable program code adapted to be executed to implement a method comprising (a) identifying one or more dissimilarities for a feature between a subject data set and a reference data set by a statistical analysis wherein the subject data set comprises genomic nucleic acid sequence information of a sample from a subject and the reference data set comprises genomic nucleic acid sequence information of a biological specimen from one or more reference persons; (b) generating a multidimensional matrix from the dissimilarities; (c) reducing the multidimensional matrix into a reduced data set representation of the matrix; (d) classifying into one or more groups the reduced data set representation by one or more linear modeling analysis algorithms thereby providing a classification; and (e) determining the presence or absence of a medical condition for the sample based on the classification.

Machines, Software & Data Processing

Computer program products include, for example, any electronic storage medium that may be used to provide instructions to a computer, such as, for example, a removable storage device, CD-ROMS, a hard disk installed in hard disk drive, signals, magnetic tape, DVDs, optical disks, flash drives, RAM or floppy disk, and the like.

The systems discussed herein may further comprise general components of computer systems, such as, for example, network servers, laptop systems, desktop systems, handheld systems, personal digital assistants, computing kiosks, and the like. The computer system may comprise one or more input means such as a keyboard, touch screen, mouse, voice recognition or other means to allow the user to enter data into the system. The system may further comprise one or more output means such as a CRT or LCD display screen, speaker, FAX machine, impact printer, inkjet printer, black and white or color laser printer or other means of providing visual, auditory or hardcopy output of information. In certain embodiments, a system includes one or more machines.

The input and output means may be connected to a central processing unit which may comprise among other components, a microprocessor for executing program instructions and memory for storing program code and data. In some embodiments the methods may be implemented as a single user system located in a single geographical site. In other embodiments methods may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by the provider or it may be implemented as an internet based service where the user accesses a web page to enter and retrieve information.

As used herein, software refers to computer readable program instructions that, when executed by a computer, perform computer operations. Typically, software is provided on a program product containing program instructions recorded on a computer readable medium, including, but not limited to, magnetic media including floppy disks, hard disks, and magnetic tape; and optical media including CD-ROM discs, DVD discs, magneto-optical discs, and other such media on which the program instructions can be recorded.

The various software modules associated with the implementation of the present products and methods can be suitably loaded into the a computer system as desired, or the software code can be stored on a computer-readable medium such as a floppy disk, magnetic tape, or an optical disk, or the like. In an online implementation, a server and web site maintained by an organization can be configured to provide software downloads to remote users. As used herein, "module," including grammatical variations thereof, means, a self-contained functional unit which is used with a larger system. For example, a software module is a part of a program that performs a particular task.

The present methods may be implemented using hardware, software or a combination thereof and may be implemented in a computer system or other processing system. An example computer system may include one or more processors. A processor can be connected to a communication bus. The computer system may include a main memory, often random access memory (RAM), and can also include a secondary memory. The secondary memory can include, for example, a hard disk drive and/or a removable storage drive, representing a floppy disk drive, a magnetic tape drive, an optical disk drive, memory card etc. The removable storage drive reads from and/or writes to a removable storage unit in a well-known manner. A removable storage unit includes, but is not limited to, a floppy disk, magnetic tape, optical disk, etc. which is read by and written to by, for example, a removable storage drive. As will be appreciated, the removable storage unit includes a computer usable storage medium having stored therein computer software and/or data.

In alternative embodiments, secondary memory may include other similar means for allowing computer programs or other instructions to be loaded into a computer system. Such means can include, for example, a removable storage unit and an interface device. Examples of such can include a program cartridge and cartridge interface (such as that found in video game devices), a removable memory chip (such as an EPROM, or PROM) and associated socket, and other removable storage units and interfaces which allow software and data to be transferred from the removable storage unit to a computer system.

The computer system may also include a communications interface. A communications interface allows software and data to be transferred between the computer system and external devices. Examples of communications interface can include a modem, a network interface (such as an Ethernet card), a communications port, a PCMCIA slot and card, etc. Software and data transferred via communications interface are in the form of signals, which can be electronic, electromagnetic, optical or other signals capable of being received by communications interface. These signals are provided to communications interface via a channel. This channel carries signals and can be implemented using wire or cable, fiber optics, a phone line, a cellular phone link, an RF link and other communications channels. Thus, in one example, a communications interface may be used to receive signal information to be detected by the signal detection module.

In a related aspect, the signal information may be input by a variety of means, including but not limited to, manual input devices or direct data entry devices (DDEs). For example, manual devices may include, keyboards, concept keyboards, touch sensitive screens, light pens, mouse, tracker balls, joysticks, graphic tablets, scanners, digital cameras, video digitizers and voice recognition devices. DDEs may include, for example, bar code readers, magnetic strip codes, smart cards, magnetic ink character recognition, optical character recognition, optical mark recognition, and turnaround documents. In one embodiment, an output from a gene or chip reader my serve as an input signal.

In certain embodiments, simulated data often is generated in an in silico process. As used herein, the term "in silico" refers to research and experiments performed using a computer. In silico methods include, but are not limited to, gene expression data, cell cycle data, molecular modeling studies, karyotyping, genetic calculations, biomolecular docking experiments, and virtual representations of molecular structures and/or processes, such as molecular interactions.

In certain embodiments, simulated (or simulation) data can aid data processing, for example, by training an algorithm or testing an algorithm. Simulated data may for instance involve hypothetical various sampling of different groupings of gene sequences and the like. Simulated data may be based on what might be expected from a real population or may be skewed to test an algorithm and/or to assign a correct classification based on a simulated data set. Simulated data also is referred to herein as "virtual" data. Simulations can be performed in most instances by a computer program. One possible step in using a simulated data set is to evaluate the confidence of the identified results, i.e. how well the random sampling matches or best represents the original data. A common approach is to calculate the probability value (p-value) which estimates the probability of a random sample having better score than the selected samples. As p-value calculations can be prohibitive in certain circumstances, an empirical model may be assessed, in which it is assumed that at least one sample matches a reference sample (with or without resolved variations). Alternatively, other distributions such as Poisson distribution can be used to describe the probability distribution.

Described herein can be an algorithm incorporated into software of any suitable type. In mathematics, computer science, and related subjects, an algorithm may be an effective method for solving a problem using a finite sequence of instructions. Algorithms are used for calculation, data processing, and many other fields. Each algorithm can be a list of well-defined instructions for completing a task. Starting from an initial state, the instructions may describe a computation that proceeds through a well-defined series of successive states, eventually terminating in a final ending state. The transition from one state to the next is not necessarily deterministic, for example, some algorithms incorporate randomness. By way of example, without limitation, the algorithm(s) can be search algorithms, sorting algorithms, merge algorithms, numerical algorithms, graph algorithms, string algorithms, modeling algorithms, computational genometric algorithms, combinatorial algorithms, machine learning, cryptography, data compression algorithms and parsing techniques and the like. An algorithm can include one or more algorithms working in combination. An algorithm can be of any suitable complexity class and/or parameterized complexity. An algorithm can be used for calculation or data processing, or used in a deterministic or probabilistic/predictive approach to a method in some embodiments. Any processing of data, such as by use with an algorithm, can be utilized in a computing environment, by use of a programming language such as C, C++, Java, Perl, Python, Fortran, and the like. The algorithm can be modified to include margin of errors, statistic analysis, statistical significance as well as comparison to other information or data sets (for example in using a neural net or clustering algorithm).

In certain embodiments, several algorithms may be implemented for use in software. These algorithms can be trained with raw data in some embodiments. For each new raw data sample, the trained algorithms produce a representative reduced set. Based on the reduced set of the new raw data samples, the performance of the trained algorithm may be assessed based on sensitivity and specificity. Finally, an algorithm with the highest sensitivity and/or specificity or combination thereof may be identified.

Examples

The examples set forth below illustrate certain embodiments and do not limit the technology.

Example 1: A Linear Model-Based Algorithm for Detecting Fetal Aneuploidy with Massively Parallel Sequencing This example discusses a novel algorithm, based on the observation of the linear relationship between the sequence tag counts ratio and sequence GC content, for the analysis of small increment in the chromosome dosage in trisomy. From the Z-score calculated from the linear model, a dissimilarity matrix was derived for all the samples in analysis. The dissimilarity matrix was then reduced from high dimensional space to lower dimensional space; classic classification method could be applied to differentiate the aneuploidy samples from the normal samples. This algorithm was successful to correct the samples in different experiment settings and was applicable in clinical practice. Also demonstrated is the utility of this algorithm by applying it to two clinical datasets for the diagnosis on trisomies 21, 13 and 18.

Herein describes the development of locus-independent methods which rely upon the massive-parallel sequencing techniques. The millions of short read sequence generated for each sample with DNA sequencing technology offered flexible sampling power in detecting the small increment gained from the fetal trisomy chromosomes mixed in the disomy maternal plasma DNA. Rather than quantifications on fetal specific markers, the sequencing based method directly compares the short read sequence counts of the tested chromosome against the reference. A linear modeled algorithm is then used to establish the relationship between the sequence counts and the GC content of each chromosome. The GC influence is factored in as well as experimental characteristics and their interactions. The trisomy samples were first detected by comparison of a single reference sample and a Student's t-test distribution was formed based on the comparison of the other chromosomes. The validity of this model is proved in a set of spike-in samples (Chu et al, 2009). The next testing was performed with a large clinical study and included other modifications to the method and process which improved the parameters for the best performance.

Figure 1B:
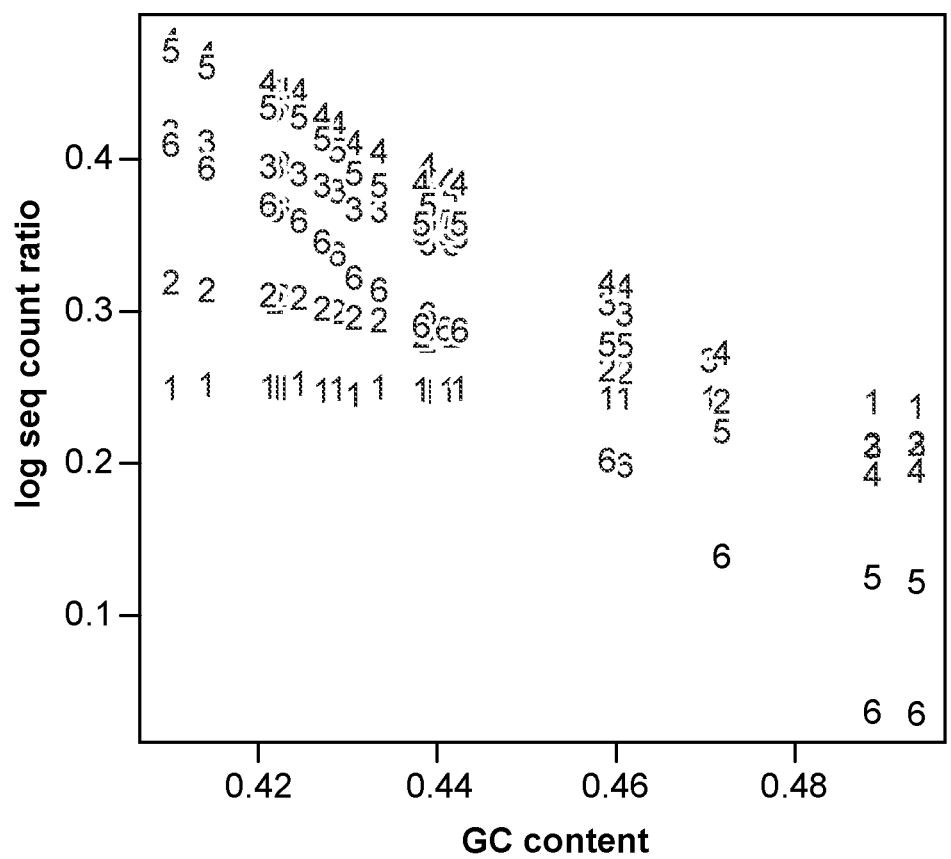
FIG. 1b shows the log sequence count ratio displayed a high correlation with their GC content.

This example is based on the observation of the linear relationship between the sequence tag counts ratio and sequence GC content. As seen in FIG. 1a, the raw sequence counts before the quality filter increased with the increased library concentration input for sequencing; however the unique matched sequence tag counts saturated when input library concentration reached 12 pM. In FIG. 1b, the log sequence count ratio displayed a high correlation with their GC content; the number designates the increased library concentration from 6 pM to 16 pM compared with the ones of 4 pM.

A novel algorithm based on a linear model is used for the detection of fetal aneuploidy. When the linear model is expanded to more test samples, reliance on a single sample as reference would lead to false positives depending on the choice of sample. Therefore, a pair-wise analysis for all the test and reference samples was performed. The resulting dissimilarity matrix could be then reduced into lower dimensional space for classification. This algorithm was applied to in-house data with different plex levels and then tested on two large clinical datasets. Its clinical utilities were proven in detecting trisomies 21, 13 and 18.

Sequencing

Illumina's cBOT instrument was used for cluster generation. The sequencing was performed on the Genome Analyzer IIx (Illumina, Inc., San Diego, CA). Illumina's accompany software suite RTA1.6/SCS2.6 were used for image analysis and base calling. The short read tags were aligned to the human reference genome (UCSC hg19) using CASAVA 1.6. The raw sequence counts were directly taken from the summary file output from CASAVA program. Sequence reads with a maximum one mismatch alignment against the reference genome were counted for each 50 kb bin of the chromosome. The total sequence count for each chromosome was summarized after filtering the bins with counts above 3 median absolute deviation of that chromosome. The GC percentage of each chromosome was also gathered from these one-mismatch sequence tags. The averaged GC percentage was plugged into the linear model.

Clinical Datasets

Two clinical datasets were employed for this study. The in-house data was composed of 480 samples. The sample processing and sequencing procedures were detailed in (Mathias Ehrich 2010). Among the total 480 samples, 13 samples, including one trisomy 21, were not analyzed due to broken tubes during centrifugation. This led to only 467 applicable ones for the analysis. The quality control procedure further excluded 18 samples (Mathias Ehrich 2010). The datasets of 467 and 449 samples before and after QC both underwent the analysis. There were a total of 41 and 39 trisomy 21 samples in each set.

The Hong Kong dataset was obtained from Dr. YM Lo's group through a personal communication. The samples were collected from public hospitals, including three different sites: Hong Kong, United Kingdom and the Netherlands. There were a total of 753 samples, which including 86 trisomy 21, 20 trisomy 13 and 42 trisomy 18. Massively parallel sequencing was done on the Illumina Genome Analyzer II in 8 plex. Experimentation began with the sequence alignment files that were received. The sequence tags were aligned against the human reference genome (UCSC hg18). The one-mismatch sequence tags were counted for each chromosome and used to summarize the total counts for each chromosome. This dataset did not undergo the 50 kb bin filtering step because the unfiltered sequence counts had better fitting results in the linear model for this dataset particularly. The GC percentages for each chromosome were also calculated from the aligned sequence tags.

Data Analysis

The log sequence tag count ratio and GC percentage of each chromosome were first plugged into the linear model. The Z-score based on the linear model was calculated for all pair-wise samples, including trisomy samples. This formed an n×n matrix composed of Z-scores. This dissimilarity matrix was then reduced into two dimensions by multidimensional scaling (MDS). In the unsupervised learning, the training set was first transformed by MDS; the test set was then projected onto the same space of the training set with a modified version of MDS. In the supervised learning, all the samples were transformed with MDS at one time. Linear discriminant analysis was then applied for classification. All calculations were done in the R environment.

R Development Core Team (2008). R: A language and environment for statistical computing. R Foundation for Statistical Computing, Vienna, Austria. ISBN 3-900051-07-0, URL http://www.R-project.org Example 2: Fetal Aneuploidy Results A Linear Relationship is Observed Between the Chromosome Sequence Tag Counts Ratio and their GC Content Massively parallel sequencing technology has been applied in several studies for the detection of a small variance of fetal aneuploidy in a maternal plasma DNA sample. Although massively parallel sequencing performs with high efficiency, there is noise or bias introduced in the sample amplification with PCR, a necessary step in both the Illumina Solexa and ABI SOLID™ sequencing platforms. This bias is largely attributed to uneven GC content across the genome. The different GC content will have a quantitative bias on the sequence tag counts at the levels of both chromosome sub-regions and whole chromosome. In this experiment, the uneven amplification of genomic sequence with different GC content was observed. Furthermore, the logged sequence tag counts ratio of the chromosomes between sample pairs followed a tight linear relationship with its GC content. To better understand this linear relationship, a serial dilution was used on a single library (concentration rangewas 4, 6, 8, 10, 12, 14, 16 pM). With the increase of library input, the raw sequence tag counts of the clustering, analyzed before the quality filters, increased accordingly. The unique matched sequence tag counts saturated at the library input of approximately 12 pM (FIG. 1a). All the subsequent sequencing trials were compared with the sequencing trial of the initial dilution point. The log sequence tag counts ratios followed a tight linear relationship with the GC content (averaged $R^2$=0.887) (FIG. 1b). The slope increased with the increase of the sequence count difference. The observation here fits into a linear model, where the GC content is factored in, as well as experimental influence, which account for the sequence tag count difference between two samples. The experimental characteristics in this model can be partially explained by the input library difference as illustrated here.

The GC content of sequenced tags was approximately 10% higher than those calculated from the human genome in the public domains (UCSC hg19). The GC content from the sequenced tag will better represent the GC bias introduced in sequencing compared to the sequenced human genome. In this study, the averaged GC content from the sequenced samples for all the calculations was used. The total sequence tag counts were used instead of the median sequence counts per 50Kb bin for each chromosome. Although it has been suggested that tag density data was more robust than the total sequence tag count, we found the sequence tag count ratio calculated with total count displayed high correlation with the GC content. We also noticed the abnormally high counts in consistent regions close to centromeres or telomeres; which may be due to the high repeat sequence embedded in these regions. To eliminate this biased effect on the total counts, the sequence tag counts were calculated for each 50 kb bin and those bins that were above 3 median absolute deviations from the median counts were excluded when summarizing the total counts for each chromosome.

A Linear Model-Based Algorithm to Detect Fetal Aneuploidy

Figure 6A:
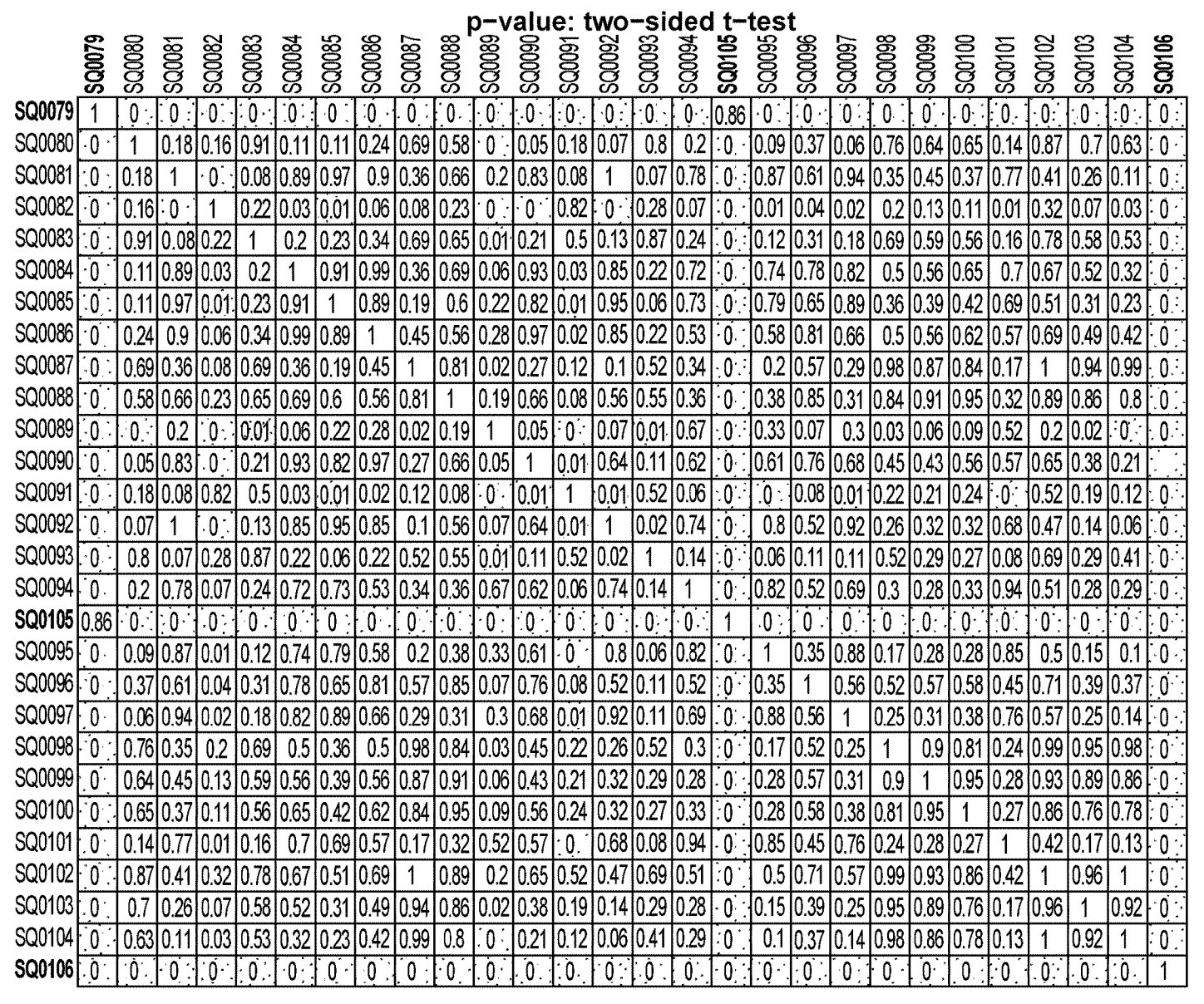
Figure 6B:
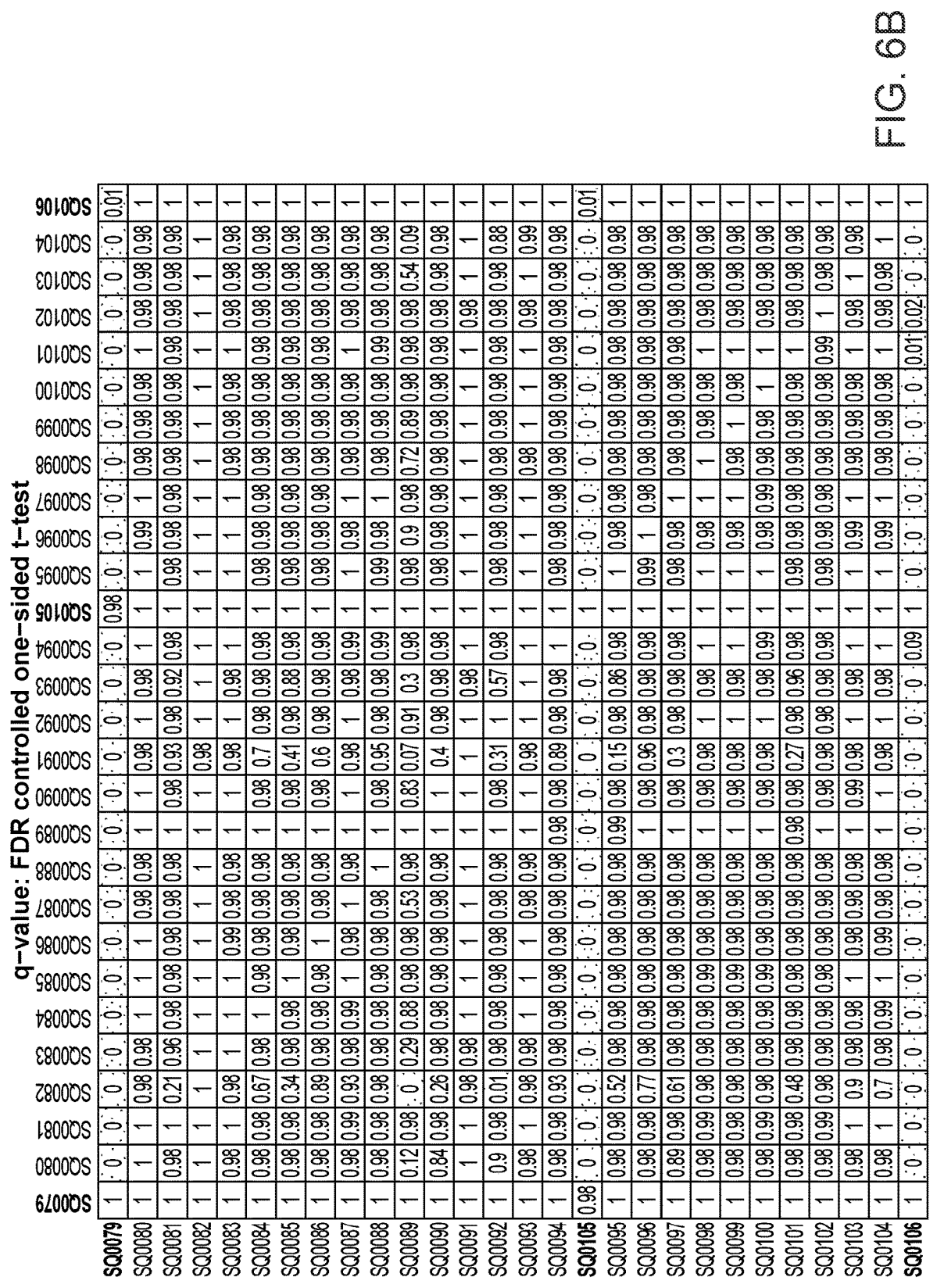

In addition to the spiked-in samples, we prepared the sequencing library directly from the maternal plasma samples. Higher than reported correlations of the logged sequence tag count ratio and its GC content, were observed, thus the linear model in calculating the Z-score for the significance test of the aneuploidy samples was adopted. The original test was based on the comparison of a single pair of sample and reference. This experiment improves upon that by expanding this analysis into multiple references. Due to the inherent difference of the samples, false positives would be introduced when using a single pair of sample and reference depending on the choice of the reference. Considering the trisomy samples will always have increased dosage of abnormal chromosomes, a one-sided t-test based on the Z-score was done and the results were controlled with regards to a false discovery rate. However, all these strategies would not eliminate the false positives from the pair-wise analysis (FIGS. 6a and 6b). FIGS. 6a and 6b show detection of trisomy 21 samples with pair-wise t-tests introduced false positives depending on the choice of reference (data from 4-plex flow cell 34). FIG. 6a shows a pair-wise two-sided t-tests had coupled false positives. The cells were highlighted for p-values <0.01. Trisomy 21 samples were bolded along the top row and left most column. FIG. 6b shows a false discovery rate controlled one-sided t-test was applied for the detection of increased dosage of chromosomes 21. These strategies reduced but did not eliminate the false positives. The cells were highlighted for q-values <0.05.

Figure 2:
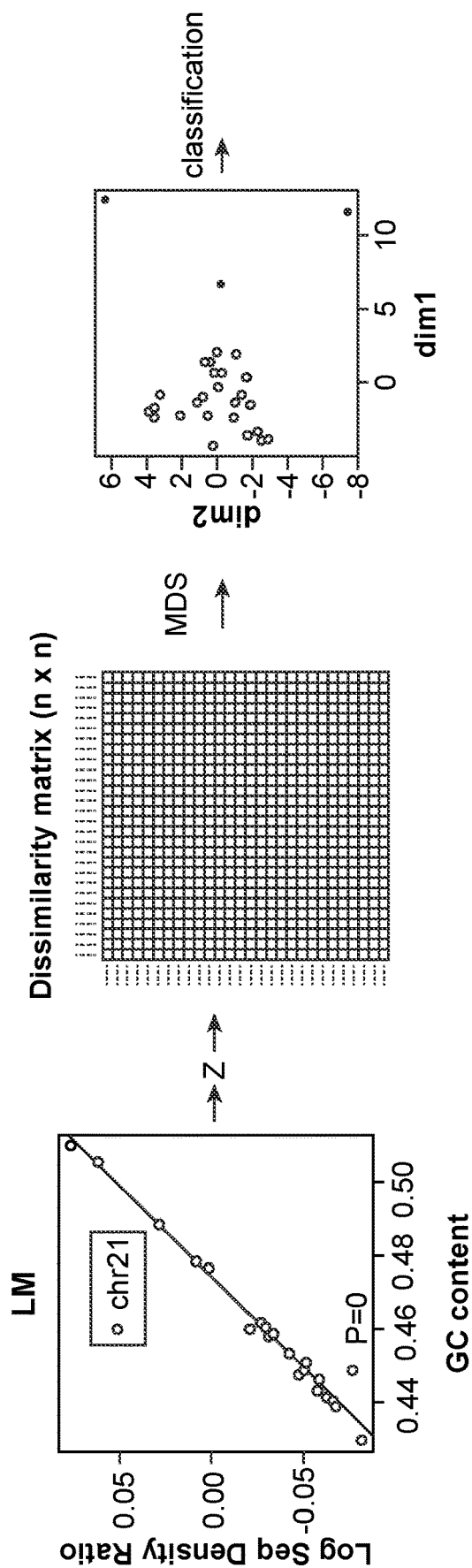
FIG. 2 shows a diagram of LM-MDS algorithm.

To increase the power of this test and maximize the utility of multiple reference samples, a novel algorithm was proposed for the detection of fetal aneuploidy (FIG. 2). FIG. 2 diagrams the Linear Model-Multidimensional Scaling algorithm. A Z-score can be derived from the linear relationship of the log sequence count ratio or total sequence counts and GC content for a test chromosome of each sample pair. The dissimilarity or Z-score is represented as the linear distance of a data point from linearity and is often the vertical distance of a point to a point on a line representing the linear relationship (FIG. 2, LM). The Z-score is calculated for all the sample pairs among the dataset to generate a dissimilarity matrix. A multidimensional scaling technique is used to reduce the dissimilarity matrix into two dimensional spaces. Classification techniques can then be applied to discriminate the trisomy samples from the normal samples.

The Z-score derived from the linear model can be considered as a standardized distance between two samples. After calculating the pair-wised Z-scores for the entire dataset, we derived an n X n dissimilarity matrix for the test chromosome. Multi-dimensional scaling technique was used to reduce this n×n matrix into two dimensional spaces. The trisomy samples and the normal samples spread according to their distance to each other. At this step, classification techniques, e.g., linear discriminant analysis, can be applied to separate these two classes.

Figure 3A:
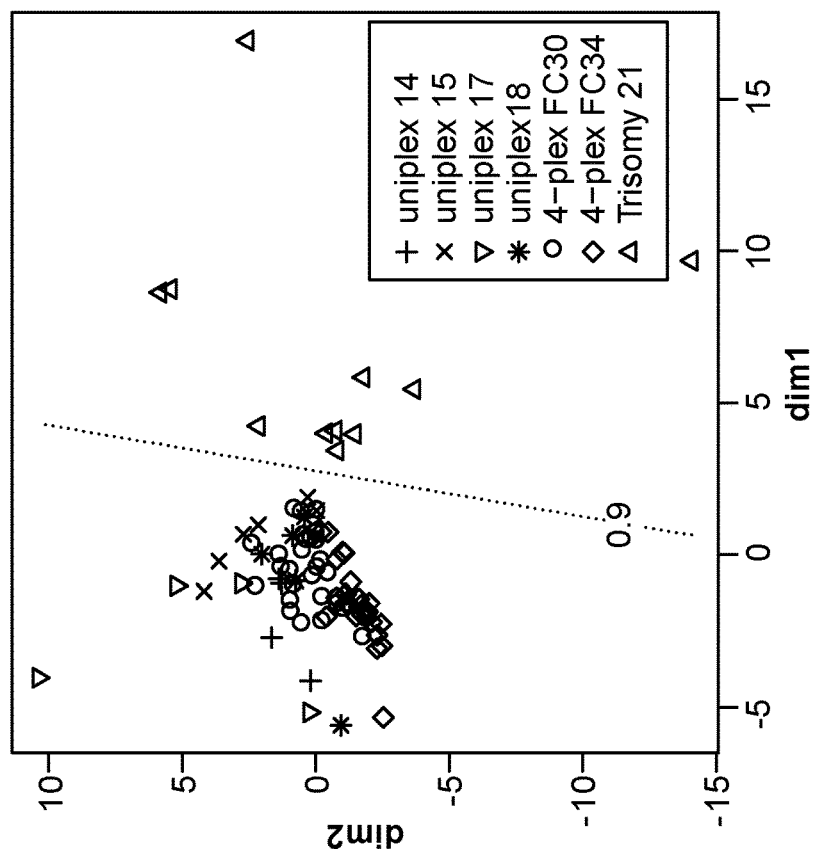
FIGS. 3a and 3b show LM-MDS transformed samples from different flow cells into the same space for classification.
Figure 7:
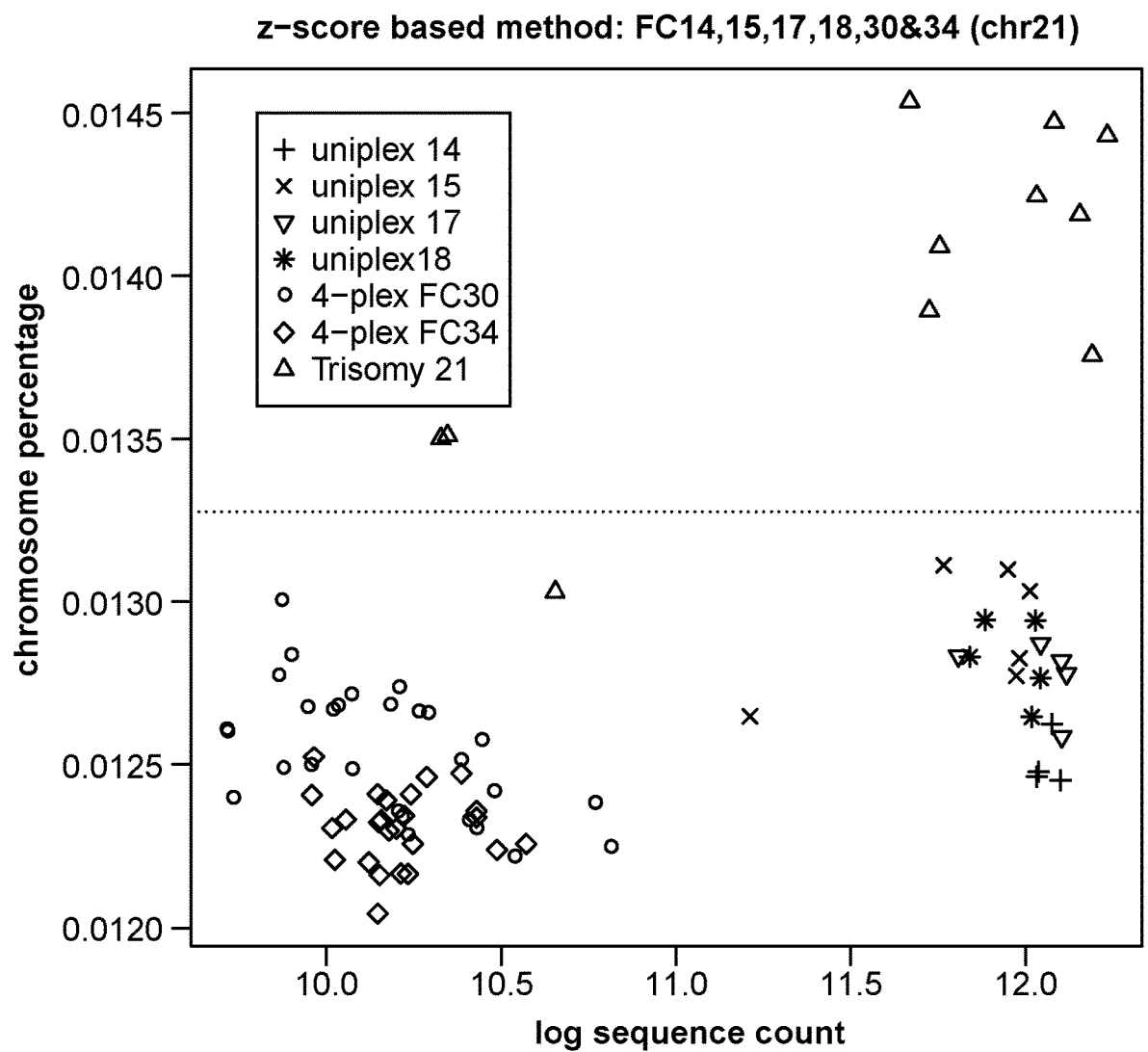
FIG. 7 shows a Z-score based method in detecting trisomy 21 samples.

The algorithm proposed, Linear Model-Multidimensional Scaling (LM-MDS), transformed the original t-test into a general classification solution. It largely expanded the applicability of the t-test, which might be biased with the choice of the reference. First this algorithm was applied into a combined analysis of two flow cells (FC), which were both 4-plex with 28 samples. FC34 had 3 trisomy 21 samples; FC30 were all normal samples. After applying LM-MDS, the samples from these two flow cells were presented in the same space (FIG. 3a). The normal samples tended to cluster together and the normal samples from the two flow cells largely overlapped. The 3 trisomy 21 samples spread far away from all the normal samples. A linear discriminant analysis (LDA) with posterior probability cutoff of 0.9 will easily differentiate the trisomy 21 samples from the normal samples. When the LM-MDS was applied to the rest of the chromosomes (chromosome 1 to chromosome 20 and chromosome 22), which are all disomy, all the samples from both flow cells tightly clustered together. These further proved the ability of LM-MDS to correct the GC and experimental bias in sequencing (FIG. 7). FIG. 7 shows LM-MDS on 4-plex flow cell 30 and 34. The 3 trisomy samples spread far away from the normal samples for chromosome 21 after LM-MDS transformation. The samples from the two flow cells overlapped and tightly clustered for the rest of the disomy chromosomes.

Figure 3B:
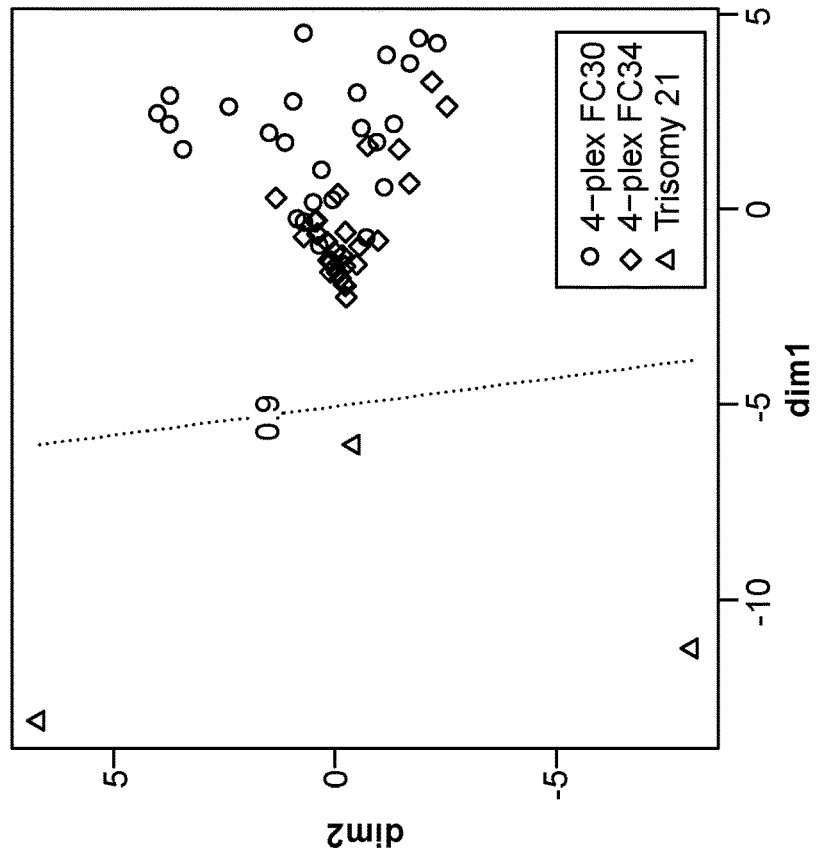

Next, we tested whether the LM-MDS algorithm could correct the experimental errors between different plex levels. Data was gathered from four uniplex and two 4-plex flow cells. After LM-MDS transformation, the normal samples from different plexes clustered closely and overlapped in one half of the space. The trisomy 21 samples clearly separated from the normal samples and sparsely spread on the other half of the space (FIG. 3b). This analysis clearly demonstrated the ability of LM-MDS algorithm to detect the trisomy samples with widely different experimental environments.

Performance of the LM-MDS Algorithm on Clinical Datasets of Fetal Trisomy 21

Figure 4:
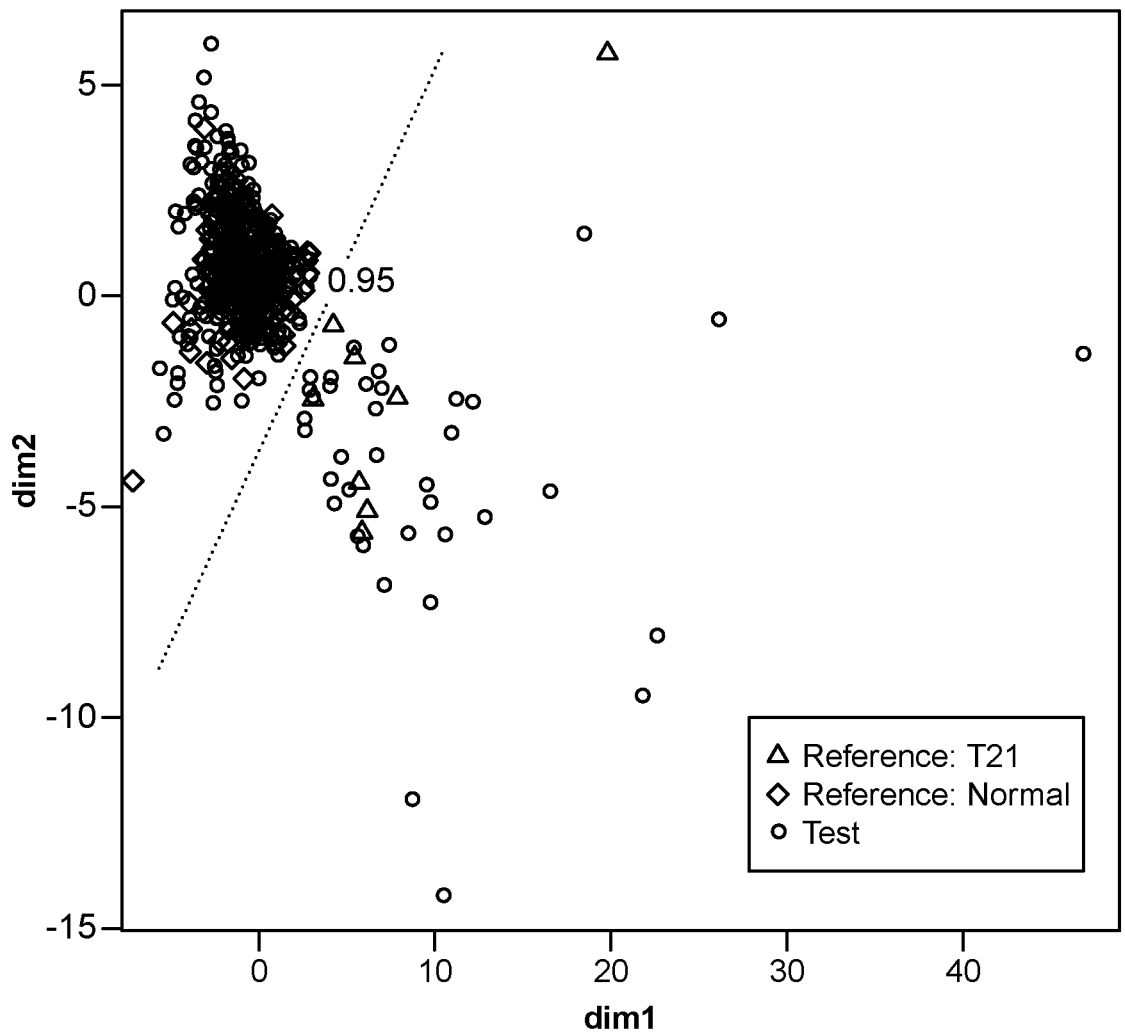
FIG. 4 shows a LM-MDS classification plot for the in-house dataset.

To test the clinical performance of the LM-MDS algorithm, two large scale clinical datasets were used. The first one was from the in-house study consisting of 480 samples, among which there were 42 trisomy 21 samples. This dataset was done in the format of 4-plex with an average sequence count of approximately 6 million per sample. The clinical information of the samples and the methods of sequencing were detailed elsewhere (Mathias Ehrich 2010). The LM-MDS algorithm was applied on all the applicable samples before and after the quality control metrics as stated (467 and 449 samples of each) (Mathias Ehrich 2010) and unsupervised learning was performed. The same 96 samples used in the internal quality control study (Mathias Ehrich 2010), which contained 8 trisomy 21 samples, were employed as the training set to derive the optimal classification rules. LM-MDS transformation was done on the training first and then the test set was projected onto the same sample space with the multidimensional scale technique. LDA was used on the training set to derive the decision boundary for classification. To match the original analysis settings (Mathias Ehrich 2010), the re-sequencing data in 4plex and uniplex (ten of each) was used to replace the original data. As demonstrated above, LM-MDS algorithm was able to analyze the data across plex levels; the uniplex samples were thus pooled with the 4 plex samples for a combined analysis. FIG. 4 illustrated the decision boundary from the training set and the classification of the two groups for the 449 samples after quality control. The trisomy and normal samples were clearly separately into two groups with the decision boundary of 0.95 posterior probability for the reference set. Of the total 39 trisomy 21 samples, only one trisomy 21 sample from the re-sequenced uniplex set was misclassified; all the normal samples were correctly identified. This resulted a sensitivity of 97.44% (95% CI: 86.82-99.55) and a specificity of 100% (95% CI: 99.07-100). The same analysis was done on the 467 set with all the applicable samples. There were a total of 41 trisomy samples in this set. The same T21 samples remained as false negatives. The resulting sensitivity and specificity were 97.56% (95% CI: 87.4-99.57) and 100% (95% CI: 99.11-100).

The second dataset was from personal communication with Dr. Y. M. Lo. There were a total of 753 samples (86 trisomy 21, 20 trisomy 13 and 42 trisomy 18). This experiment was done in 8-plex on an Illumina Genome Analyzer II. The averaged sequence count of each sample was approximately 0.4 million. The demographic information and clinical parameters for this dataset was detailed elsewhere. A supervised learning with the LM-MDS algorithm was first conducted.

Figure 5A:
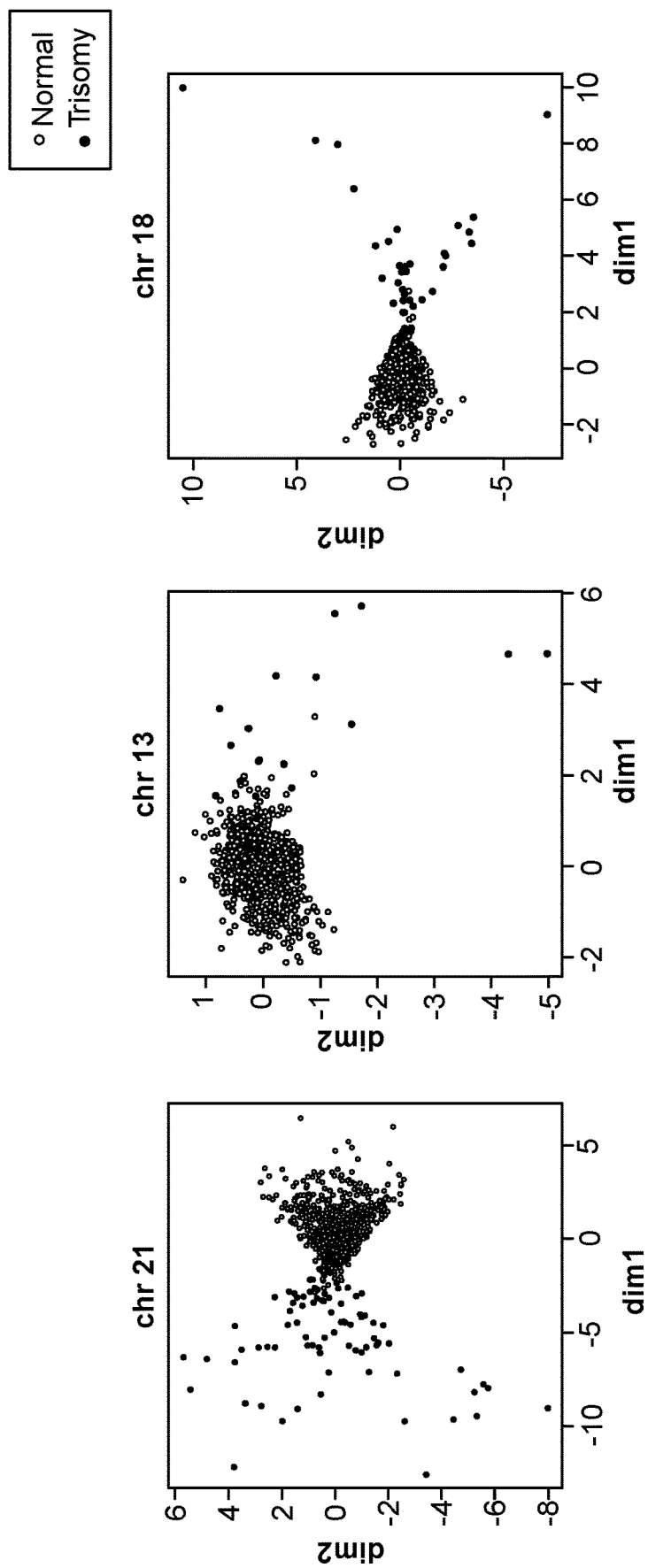
FIGS. 5a and 5b show LM-MDS classification for the Hong Kong dataset.

After LM-MDS transformation of the samples, the LDA was used again for the classification on the complete dataset. FIG. 5a illustrated the plot of this dataset represented in two dimensional spaces after LM-MDS transformation. The trisomy 21 samples are largely separated from the normal samples in the bipolar shape with a few samples overlapping. Maximizing sensitivity and specificity, a sensitivity of 95.35% (95% CI: 88.64-98.18) and a specificity of 97.30% (95% CI: 95.77-98.29) was achieved with the LDA classification. To access the diagnostic power of this algorithm on a novel dataset, a leave-one-out cross-validation analysis on this dataset was performed. The sensitivity and specificity were each 93.02% (95% CI: 85.6-96.76) and 97.30% (95% CI: 95.77-98.29) (Table 1).

Detection Fetal Trisomies 13 and 18 with LM-MDS

Figure 5B:
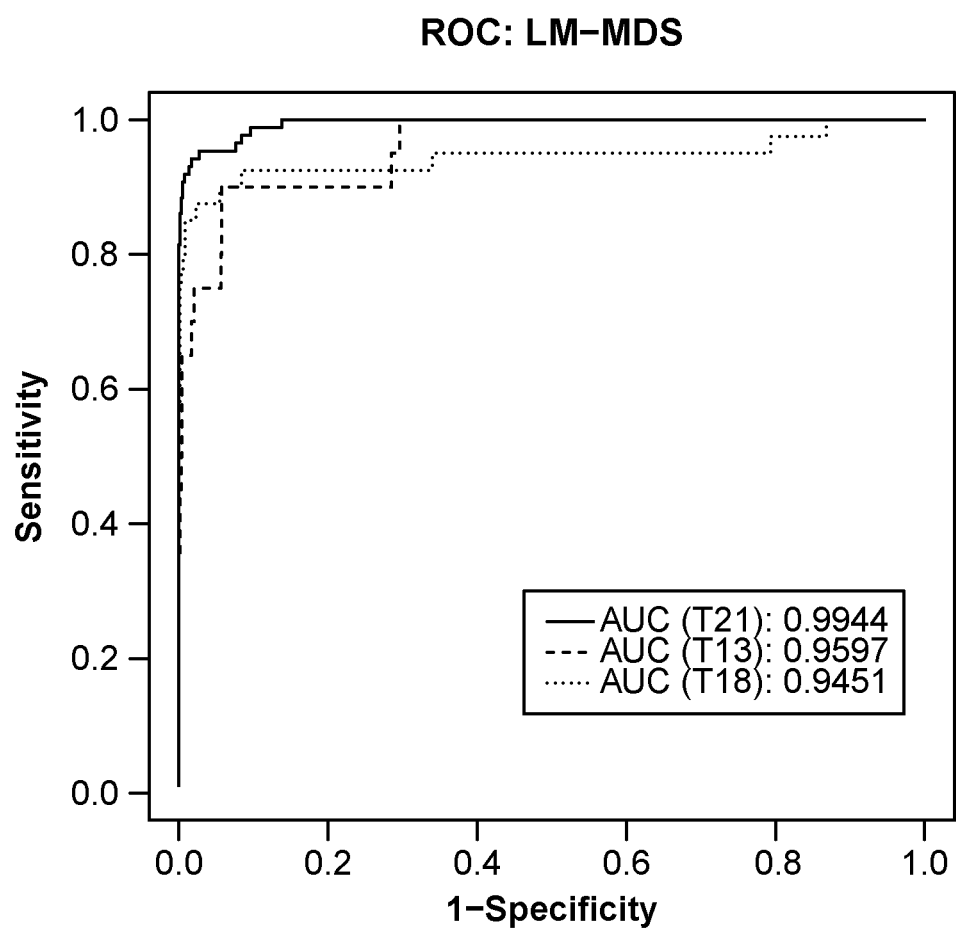

The LM-MDS algorithm can also be applied for the detection of trisomies 13 and 18. Using the Hong Kong dataset as a test, a similar analysis procedure was performed on chromosomes 13 and 18. The sequence percentage of chromosomes 13 and 18 was discovered to have a higher coefficient of variation than that of chromosome 21. This would lead to poor detection results for trisomies 13 and 18 if using prior Z-score based methods. Also observed was more overlap of the trisomies 13 and 18 samples with the normal samples than trisomy 21 (FIG. 5a, trisomy samples: black circle; normal samples: grey circle.). However, 90% and 87.5% sensitivity for chromosomes 13 and 18, respectively, in the supervised learning was still achieved. The classification results on the complete dataset and the results for leave-one-out cross validation are summarized in Table 1. The higher sequencing variations in chromosomes 13 and 18 may be due to the intrinsic characteristics related to the chromosome specific structure or contents. For comparison, a ROC analysis on the Hong Kong dataset for these three chromosomes was performed (FIG. 5b). The area-under-curve (AUC) values for chromosome 21 was close to 1 and were around 0.95 for chromosomes 13 and 18. This result further demonstrated the LM-MDS algorithm as a strong classifier in fetal aneuploidy diagnostic.

Example 3: Fetal Aneuploidy Discussion

Herein is illustrated a novel algorithm in transforming the fetal aneuploidy diagnosis into a classical classification solution with sequencing technology. The utility of this linear-model based algorithm in detecting fetal aneuploidy in large clinical datasets with high accuracy is demonstrated. This algorithm was also applicable for the diagnosis of trisomies 21, 13 and 18. Unlike the common feature-based classification, dissimilarity-based classification offers opportunities when the original data cannot have proper attributes built. Here, the pair-wise calculation of the Z-score from the LM built up a dissimilarity matrix for classification. The given dissimilarity matrix can be used directly to build the classifier, however, it has been suggested that when only n samples are available in an n-dimensional space, reduction of the dimensionality is important to improve the performance of the feature-based classifiers (Elzbieta Pekalska 2000). For the n-dimensional space, there could be different n×m (m<n) reduced versions. m equals 2 was used for simplicity and easy visualization. After the transformation of the dissimilarity matrix by multidimensional scaling, various classification methods can be applied for the differentiation of the trisomy samples from the normal ones. In the 2-dimension space resulting from MDS, the samples spread according to their distance to each other. A bipolar spread of the samples was observed; a linear discriminant analysis would be a straight-forward classifier for this problem. For the datasets tested, the linear discriminant analysis served as a satisfactory classier. Logistic regression or other more advanced classifiers like classification trees or support vector machines may be good alternatives.

Figure 8:
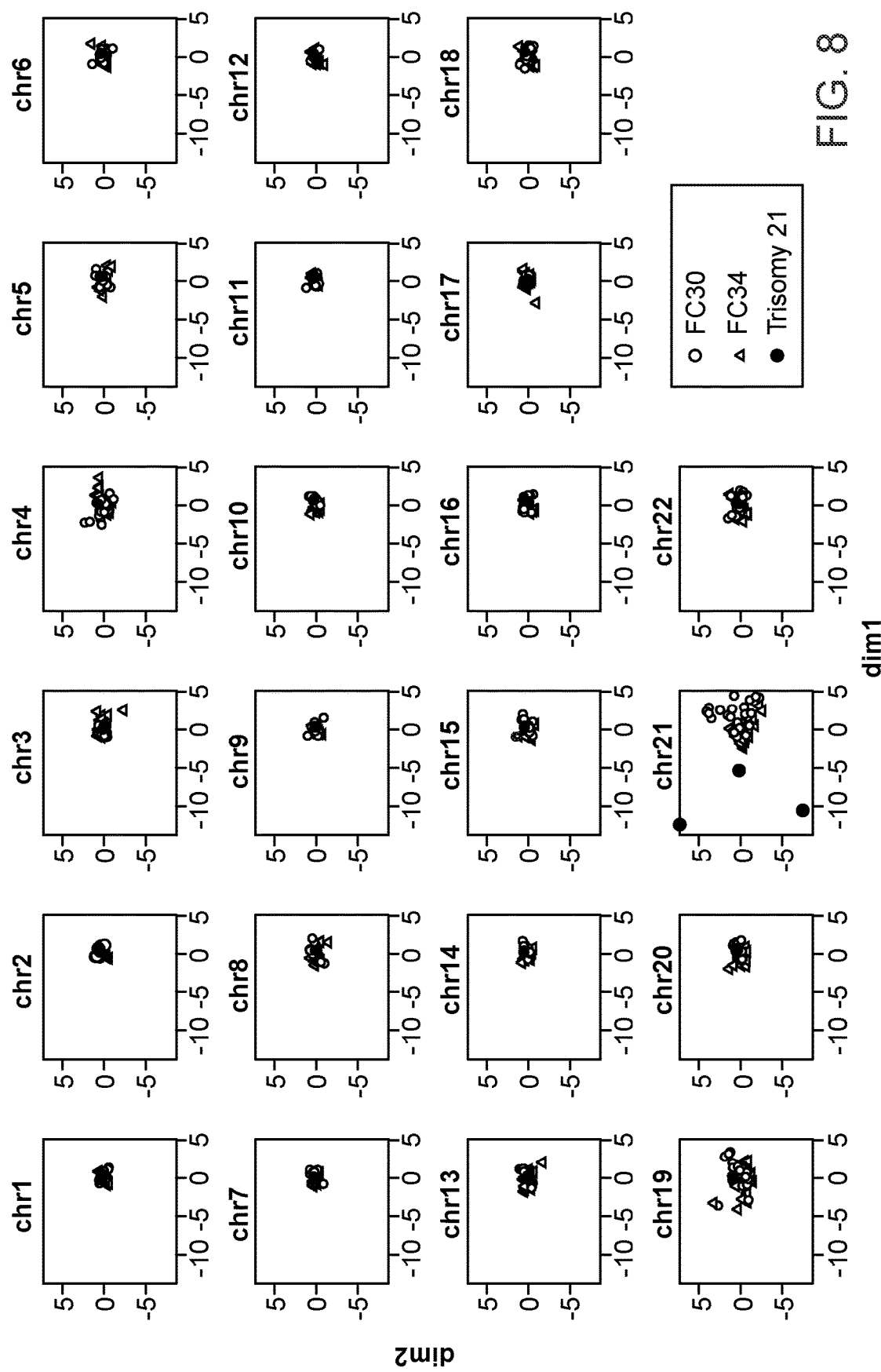
FIG. 8 shows LM-MDS on 4-plex flow cell 30 and 34.

The diagnostic method based on Z-score was used in several studies for detecting fetal aneuploidy with sequencing technology. However this method did not account for the GC bias and experimental batch effects. The chromosome 21 percentage was plotted against the logged sequence count for the same uniplex and 4 plex dataset used in FIG. 3 and FIG. 8 (FIG. 7). A Z-score-based method is calculated from the chromosome percentage and normalized by the mean and standard deviation of the reference samples (Chiu, Chan et al. 2008). To explore the potential bias from the choice of different reference samples, we plotted the chromosome 21 percentage for the uniplex 14,15, 17,18 and 4-plex 30 and 34 (FIG. 7). The dotted line is calculated from the median plus 3-folds of median absolute deviation of all the normal samples, which mimic the Z-score cut-off of 3 that YM Lo applied (data from the Lo set). Experimental batch effects are clear in the plex level and in different flow cells. This would lead to false positives depending on the choice of different reference sets. It is clear that the chromosome percentage had a batch effect from different flow cell to flow cell and the uniplex samples had significantly higher chromosome percentage than 4 plex samples (p-value=0.000012). This could jeopardize the diagnostic results if a different flow cell was used as reference for the Z-score calculation. However, the LM-MDS algorithm would take this experimental batch effect into consideration. The LM-MDS algorithm also demonstrated the ability to correct the batch effect from flow cell to flow cell and even across the plex levels. FIG. 3 shows LM-MDS transformed samples from different flow cells into the same space for classification. FIG. 3a shows two 4-plex flow cells were transformed by LM-MDS. LDA analysis classified trisomy 21 samples separately from the normal samples. FIG. 3b shows that LM-MDS was able to transform the samples from different plex levels into the same space for easy classification. FIG. 8 shows LM-MDS transformation of samples from two 4-plex flow cells on all the chromosomes. The trisomy samples only separated from the rest of the euploid samples in the transformation plot of chromosome 21; but largely overlap with the euploid samples in all the rest chromosomes. This further demonstrates the specificity of the LM-MDS transformation on detecting the trisomy 21samples.

Figure 9A:
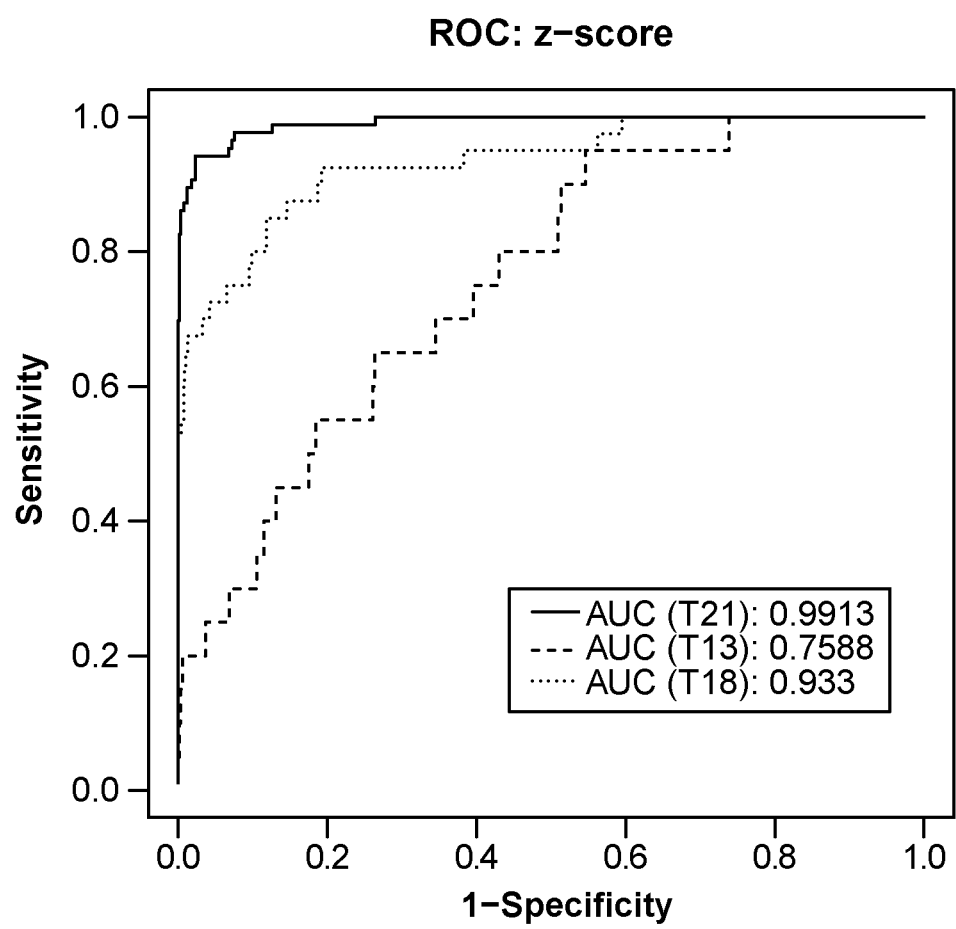
FIGS. 9a and 9b show ROC (Receiver Operating Characteristic) plots for classification with Z-score based method.
Figure 9B:
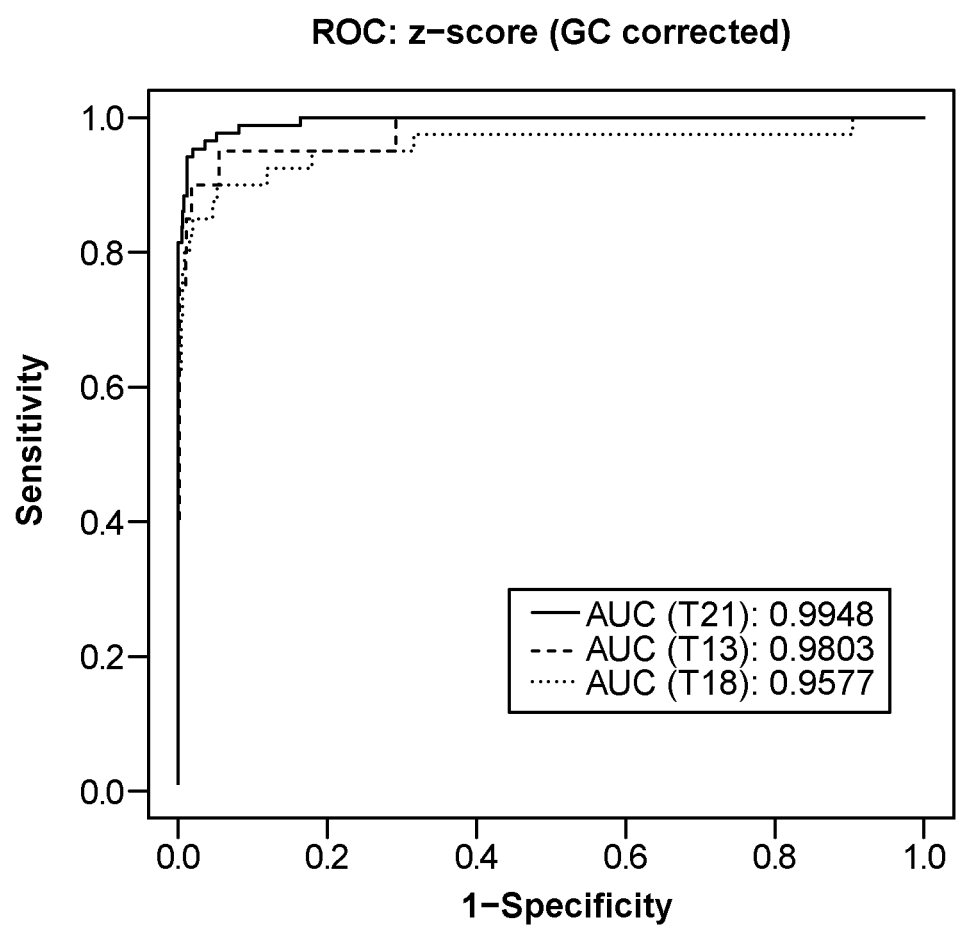

The Z-score based method commonly employed a statistically significant cutoff of 3 to differentiate the trisomy samples from the normal samples. This required a big sampling number of the two distributions of normal and trisomy samples to achieve the high sensitivity. When the sequence count was reduced (averaged approximately 0.4 million in 8 plex Hong Kong dataset), the Z-score of 3 would no longer be the optimal cutoff: a Z-score of 3 resulted in a sensitivity of 87.2% and specificity of 98.9% for trisomy 21; however, the cutoff of 2.439 would have the maximum sensitivity and specificity of 94.2% and 97.4% for each (Z-score calculated for 657 samples of the Hong Kong dataset; the rest of the 96 diploid samples were used as reference set). ROC analysis was performed on the Z-score based method in detecting trisomy samples (FIG. 9a). Although the AUC value was similar for the Z-score based method and the LM-MDS algorithm for detecting trisomy 21, the LM-MDS algorithm would provide the most flexibility to obtain the optimal classification decisions. The same procedure was performed on the Hong Kong dataset on chromosomes 13 and 18. When comparing the detection power of these two methods for trisomies 13 and 18, the advantage in the LM-MDS algorithm was clear after compensating for the GC bias and experimental batch effect (FIG. 9a). The Z-score, using GC normalized sequence count by LOESS technique, led to improved results for trisomies 13 and 18 compared with the uncorrected Z-score (FIG. 9b). The results were comparable to the LM-MDS algorithm. Again, as stated, they lacked the flexibility for the selection of optimal cutoffs.

Another sequencing-based method for detecting fetal aneuploidy was from SR Quake's group (Fan and Quake 2010). After they corrected the GC amplification bias and normalized the sequence count within the whole dataset, they found that the distribution of the sequence count of 50 kb bins for each chromosome followed a Poisson distribution. Instead of relying on different sample as a reference, they directly compared the median sequence count of the 50 kb bins of chromosome 21 with the rest of the chromosomes of the same sample and came up with a t-test for the significant test. When we tested their method, we found that the establishment of a Poisson distribution they described was sensitive to the normalization dataset chosen, thus it made this method less robust in a large dataset.

Several research groups have reported a positive GC bias for the Illumina (Solexa) sequencing platform. The bias can be either a positive or a negative one depending on the different sequencing platforms (Chiu, Sun et al.; Chiu, Chan et al. 2008; Fan, Blumenfeld et al. 2008). To investigate this problem, the sequence tag counts were examined per 50 kb bin versus its GC content across the genome for all the samples. It was discovered that the GC bias introduced in the sequencing amplification could be different even on the same platform of Illumina Genome Analyzer IIx, depending on the difference of chemistry used in the library preparation (data not shown). A prior linear model assumed the same GC function in different samples when comparing the sequence count ratio. It would be good practice to check the GC bias in different batches of dataset before applying the LM-MDS for further analysis.

The fetal DNA percentage of maternal plasma samples is easy to understand as a limiting factor in differentiation of the overrepresentation of the trisomy chromosomes in the maternal genomes. Typically, fetal DNA fraction account for approximately 3 to approximately 20% of the total DNA in a maternal plasma sample (Stanghellini, Bertorelli et al. 2006; Zimmermann, Zhong et al. 2007; Lun, Chiu et al. 2008). Here, for the in-house study of 480 samples, we quantified the fetal DNA fraction with an independent assay (Nygren, Dean et al., 2010) in parallel with the sequencing study. The averaged fetal DNA fraction of the 467 samples studied was 0.135 with a range of 0.02 to 0.5. With the sequence depth of approximately 6 million counts per samples, there was only one sample misclassified to be a false negative with the LM-MDS method. The estimated fetal fraction for this sample was 0.03. The failure of LM-MDS to classify this sample was not to be blamed on the low fetal fraction as all the rest of the samples with low fetal DNA fractions (totally 10 samples with fetal fraction lower or equal to 0.03) were correctly classified. In the work of Fan C et al, they also explored the relationship between the sequencing depth, fetal DNA fraction and sensitivity of the diagnostic ability of their method (Fan and Quake 2010). We agreed with the authors that sequencing depth would be a vital factor in determining the sensitivity of the diagnostic test. With the same sequencing depth, the LM-MDS algorithm has achieved higher sensitivities at the same fetal DNA fraction level than the theoretical ones in the method Fan et al proposed.

The LM-MDS algorithm has laid down the grounds for the classification solutions for fetal aneuploidy detection. It also opened doors for the medical problems which are hard to formulate proper attributes to, but have simple standard tests on pair-wise samples. By incorporating the GC bias and experimental bias correction into the study model, the LM-MDS algorithm offered a flexible classification solution for the better detection of fetal aneuploidy.

Example 4: Fetal Aneuploidy Data

TABLE 1

Clinical performance of LM-MDS for detecting fetal aneuploidy on the Hong Kong dataset. The LM-MDS algorithm was applied onto chromosomes 21, 13 and 18 for the detection of trisomy samples. The diagnostic results for the supervised classification and leave-one-out cross-validation were summarized.

| Chromo-some | N | Tri-somy | Supervised Learning | | LOOCV | |
|---|---|---|---|---|---|---|
| | | | Sensitivity (95% CI) | Specificity 95% CI) | Sensitivity (95% CI) | Specificity (95% CI) |
| 21 | 753 | 86 | 95.35% (88.64-98.18) | 97.30% (95.77-98.29) | 93.02% (85.6-96.76) | 97.30% (95.77-98.29) |
| 13 | 753 | 20 | 90% (69.9-97.21) | 94.27% (92.35-95.73) | 70% (48.1-85.45) | 92.36% (90.21-94.07) |
| 18 | 753 | 42 | 87.5% (73.89-94.54) | 97.76% (96.39-98.61) | 77.5% (62.5-87.68) | 97.48% (96.04-98.4) |

Example 5: Fetal Gender Prediction and Fetal Fraction Estimation

Method

The LM was expanded to detect the fetal gender. Every sample pair was plugged in the LM using chromosome1-X. The controlled p-values were calculated for chromosome X in a one-sided test. The female euploidy samples in the reference set (n=48) were used to test the loss of the dosage of chromosome X; the male euploidy sample in the reference set (n=48) were used to test the gain of the dosage of chromosome X. Here, we employed a scheme of majority vote. The cut-off for the p-value was set to an empirical value of 0.05. The sample was called as female if it had more significant tests in the male reference set; or a male if it had more significant tests in the female reference set. No gender information would be reported if the votes tied between the male reference and female reference.

For the estimation of the fetal fraction, the log sequence tag count ratio and GC percentage of each chromosome were plugged into the linear model to detect the depletion of chromosome X (Chu, Bunce et al. 2009). The male samples from the in-house 480 study were compared against the female samples from the same dataset and the female samples from the reference set. The fetal fraction (f) was calculated from the deviation of the chromosome X from the expected position (Y) to the observed position ($\mu$) in the linear model:

$$f = 2X(1 - e^{|\mu - Y|}) \quad \text{(Equation 1)}$$

The averaged estimation from all the reference samples was used for the final fetal fraction.

Example 6: Fetal Gender Prediction and Fetal Fraction Estimation Results

Figure 10:
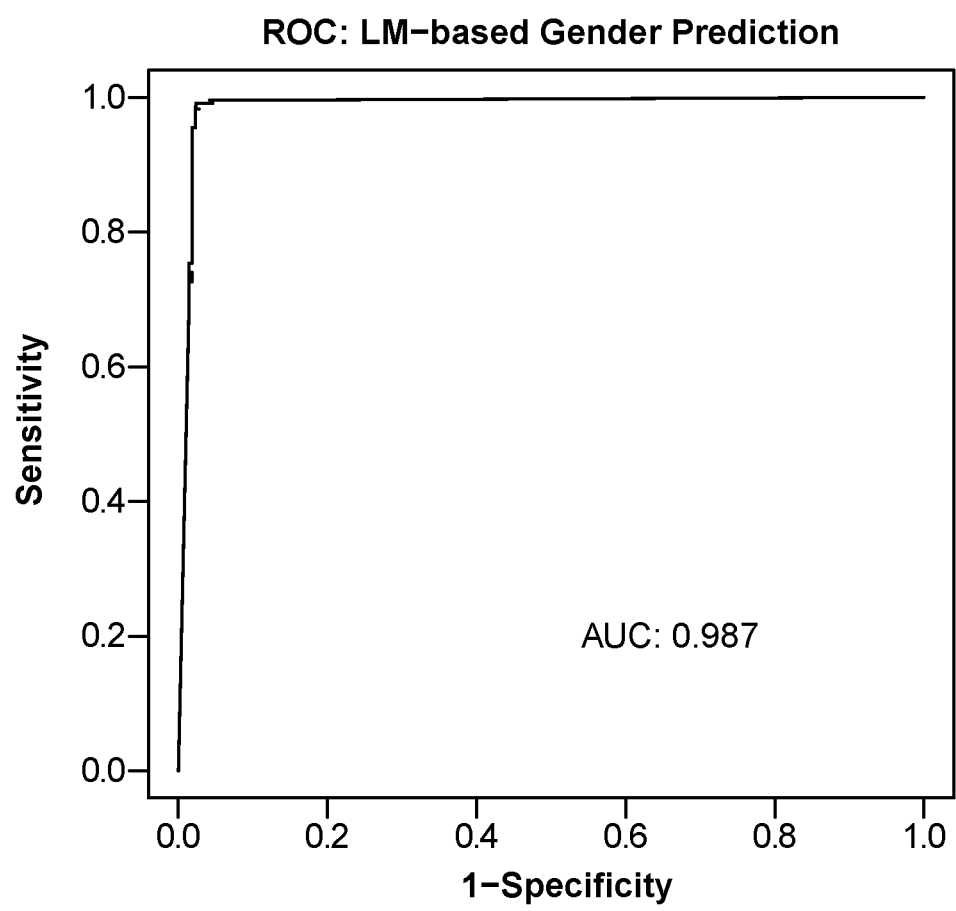
FIG. 10 shows a ROC plot of LM-based gender prediction.

The same concept of detecting the abnormality of trisomy 21 can also be extended to capture the depletion of the chromosome X for male fetus when comparing with the samples with female fetus. This information can be used to detect the gender information. The in-house 480 dataset was again used to test the LM-based method of gender detection. The 96 samples used in (Mathias Ehrich 2010) and used in the LM-MDS classification, which included 48 females and 48 males, were also used as reference here to detect the gender status. Among the 467 test samples, the gender information was available for 442 of them. There was only one sample reported as NA (Not Applicable) by the LM based method of gender prediction. The confusion matrix of the gender prediction with the LM-based method was summarized in Table 1. The accuracy of the prediction is 98.19% with a 95% confidence interval of 96.46%-99.08%. Nygren et al developed a gender prediction method using the chromosome specific marker SRY (Nygren, Dean et al., 2010). The SRY marker was also measured for the samples of in-house 480 study. The gender prediction using the SRY marker had an accuracy of 98.87% (95% CI: 97.38%-99.52%). The sample with gender reported as NA could be easily resolved by increasing the cut-off p-value a little bit higher to include more votes from each reference group. Using a p-value cut-off of 0.06, this sample was correctly called as a male. In an ad hoc ROC analysis, the best cut-off with highest accuracy and all the samples included was 0.066. This would lead to an accuracy of 97.96% (95% CI: 96.18%-98.93%). The area-under-curve (AUC) value was 0.987 for this method (FIG. 10). Using the sequencing information alone, the LM-based method has achieved comparable performance as the independent experimental procedures.

Figure 11:
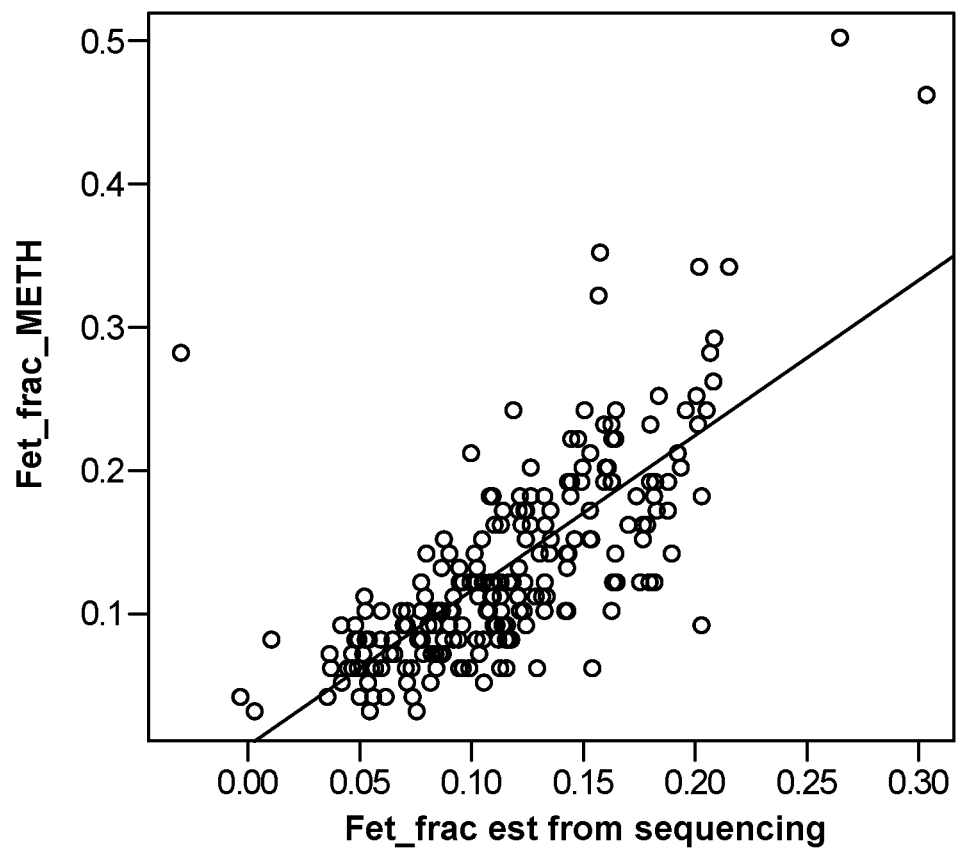
FIG. 11 shows fetal fraction estimate from sequencing.

From the linear model, when male samples were compared with female sample, the fetal fraction information can also be calculated from the deviation of the chromosome X from the expected position to the observed position in the linear model. To explore the accuracy of this method, we used the samples from the in-house 480 study with known fetus gender information. There were a total of 217 male samples and 225 female samples in this set (467 samples); the rest of the samples were missing the fetus gender information. The fetal fraction estimated with the sequencing data was compared with an independent method with the methylation markers (Nygren, Dean et al., 2010). The two measurements exhibited a high correlation of 0.739 (p-value <2.2×10-16) (FIG. 11). The fetal fraction estimated with the methylation marker tended to have higher fetal fraction detected with larger amount of fetal materials present (range in approximately 0.03-0.35). Except for a few outliers, the fetal fraction estimated with the sequencing method fell into the range of approximately 0.03-0.2. This was in accordance with the current knowledge on fetal fraction (Stanghellini, Bertorelli et al. 2006; Zimmermann, Zhong et al. 2007; Lun, Chiu et al. 2008). To test whether the method we employed here was robust regarding the choice of reference, we also estimated the fetal fraction using an external female reference (n=48) and achieved very close results (correlation=1, p-value <2.2×10-16).

Example 7: Fetal Gender Prediction and Fetal Fraction Estimation Discussion

Based on the linear model, we proposed a scheme for fetus gender prediction. The accuracy of this in silico method has achieved compatible performance as the experimental procedure based on chromosome Y specific marker. We also proposed a computational method to estimate the fetal fraction from the sequencing data alone. Comparing with the fetal fraction measurement with the methylation markers, the results with the sequencing-based method was in accordance with the reported fetal fraction range, especially when there is large amount of fetal material present.

TABLE 2

Confusion matrix for the gender prediction with LM-based method (n = 441). LM, linear model based gender prediction using sequencing information.

|    |   | Truth |     |
|----|---|-------|-----|
|    |   | X     | Y   |
| LM | X | 223   | 6   |
|    | Y | 2     | 211 |

Listing of Documents Cited

Chim, S. S., S. Jin, et al. (2008). "Systematic search for placental DNA-methylation markers on chromosome 21: toward a maternal plasma-based epigenetic test for fetal trisomy 21." Clin Chem 54 (3): 500-11.

Chiu, R. W., K. C. Chan, et al. (2008). "Noninvasive prenatal diagnosis of fetal chromosomal aneuploidy by massively parallel genomic sequencing of DNA in maternal plasma." Proc Natl Acad Sci USA 105 (51): 20458-63.

Chiu, R. W., H. Sun, et al. "Maternal plasma DNA analysis with massively parallel sequencing by ligation for non-invasive prenatal diagnosis of trisomy 21." Clin Chem 56 (3): 459-63.

Chu, T., K. Bunce, et al. (2009). "Statistical model for whole genome sequencing and its application to minimally invasive diagnosis of fetal genetic disease." Bioinformatics 25 (10): 1244-50.

Dohm, J. C., C. Lottaz, et al. (2008). "Substantial biases in ultra-short read data sets from high-throughput DNA sequencing." Nucleic Acids Res 36 (16): e105.

Elzbieta Pekalska, R. P. W. D. (2000). Classifiers for dissimilarity-based pattern recognition. 15th International Conference on Pattern Recognition (ICPR'00), Barcelona, Spain Fan, H. C., Y. J. Blumenfeld, et al. (2008). "Noninvasive diagnosis of fetal aneuploidy by shotgun sequencing DNA from maternal blood." Proc Natl Acad Sci USA 105 (42): 16266-71.

Fan, H. C. and S. R. Quake (2010). "Sensitivity of noninvasive prenatal detection of fetal aneuploidy from maternal plasma using shotgun sequencing is limited only by counting statistics." PLOS One 5 (5): e10439.

Lo, Y. M., N. Corbetta, et al. (1997). "Presence of fetal DNA in maternal plasma and serum." Lancet 350 (9076): 485-7.

Lo, Y. M., F. M. Lun, et al. (2007). "Digital PCR for the molecular detection of fetal chromosomal aneuploidy." Proc Natl Acad Sci USA 104 (32): 13116-21.

Lo, Y. M., N. B. Tsui, et al. (2007). "Plasma placental RNA allelic ratio permits noninvasive prenatal chromosomal aneuploidy detection." Nat Med 13 (2): 218-23.

Lun, F. M., R. W. Chiu, et al. (2008). "Microfluidics digital PCR reveals a higher than expected fraction of fetal DNA in maternal plasma." Clin Chem 54 (10): 1664-72.

Mathias Ehrich, C. D., Tricia Zwiefelhofer, John Tynan, Lesley Cagasan, Roger Tlm, Vivian Lu, Ron Mccullough, Erin Mccarthy, Anders Nygren, Jarrod Dean, Lin Tang, Don hutchinson, Tim Lu, Tom Wang, Vach Angkachatchai, Paul Oeth, Charles R. Cantor, Allan Bombard, Dirk van den Boom. (2010). "Toward implementation of next-generation sequencing based non-invasive prenatal fetal aneuploidy detection in a clinical laboratory.".

Ng, E. K., N. B. Tsui, et al. (2003). "mRNA of placental origin is readily detectable in maternal plasma." Proc Natl Acad Sci USA 100 (8): 4748-53.

Nygren, A. O., J. Dean, et al. (2010) "Quantification of fetal DNA by use of methylation-based DNA discrimination." Clin Chem 56 (10): 1627-35.

Old, R. W., F. Crea, et al. (2007). "Candidate epigenetic biomarkers for non-invasive prenatal diagnosis of Down syndrome." Reprod Biomed Online 15 (2): 227-35.

Oudejans, C. B., A. T. Go, et al. (2003). "Detection of chromosome 21-encoded mRNA of placental origin in maternal plasma." Clin Chem 49 (9): 1445-9.

Sherman, S. L., E. G. Allen, et al. (2007). "Epidemiology of Down syndrome." Ment Retard Dev Disabil Res Rev 13 (3): 221-7.

Shin, M., L. M. Besser, et al. (2009). "Prevalence of Down syndrome among children and adolescents in 10 regions of the United States." Pediatrics 124 (6): 1565-71.

Stanghellini, I., R. Bertorelli, et al. (2006). "Quantitation of fetal DNA in maternal serum during the first trimester of pregnancy by the use of a DAZ repetitive probe." Mol Hum Reprod 12 (9): 587-91.

Tabor, A., J. Philip, et al. (1986). "Randomised controlled trial of genetic amniocentesis in 4606 low-risk women." Lancet 1 (8493): 1287-93.

Zimmermann, B., X. Y. Zhong, et al. (2007). "Real-time quantitative polymerase chain reaction measurement of male fetal DNA in maternal plasma." Methods Mol Med 132:43-9.

Example 8: Example of Embodiments

Provided hereafter are non-limiting example of certain embodiments of the technology.

A1. A method for non-invasive assessment of a genetic variation comprising:
(a) identifying one or more dissimilarities for a feature between a subject data set and a reference data set by a statistical analysis wherein the subject data set comprises genomic nucleic acid sequence information of a sample from a subject and the reference data set comprises genomic nucleic acid sequence information of a biological specimen from one or more reference persons;
(b) generating a multidimensional matrix from the dissimilarities;
(c) reducing the multidimensional matrix into a reduced data set representation of the matrix;
(d) classifying into one or more groups the reduced data set representation by one or more linear modeling analysis algorithms thereby providing a classification; and
(e) determining the presence or absence of a genetic variation for the sample based on the classification.

A1a. The method of embodiment A1, further comprising obtaining genomic nucleic acid sequence information of a sample from a subject and obtaining genomic nucleic acid sequence information of a biological specimen from one or more reference persons.

A2. The method of embodiment A1, further comprising receiving the subject data set and the reference data set.

A3a. The method of embodiment A1, wherein the genetic variation is a fetal aneuploidy.

A3b. The method of embodiment A1, wherein the genetic variation is a fetal gender.

A3c. The method of embodiment A1, wherein the genetic variation is a fetal fraction estimation.

A4. The method of any one of embodiments A3a-A3c, wherein the subject is a pregnant female and the reference persons are pregnant females.

A5. The method of any one of embodiments A1 to A3c, wherein the reference persons do not include the subject.

A6. The method of any one of embodiments A1 to A5, wherein the reference data set comprises genomic nucleic acid sequence information of a biological specimen from one or more reference persons and the subject.

A7. The method of any one of embodiments A1 to A6, wherein the sample is blood serum or blood plasma from the subject.

A8. The method of embodiment A1, wherein the genomic nucleic acid sequence information is from a multiplex sequence analysis.

A9. The method of embodiment A1, further comprising reiterating identification of the one or more dissimilarities in a pairwise analysis between each pair in the subject data set and the reference data set.

A10. The method of embodiment A1, wherein the subject data set and the reference data set comprise a fluorescent signal or sequence tag information.

A11. The method of embodiment A10, further comprising quantifying the signal or tag using a technique selected from the group consisting of flow cytometry, quantitative polymerase chain reaction (qPCR), gel electrophoresis, genechip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

A12. The method of embodiment A1, wherein the statistical analysis is selected from the group consisting of decision tree, counternull, multiple comparisons, omnibus test, Behrens-Fisher problem, bootstrapping, Fisher's method for combining independent tests of significance, null hypothesis, type I error, type II error, exact test, one-sample Z test, two-sample Z test, paired Z-test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, and combination thereof.

A13. The method of embodiment A1, wherein the method for reducing the multidimensional matrix is selected from the group consisting of metric and non-metric multidimensional scaling, Sammon's non-linear mapping, principal component analysis and combinations thereof.

A14. The method of embodiment A1, wherein the linear modeling analysis algorithm is selected from the group consisting of analysis of variance, Anscombe's quartet, cross-sectional regression, curve fitting, empirical Bayes methods, M-estimator, nonlinear regression, linear regression, multivariate adaptive regression splines, lack-of-fit sum of squares, truncated regression model, censored regression model, simple linear regression, segmented linear regression, decision tree, k-nearest neighbor, supporter vector machine, neural network, linear discriminant analysis, quadratic discriminant analysis, and combinations thereof.

A15. The method of any one of embodiments A3a to A14, wherein the reference data set comprises features from pregnant females who are between 25 years old and 30 years old.

A16. The method of any one of embodiments A3a to A14, wherein the reference data set comprises features from pregnant females who are between 30 years old and 35 years old.

A17. The method of any one of embodiments A3a to A14, wherein the reference data set comprises features from pregnant females who are between 35 years old and 40 years old.

A18. The method of any one of embodiments A3a to A14, wherein the reference data set comprises features from pregnant females who are in the first trimester of pregnancy.

A19. The method of any one of embodiments A3a to A14, wherein the reference data set comprises features from pregnant females who are in the second trimester of pregnancy.

A20. The method of any one of embodiments A3a to A14, wherein the subject data set comprises features from pregnant females who are in the first trimester of pregnancy.

A21. The method of embodiment A20, wherein the reference data set comprises features chosen from one or more of a physiological condition, genetic or proteomic profile, genetic or proteomic characteristic, response to previous treatment, weight, height, medical diagnosis, familial background, results of one or more medical tests, ethnic background, body mass index, age, presence or absence of at least one disease or condition, species, ethnicity, race, allergies, gender, presence or absence of at least one biological, chemical, or therapeutic agent in the subject, pregnancy status, lactation status, medical history, blood condition, and combinations thereof.

A22. The method of embodiment A1, wherein a statistical sensitivity and a statistical specificity is determined from the classified reduced data set representation.

A23. The method of embodiment A22, wherein the statistical sensitivity and statistical specificity are independently between 90% and 100%.

A24. A method for non-invasive assessment of a genetic variation comprising:
(a) obtaining a subject data set comprising genomic nucleic acid sequence information of a sample from a subject;
(b) obtaining a reference data set comprising genomic nucleic acid sequence information of a biological specimen from one or more reference persons;
(c) identifying one or more dissimilarities for a feature between the subject data set and the reference data set by a statistical analysis;
(d) generating a multidimensional matrix from the dissimilarities;
(e) reducing the multidimensional matrix and transforming the matrix into a reduced data set representation of the matrix;
(f) classifying into one or more groups the reduced data set representation by one or more linear modeling analysis algorithms thereby providing a classification; and
(g) determining the presence or absence of a genetic variation for the sample based on the classification.

A25. A method for non-invasive assessment of fetal gender or fetal fraction estimation comprising:
(a) receiving a subject data set comprising genomic nucleic acid sequence information of a biological specimen sample from a subject;

(b) receiving a reference data set comprising genomic nucleic acid sequence information of a biological specimen from one or more reference persons;

(b) classifying into one or more groups the subject data set for a feature by one or more linear modeling analysis algorithms based on the reference data set thereby providing a classification; and (c) determining fetal aneuploidy or fetal gender for the sample based on the classification.

A26. The method of embodiment A25, further comprising performing linear modeling analysis in a pairwise analysis between each pair in the subject data set and the reference data set.

B1. An apparatus that identifies the presence or absence of a genetic variation comprising a programmable processor that implements a data set dimensionality reducer wherein the reducer implements a method comprising:

(a) identifying one or more dissimilarities for a feature between a subject data set and a reference data set by a statistical analysis wherein the subject data set comprises genomic nucleic acid sequence information of a sample from a subject and the reference data set comprises genomic nucleic acid sequence information of a biological specimen from one or more reference persons;

(b) generating a multidimensional matrix from the dissimilarities;

(c) reducing the multidimensional matrix into a reduced data set representation of the matrix;

(d) classifying into one or more groups the reduced data set representation by one or more linear modeling analysis algorithms thereby providing a classification; and (e) determining the presence or absence of a genetic variation for the sample based on the classification.

C1. A computer program product, comprising a computer usable medium having a computer readable program code embodied therein, the computer readable program code adapted to be executed to implement a method for generating a reduced data set representation, the method comprising:

(a) identifying one or more dissimilarities for a feature between a subject data set and a reference data set by a statistical analysis wherein the subject data set comprises genomic nucleic acid sequence information of a sample from a subject and the reference data set comprises genomic nucleic acid sequence information of a biological specimen from one or more reference persons;

(b) generating a multidimensional matrix from the dissimilarities;

(c) reducing the multidimensional matrix into a reduced data set representation of the matrix;

(d) classifying into one or more groups the reduced data set representation by one or more linear modeling analysis algorithms thereby providing a classification; and (e) determining the presence or absence of a genetic variation for the sample based on the classification.

D1. A method for non-invasive assessment of a genetic variation comprising:

(a) determining dissimilarities for samples between (i) features of genomic nucleic acid and (ii) a linear relation for the features;

(b) generating a multidimensional matrix from the dissimilarities between the samples;

(c) reducing the multidimensional matrix into a reduced data set representation of the matrix;

(d) classifying into one or more groups the reduced data set representation, thereby providing a classification; and (e) determining the presence or absence of a genetic variation for the samples based on the classification.

D2. The method of embodiment D1, wherein the genomic nucleic acid is circulating cell free nucleic acid.

D3. The method of embodiment D2, wherein one of the features is a number of sequence reads of the genomic nucleic acid mapped to a portion of a reference genome.

D4. The method of embodiment D3, wherein the number of sequence reads is the total number of sequence reads mapped to the portion of the reference genome.

D5. The method of any one of embodiments D2 to D4, wherein one of the features is guanine and cytosine content of the portion of the reference genome.

D6. The method of any one of embodiments D3 to D5, wherein the portion of the reference genome is a chromosome or portion thereof.

D7. The method of any one of embodiments D3 to D6, wherein the linear relation is for the number of sequence reads mapped to the portion of the reference genome and the guanine and cytosine content of the portion of the reference genome for multiple portions of the reference genome.

D8. The method of embodiment D7, wherein the multiple portions of the reference genome are different chromosomes.

D9. The method of any one of embodiments D1 to D8, wherein the genetic variation is a fetal aneuploidy.

D10. The method of embodiment D9, wherein the linear relation is determined from one or more euploid samples.

D11. A method for non-invasive assessment of fetal aneuploidy, comprising:

(a) determining dissimilarities for samples between (i) features of circulating cell-free genomic nucleic acid and (ii) a linear relation for the features identified for the genomic nucleic acid, wherein:

one feature is a number of sequence reads mapped to a portion of a reference genome and another feature is guanine and cytosine content of the portion of the reference genome; and which linear relation is for multiple portions of the reference genome;

(b) generating a multidimensional matrix from the dissimilarities between the samples;

(c) reducing the multidimensional matrix into a reduced data set representation of the matrix;

(d) classifying into one or more groups the reduced data set representation, thereby providing a classification; and (e) determining the presence or absence of a fetal aneuploidy for the samples based on the classification.

D12. The method of any one of embodiments D1 to D8, wherein the genetic variation is fetal gender.

D13. The method of embodiment D12, wherein the linear relation is determined from one or more female or male samples.

D14. The method of any one of embodiments D1 to D8, wherein the genetic variation is a fetal fraction estimation.

D15. The method of any one of embodiments D1 to D14, wherein the classifying in (d) is performed by one or more linear modeling analysis algorithms.

D16. The method of any one of embodiments D3 to D8, further comprising obtaining genomic nucleic acid reads and mapping the reads to the portion of the reference genome.

D17. The method of any one of embodiments D3 to D8, further comprising isolating genomic nucleic acid from samples from subjects.

D18. The method of any one of embodiments D1 to D17, wherein the samples comprise subject samples, reference samples and combinations thereof.

D19. The method of embodiment D18, wherein some or all of the samples are from different persons.

D20. The method of embodiment D18 or D19, wherein some or all of the samples are aliquots from the same person.

D21. The method of any one of embodiments D1 to D20, wherein the genomic nucleic acid is from blood serum or blood plasma from the subject.

D22. The method of any one of embodiments D3 to D8, wherein the sequence reads are from a multiplex sequence analysis.

D23. The method of any one of embodiments D1 to D22, further comprising reiterating identification of the one or more dissimilarities in a pairwise analysis between each pair in the subject data set and the reference data set.

D24. The method of any one of embodiments D1 to D23, wherein determining the dissimilarities in (a) comprises employing one or more of a decision tree, counternull, multiple comparisons, omnibus test, Behrens-Fisher problem, bootstrapping, Fisher's method for combining independent tests of significance, null hypothesis, type I error, type II error, exact test, one-sample Z test, two-sample Z test, paired Z-test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, and combination thereof.

D25. The method of any one of embodiments D1 to D24, wherein reducing the multidimensional matrix in (c) comprises employing one or more of metric and non-metric multi-dimensional scaling, Sammon's non-linear mapping, principal component analysis and combinations thereof.

D26. The method of any one of embodiments D1 to D25, wherein the classifying in (d) comprises employing one or more of analysis of variance, Anscombe's quartet, cross-sectional regression, curve fitting, empirical Bayes methods, M-estimator, nonlinear regression, linear regression, multivariate adaptive regression splines, lack-of-fit sum of squares, truncated regression model, censored regression model, simple linear regression, segmented linear regression, decision tree, k-nearest neighbor, supporter vector machine, neural network, linear discriminant analysis, quadratic discriminant analysis, and combinations thereof.

D27. The method of any one of embodiments D1 to D26, further comprising determining a statistical sensitivity and a statistical specificity from the classified reduced data set representation.

D28. The method of embodiment D27, wherein the statistical sensitivity and statistical specificity are independently between about 85% and about 100%.

D29. The method of any one of embodiments D1 to D28, wherein the dissimilarity in (a) is distance of a feature from the linear relation.

D30. The method of any one of embodiments D1 to D29 wherein the dissimilarities are Z-scores.

D31. The method of embodiment D30, wherein the multidimensional matrix in (b) comprises pairwise dissimilarities between samples of the Z-scores.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for non-invasive estimation of fetal fraction comprising:
    (a) sequencing circulating cell-free nucleic acid from a test sample from a pregnant subject by a massively parallel sequencing (MPS) process, thereby generating a subject data set comprising nucleic acid sequence reads;
    (b) receiving a reference data set comprising nucleic acid sequence reads from multiple female reference samples;
    (c) generating a linear relation of a log sequence read count ratio and GC content for the subject data set;
    (d) performing a linear modeling analysis in pairwise analyses between respective pairs in the subject data set and the reference data set; and
    (e) estimating fetal fraction for the test sample based on an average fetal fraction determined according to a deviation of chromosome X from an expected position to an observed position in each pairwise analysis.

2. The method of claim 1, wherein the subject data set comprises millions of nucleic acid sequence reads.

3. The method of claim 1, wherein the reference data set comprises millions of nucleic acid sequence reads.

4. The method of claim 1, wherein (c), (d), and (e) are performed by a processor.

5. The method of claim 1, wherein the test sample is from the pregnant subject and some or all of the reference samples are from different persons.

6. The method of claim 1, further comprising mapping the nucleic acid sequence reads to portions of a reference genome.

7. The method of claim 1, further comprising, prior to the sequencing, isolating the circulating cell-free nucleic acid from the test sample from the pregnant subject.

8. The method of claim 1, wherein the circulating cell-free nucleic acid is from blood, serum, or blood plasma from the pregnant subject.

9. The method of claim 1, wherein the massively parallel sequencing (MPS) process is performed at a coverage of about 1-fold or less.

10. The method of claim 1, wherein the massively parallel sequencing (MPS) process is performed at a coverage of about 0.2-fold to about 1-fold.

11. The method of claim 1, wherein (d) comprises generating a z-score based on the linear modeling analysis for the pairwise samples.

12. The method of claim 1, further comprising sequencing circulating cell-free nucleic acid from multiple female reference samples by a massively parallel sequencing (MPS) process, thereby generating the reference data set comprising nucleic acid sequence reads from the multiple female reference samples.

* * * * *